US012564644B2

(12) United States Patent
Mathias et al.

(10) Patent No.: US 12,564,644 B2
(45) Date of Patent: Mar. 3, 2026

(54) CYCLODEXTRIN COMPLEXES OF SPECIALIZED PRORESOLVING MEDIATORS

(71) Applicant: THETIS PHARMACEUTICALS LLC, Ridgefield, CT (US)

(72) Inventors: Gary Mathias, Ridgefield, CT (US); Frank C. Sciavolino, Ridgefield, CT (US); Robert Lipper, Ridgefield, CT (US)

(73) Assignee: Thetis Pharmaceuticals LLC, Ridgefield, CT (US)

( * ) Notice: Subject to any disclaimer, the term of this patent is extended or adjusted under 35 U.S.C. 154(b) by 0 days.

(21) Appl. No.: 18/283,101

(22) PCT Filed: Mar. 1, 2023

(86) PCT No.: PCT/US2023/063450
§ 371 (c)(1),
(2) Date: Sep. 20, 2023

(87) PCT Pub. No.: WO2023/168245
PCT Pub. Date: Sep. 7, 2023

(65) Prior Publication Data

US 2024/0408229 A1 Dec. 12, 2024

Related U.S. Application Data

(60) Provisional application No. 63/268,820, filed on Mar. 3, 2022.

(51) Int. Cl.

| | |
|---|---|
| ***A61K 47/69*** | (2017.01) |
| ***A61K 31/202*** | (2006.01) |
| ***A61K 47/26*** | (2006.01) |

(52) U.S. Cl.
CPC ........ *A61K 47/6951* (2017.08); *A61K 31/202* (2013.01); *A61K 47/26* (2013.01)

(58) Field of Classification Search
CPC .. A61K 31/202; A61K 31/232; A61K 47/541; A61K 47/6951; A61K 47/40; A61P 29/00; A61P 35/00–04
See application file for complete search history.

(56) References Cited

U.S. PATENT DOCUMENTS 5,441,951 A 8/1995 Serhan
5,648,512 A 7/1997 Serhan
(Continued)

FOREIGN PATENT DOCUMENTS

WO WO-2017153977 A1 * 9/2017
WO 2019108605 A1 6/2019
WO 2023168245 A2 9/2023

OTHER PUBLICATIONS

Szente, L. et al "Cyclodextrin-lipid complexes . . . " Struct. Chem., vol. 28, pp. 479-492. (Year: 2017).*
(Continued)

*Primary Examiner* — Eric Olson
(74) *Attorney, Agent, or Firm* — KDW Firm PLLC

(57) ABSTRACT

The present invention provides complexes of a specialized pro-resolving mediator (SPM), or a salt, ester, or amide thereof, and a cyclodextrin (CD), wherein the SPM is a hydroxylated, polyunsaturated fatty acid derived from arachidonic acid, eicosapentaenoic acid, docosahexaenoic acid, or docosapentaenoic acid, 20 or 22 carbon atoms in length, with 4, 5 or 6 conjugated double bonds arranged in diene, triene, or tetraene systems or combinations thereof; and related compositions and methods.

18 Claims, 23 Drawing Sheets

(56) References Cited

U.S. PATENT DOCUMENTS

| | | | |
|---|---|---|---|
| 6,048,897 A | 4/2000 | Serhan | |
| 6,316,648 B1 | 11/2001 | Serhan | |
| 6,569,075 B2 | 5/2003 | Serhan | |
| 6,627,658 B2 | 9/2003 | Serhan | |
| 6,670,396 B2 | 12/2003 | Serhan | |
| 6,887,901 B1 | 5/2005 | Serhan | |
| 7,053,230 B2 | 5/2006 | Serhan | |
| 7,288,569 B2 | 10/2007 | Serhan | |
| 7,294,728 B2 | 11/2007 | Serhan | |
| 7,378,444 B2 | 5/2008 | Goodman | |
| 7,585,856 B2 | 9/2009 | Serhan | |
| 7,595,341 B2 | 9/2009 | Goodman | |
| 7,709,669 B2 | 5/2010 | Serhan | |
| 7,737,178 B2 | 6/2010 | Serhan | |
| 7,741,369 B2 | 6/2010 | Serhan | |
| 8,008,282 B2 | 8/2011 | Serhan | |
| 8,119,691 B2 | 2/2012 | Serhan | |
| 8,273,792 B2 | 9/2012 | Serhan | |
| 8,349,896 B2 | 1/2013 | Serhan | |
| 8,461,201 B2 | 6/2013 | Petasis | |
| 8,569,542 B2 | 10/2013 | Serhan | |
| 8,853,437 B2 | 10/2014 | Arita et al. | |
| 9,364,454 B2 | 6/2016 | Serhan | |
| 9,782,379 B2 | 10/2017 | Marette et al. | |
| 10,233,167 B2 | 3/2019 | Sherhan | |
| 2006/0293288 A1 | 12/2006 | Serhan | |
| 2012/0245229 A1 | 9/2012 | Serhan | |
| 2018/0116990 A1 | 5/2018 | Das | |
| 2020/0010339 A1 | 1/2020 | Serhan | |
| 2020/0048177 A1 | 2/2020 | Dalli et al. | |
| 2020/0179521 A1 | 6/2020 | Sciavolino | |
| 2020/0330551 A1 * | 10/2020 | Kantarci | A61K 38/1793 |

OTHER PUBLICATIONS

Serhan, C.N. et al., "Lipid Mediators in the Resolution of Inflammation," Cold Spring Harbor Perspectives in Biology, Oct. 30, 2014; 7(2):a013611.

Serhan, C.N. "Pro-resolving lipid mediators are leads for resolution physiology," Nature, vol. 510, pp. 92-101, 2014, abstract only.

Cousseans, Lisa et al., "Inflammation and Cancer," Nature, Dec. 4, 2002, 420(6917):860-7.doi: 10.1038/nature01322.

Grivennikov, Sergei et al., "Immunity, Inflammation and Cancer," Cell, vol. 140, issue 6, pp. 883-899, Mar. 19, 2010.

Todoric, Jelena et al., "Targeting Inflammation in Cancer Prevention and Therapy," Cancer Prevention Research, vol. 9, Issue 12, Dec. 1, 2016.

Fishbein, Anna et al., "Carcinogenesis: Failure of resolution of inflammation?" Pharmacology & Therapeutics, vol. 218. 2021, pp. 1-35.

Fullerton, JN et al., "Resolution of inflammation: a new therapeutic frontier," Nature Reviews Drug Discovery, Mar. 29, 2016, abstract and "key points".

Dalli, Jesmond et al., "Identification and structure elucidation of the pro-resolving mediators provides novel leads for resolution pharmacology," British Journal of Pharmacology, vol. 176, Issue 8, Apr. 2019. pp. 983-1170.

Sulciner, Megan et al., "Resolvins suppress tumor growth and enhance cancer therapy," Journal of Experimental Medicine, Nov. 30, 2017, vol 215, No. 1, pp. 115-140.

Gilligan, Molly et al., "Aspirin-triggered proresolving mediators stimulate resolution in cancer," PNAS, vol. 116, Mar. 12, 2019.

Maddipati, Krishna et al., "Stability and analysis of eicosanoids and docosanoids in tissue culture media," Prostaglandins Other Lipid Mediat. vol. 94, Issues 1-2, Feb. 2011, abstract and "section snippets".

Lombardo, Daniel, "Thesis: Synthseis of a benzene-annulated analogue of resolving E1 and other lipid mediators," Curtin University, 2015, pp. 33-34.

Fukuda, Hayato et al., "Design and Synthesis of Cyclopropane Congeners of Resolvin E2, an Endogenous Proresolving LipidMediator, as Its Stable Equivalents," Org. Lett., Nov. 28, 2016, 18,24, 6224-6227.

Petasis Nicos et al., "Design and synthesis of benzo-lipoxin A4 analogs with enhanced stability and potent anti-inflammatory properties," Bioorganic & Medicinal Chemistry Letters, vol. 18, Issue 4, Feb. 15, 2008, abstract only.

Orr, Sarah et al., "Proresolving actions of a new resolvin D1 analog mimetic qualifies as an immuresolvent," American Journal of Physiology-Lung Cellular and Molecular Physiology, vol. 308, Issue 9, May 2015.

Popielec, Agnieszka et al., "Effects of cyclodextrins on chemical stability of drugs," International Journal of Pharmaceutics, vol. 531, Issue 1, Oct. 15, 2017, pp. 532-542, abstract and "section snippets".

Uekama, Kaneto et al., "Stabilizing and Solubilizing Effects of SulfobutylEther B-Cyclodextrin on Prostaglandin E1 Analogue," Pharmceutical Research, vol. 18, pp. 1578-1585, Nov. 2001, partial abstract.

Hamada, Yoko et al., "Interactions of a-and B-Cyclodextrin with Several Non-Steroidal Antiinflammatory Drugs in Aqueous Solution," Hoshi Institute of Pharmaceutical Sciences, Chem. Pharm. Bull 23(6) 1205-1211 (1975).

Uekama, Kaneto et al., "Recent Aspect of Cyclodextrin-Based Drug Delivery System," Journal of Inclusion Phenomena and Macrocyclic Chemistry, vol. 56, pp. 3-8, 2006.

Obrosov, Alexander et al., "Effect of Fish Oil vs. Resolvin D1, Methyl Esters of Resolvins D1 and D2 on Diabetic Peripheral Neuropathy," J Neurol Neurophysiol. 2017.

Loftsson, Thorstein et al., "Pharmacokinetics of cyclodextrins and drugs after oral and parenteral administration of drug/cyclodextrin complexes," J Pharm Pharmacol. May 2016, vol 68, pp. 544-555.

Desai, Neha et al., "Repaglinide-Cyclodextrin complexes: Preparation, Characterziation and in vivo evaluation of antihyperglycemic activity," Journal of Inclusion Phenomena and Macrocyclic Chemistry, vol. 70, pp. 217-225, (2011), abstract only.

Maestrelli, F. et al., "Improvement of oxaprozin solubility and permeability by the combined use of cyclodextrin, chitosan, and bile components," European Journal of Pharmaceutics and Biopharmaceutics, vol. 78, Issue 3, Aug. 2011, pp. 385-393, abstract and "section snippets".

Jablan, Jasna et al., "Comparative analysis of zaleplon complexation with cyclodextrins and hydrophilic polymers in solution and in solid state," Journal of Pharmaceutical and Biomedical Analysis, vol. 71, Dec. 2012, pp. 35-44, abstract and "section snippets".

Maestrelli, F. et al., "Phyiscal chemical characterization of binary systems of prilocaine hydrochloride with triacetyl-B-cylodextrin," Journal of Inclusion Phenoma and Macrocyclic Chemistry, vol. 68, pp. 437-445, 2010, abstract only.

Promzeleva, Maria et al., "Improved Biopharmaceutical Properties of Oral Formulation s of 1, 2, 4-Thiadiazole Derivative with Cyclodextrins: in Vitro and in Vivo Evaluation," ACS Biomater. Sci. Eng. 2018, 4, 2, pp. 491-501, abstract only.

Lim, Ji Yeon et al., "Biological Roles of Resolvins and Related Substances in Resolution of Pain," BioMed Research International, vol. 2015, Article 830930, 14 pages, 2015.

International Search Report and Written Opinion for International application No. PCT/US2023/063450, dated Sep. 26, 2023, 12 pages.

Jankowski et al., "Factors Affecting the Formation of 2:1 Host: Guest Inclusion Complexes of 2-[(R-Phenyl) amine]-1,4-naphthalenediones (PAN) in β- and γ-Cyclodextrins," Molecules, vol. 21, 1568 (2016).

Ryzhakov et al., "Self-Assembly of Cyclodextrins and Their Complexes in Aqueous Solutions," Journal of Pharmaceutical Sciences, vol. 105: 2556-2569 (2016).

Saokham et al., "Solubility of Cyclodextrins and Drug/Cyclodextrin Complexes," Molecules, vol. 23, 1161 (2018).

Szente et al., "Spontaneous Opalescence of Aqueous γ-Cyclodextrin Solutions: Complex Formation or Self-Aggregation," Journal of Pharmaceutical Sciences, vol. 87, No. 6: 778-781 (Jun. 1998).

* cited by examiner

RvE1 IN ALPHA-CD COMPLEX

RvE1 IN BETA-CD COMPLEX

RvE1 IN GAMMA-CD COMPLEX

RvE1 IN HP-BETA-CD COMPLEX

RvE1 IN SBE-BETA-CD COMPLEX

DIRECT BLEND BEFORE TABLETING

CORE TABLETS

CYCLODEXTRIN COMPLEXES OF SPECIALIZED PRORESOLVING MEDIATORS

CROSS REFERENCE TO RELATED APPLICATIONS

This application is a national stage application, filed under 35 U.S.C. § 371, of International Application No. PCT/US2023/063450, entitled "CYCLODEXTRIN COMPLEXES OF SPECIALIZED PRORESOLVING MEDIATORS," filed Mar. 1, 2023, which claims the benefit of priority under 35 U.S.C. § 119(e) to U.S. Provisional Application No. 63/268,820 filed Mar. 3, 2022, each of which is incorporated herein by reference in its entirety.

FIELD OF THE INVENTION

The present invention relates to inclusion complexes of cyclodextrins and specialized pro-resolving mediators (referred to herein as "SPMs"), including resolvins, protectins, lipoxins, and maresins, and their use in therapy.

BACKGROUND OF THE INVENTION

The inflammatory response in humans has two phases: initiation and resolution. At the cellular level, initiation is a protective response characterized by the production and release of pro-inflammatory mediators to activate the innate immune response, resulting in an influx of polymorphonuclear cells (PMNs) from blood to kill and clear foreign invaders and damaged cells. This initiation phase is an active process driven by metabolites of arachidonic acid including the prostaglandins, which are chemo-attractants for eosinophils, neutrophils and monocytes, and the leukotrienes, which elicit adhesion, chemotaxis, and aggregation of leukocytes.

During the peak of inflammation, as the inflammatory stimulus is being eliminated, the resolution phase begins, marked by a reduction of pro-inflammatory signals and a switch from the production and release of pro-inflammatory mediators to the production and release of specialized pro-resolving mediators (SPMs), including resolvins, protectins, lipoxins, and maresins. SPMs are hydroxylated polyunsaturated fatty acids derived from arachidonic acid, eicosapentaenoic acid, docosahexaenoic acid, or docosapentaenoic acid, 20 or 22 carbon atoms in length, with 4, 5 or 6 double bonds arranged in diene, triene, and/or tetraene systems. As the endogenous pro-resolution counterparts to prostaglandins and leukotrienes, SPMs drive the resolution phase by halting PMN infiltration and stimulating the recruitment and activation of monocytes and pro-resolving macrophages to clear the tissue of cellular debris in a non-phlogistic manner, enabling the return to tissue homeostasis (Serhan C. N. et al., Cold Spring Harb Perspect Biol 2015; 7:a016311).

Unresolved inflammation is an important but underappreciated driver of many chronic diseases and disorders. Accordingly, the ability to resolve excessive inflammation is of paramount importance to human health (Serhan C. N., Nature 2014 510:92-101; Coussens et al., Nature 2002; 420, 860-867, Grivennikov et al., Cell. 2010; 140 (6):883-99, Todoric et al., Cancer Prev Res. 2016; 9 (12):895-905; Fishbein et al., Pharmacol Ther. 2021; 218:107670).

In vitro studies of SPMs demonstrate potent effects on inflammatory and other markers at nanomolar concentrations. In vivo studies of SPMs in a broad range of inflammatory disease and tumor models demonstrate effects on disease progression and symptoms. These data provide the scientific basis for therapeutic administration of SPMs to treat chronic inflammatory diseases and cancer. (Fullerton J N, Gilroy D W., Nat Rev Drug Discov. 2016; 15 (8):551-567; Dalli J, Serhan C N., Br J Pharmacol. 2019; 176 (8):1024-1037; Sulciner M L, Serhan C N, Gilligan M M, et al., J Exp Med. 2018; 215 (1):115-140 Gilligan M M, Gartung A, Sulciner M L, Proc Natl Acad Sci US A. 2019; 116 (13):6292-6297).

To translate these unique and promising in vitro and in vivo findings into clinical benefit, there is a need to develop compositions able to deliver SPMs, including their analogs and derivatives, in therapeutically effective amounts to target tissues. The present invention addresses this need by providing stabilized SPMs in complexes with cyclodextrins.

SUMMARY OF THE INVENTION

The present invention relates to complexes of SPMs and cyclodextrins (referred herein as "SPM complexes") for use in the treatment of inflammatory diseases and cancer. The SPM complexes and methods described here are based on unexpected findings of improved chemical and physical stability of the SPM moiety when complexed with cyclodextrins and exposed to air at elevated temperature and humidity, thus increasing the ability to manufacture, formulate, package, inventory, distribute and utilize pharmaceutical compositions of SPMs to prevent and treat inflammatory diseases and cancer. More particularly, the invention relates to SPM complexes and their use in pharmaceutical compositions, wherein the stability of the SPM active moiety is remarkably improved.

The invention provides a complex of a specialized pro-resolving mediator (SPM), or a salt, ester, or amide thereof, and a cyclodextrin (CD), wherein the SPM is a hydroxylated, polyunsaturated fatty acid derived from arachidonic acid, eicosapentaenoic acid, docosahexaenoic acid, or docosapentaenoic acid, 20 or 22 carbon atoms in length, with 4, 5 or 6 conjugated double bonds arranged in diene, triene, or tetraene systems or combinations thereof.

In embodiments, the SPM is selected from the group consisting of RvE1, RvE2, RvE3, RvE4, AT-RvE1, AT-RvE2, AT-RvE3, RvD1, RvD2, RvD3, RvD4, RvD5, RvD6, AT-RvD1, AT-RvD2, AT-RvD3, AT-RvD4, AT-RvD5, AT-RvD6, RvT1, RvT2, RvT3, RvT4, LXA4, LXB4, AT-LXA4, AT-LXB4, PD1, PDX, AT-PD1, MaR1, and MaR2, PD1n-3 DPA or MaR1n-3 DPA, or a salt, ester, or amide thereof; optionally wherein the SPM is RvE1, AT-RvE1, RvD1, AT-RvD1, RvD2, AT-RvD1, AT-RvD2, LxA4, or AT-LxA4, or a salt, ester, or amide thereof.

In embodiments, the cyclodextrin is selected from alpha-cyclodextrin (alpha-CD), beta-cyclodextrin (beta-CD), gamma-cyclodextrin (gamma-CD), 2-hydroxypropyl-beta-cyclodextrin (HP-beta-CD), sulfobutylether beta-cyclodextrin (SBE-beta-CD); 2-hydroxypropyl-alpha-cyclodextrin; randomly methylated beta-cyclodextrin; 2-O-methyl-beta-cyclodextrin; 2,6-di-O-methyl-beta-cyclodextrin; heptakis (2,3,6-tri-O-methyl)-beta-cyclodextrin; carboxymethyl-beta-cyclodextrin; carboxyethyl-beta-cyclodextrin; hydroxyethyl-beta-cyclodextrin; maltosyl-beta-cyclodextrin; 3,6-(N,N,N-trimethylammonium) propyl-beta-cyclodextrin; acetyl-beta-cyclodextrin; 2,6-di-O-methyl-gamma-cyclodextrin; 2-hydroxypropyl-gamma-cyclodextrin; or sulfobutylether gamma-cyclodextrin; optionally, wherein the cyclodextrin is alpha-cyclodextrin (alpha-CD), beta-cyclodextrin (beta-CD), gamma-cyclodextrin (gamma-CD), 2-hydroxypropyl-beta-cyclodextrin (HP-beta-CD), or sulfobutylated-beta-cyclodextrin (SBE-beta-CD); optionally wherein the cyclodextrin is gamma-cyclodextrin (gamma-CD) or 2-hydroxypropyl-beta-cyclodextrin (HP-beta-CD).

In embodiments, the SPM is present in a percentage weight amount relative to the total weight of the complex (including only the weights of the SPM and cyclodextrin molecules), ranging from 1.5% to 35%, 2% to 30%, 3% to 25%, or 4% to 20%.

In embodiments, the SPM and cyclodextrin are present in a molar ratio ranging from 2:1 to 1:4, or optionally 1:1 to 1:3, or 1:1.5 to 1:2.5, or 1:2.

In embodiments, the SPM is in the form of a salt. In embodiments, the SPM is in the form of a sodium, potassium, calcium, zinc, or magnesium salt. In embodiments, the SPM is a magnesium dilysinate salt. In embodiments, the SPM is a sodium salt. In embodiments, the SPM is a RvE1 sodium salt.

In embodiments, the SPM is in the form of a salt described by Formula I:

(Formula I)

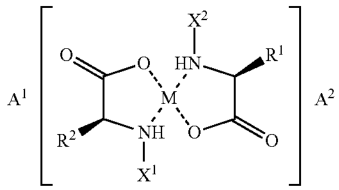

wherein

M is a divalent metal selected from magnesium (Mg2+), calcium (Ca2+), and zinc (Zn2+);

A1 and A2 are each the same SPM molecule;

R1 and R2 are each independently a C1-C10 alkyl comprising at least one basic function; and X1 and X2 are each independently H or CO—Z and Z is a peptide comprising 1 to 5 amino acids.

In embodiments of Formula I, M is selected from magnesium (Mg2+) or calcium (Ca2+).

In embodiments of Formula I, R1 and R2 are each independently —(CH2) 3-Y1, and —(CH2) 4-Y2, and Y1 and Y2 are each selected from a positively charged primary amine, a positively charged secondary amine, a positively charged tertiary amine, and a positively charged guanidine.

In embodiments of Formula I, X1 and X2 are each H.

In embodiments of Formula I, R1 and R2 are each —(CH2) 4-Y2 and Y2 is —NH3+.

In embodiments of Formula I, M is magnesium (Mg2+), R1 and R2 are each —(CH2) 4-Y2 and Y2 is —NH3+, X1 and X2 are each H, and A1 and A2 are RvE1, which SPM of the complex is referred to as RvE1 magnesium dilysinate, or "RvE1 MgLys".

In embodiments of Formula I, M is magnesium (Mg2+), R1 and R2 are each —(CH2) 4-Y2 and Y2 is —NH3+, X1 and X2 are each H, and A1 and A2 are RvD1, which SPM of the complex is referred to as RvD1 magnesium dilysinate, or "RvD1 MgLys".

In embodiments of Formula I, M is magnesium (Mg2+), R1 and R2 are each —(CH2) 4-Y2 and Y2 is —NH3+, X1 and X2 are each H, and A1 and A2 are RvD2, which SPM of the complex is referred to as RvD2 magnesium dilysinate, or "RvD2 MgLys".

In embodiments of Formula I, M is magnesium (Mg2+), R1 and R2 are each —(CH2) 4-Y2 and Y2 is —NH3+, X1 and X2 are each H, and A1 and A2 are LxA4, which SPM of the complex is referred to as LxA4 magnesium dilysinate, or "LxA4 MgLys".

In embodiments of the complexes comprising an SPM of Formula I, the cyclodextrin component of the complex is gamma-cyclodextrin (gamma-CD) or 2-hydroxypropyl-beta-cyclodextrin (HP-beta-CD).

The invention also provides methods for preparing the complexes described herein. In embodiments, the method comprises combining an amount of the SPM, or salt thereof, with an amount of the cyclodextrin to form a mixture; dissolving the mixture in water; and isolating the complex by a process comprising one or more of filtration to obtain a filtrate followed by freeze-drying of the filtrate, crystallization, co-evaporation, or spray-drying. In embodiments, the step of dissolving is performed under nitrogen, for example by stirring under nitrogen for from 1-3 hours. Also provided are complexes prepared by the foregoing method.

In embodiments, the SPM component of the complexes described here has a chemical purity of at least 88% as determined by high pressure liquid chromatography (HPLC) under conditions of 40° C. and 75% relative humidity, with exposure to air, for at least 8 weeks, or 12 weeks or 16 weeks.

In embodiments, the SPM component of the complexes described here has a chemical purity of at least 90% or at least 92% or at least 94%, as determined by HPLC.

In embodiments, the number of degradation peaks of the SPM component of the complex present at greater than or equal to 1.0% is less than 8, less than 6, or less than 4, or no more than 2, as determined by HPLC. In embodiments, the number of degradation peaks of the SPM component of the complex that are present at greater than or equal to 0.2% is less than 16, optionally less than 14 or less than 12 or less than 10, or no more than 8, as determined by HPLC.

The invention also provides a complex prepared by the methods described herein.

The invention also provides a composition comprising a complex as described herein, and one or more pharmaceutically acceptable carriers and/or excipients.

In embodiments, the composition is formulated as an oral, pulmonary, rectal, parenteral, transdermal, subcutaneous, intravenous, intramuscular, intraperitoneal, inhalational, buccal, sublingual, intrapleural, intrathecal, or intranasal dosage form; optionally wherein the composition is formulated as an oral or parenteral dosage form.

In embodiments, a composition described herein is for use in a method of treating an inflammatory disease or disorder of the gastrointestinal tract selected from inflammatory bowel disease (IBD), ulcerative colitis, Crohn's disease, proctitis, pouchitis, Crohn's disease of the pouch, eosinophilic colitis, lymphocytic colitis, collagenous colitis, diversion colitis, chemical colitis, ischemic colitis, eosinophilic esophagitis, Behcet's disease, irritable bowel syndrome, Celiac disease, intestinal mucositis, diverticulitis, and short bowel syndrome, optionally wherein the inflammatory disease or disorder is ulcerative colitis, Crohn's disease, or pouchitis.

In embodiments, a composition described herein is for use in a method of treating cancer, optionally wherein the cancer is a solid tumor cancer such as brain cancer, breast cancer, bladder cancer, colorectal cancer, esophageal cancer, gastric cancer, head and neck cancer, liver cancer, lung cancer, melanoma, ovarian cancer, pancreatic cancer, prostate cancer, renal cell carcinoma, or sarcoma, optionally wherein the cancer is colorectal cancer, gastric cancer, liver cancer, lung cancer, ovarian cancer, or pancreatic cancer.

In embodiments, the composition is administered orally or parenterally, optionally wherein the parenteral administration is subcutaneous, intraperitoneal, intramuscular, or intravenous; optionally wherein the pharmaceutical compositions is administered sublingually or by inhalation.

DETAILED DESCRIPTION OF THE INVENTION

Figure 1:
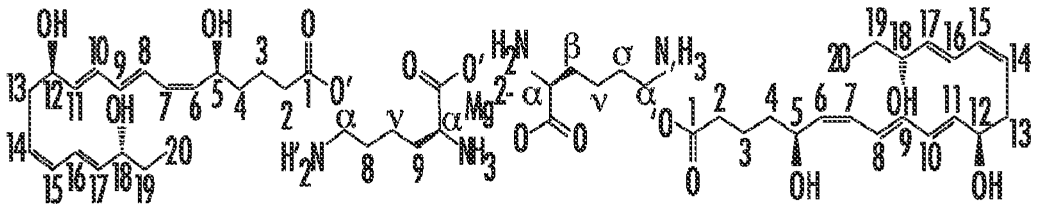
FIG. 1: Structure and atom number assignment of RvE1-MgLys.

It is an object of this invention to provide SPM complexes, their preparation, and their use in pharmaceutical compositions, wherein the SPM active moiety is stabilized against chemical degradation.

Despite their promising pharmacology, SPMs are chemically unstable in part due to the tendency of their conjugated double-bond system to isomerize into a thermodynamically more favorable state, a tendency first noted in aqueous environments such as phosphate buffered solutions and tissue culture media (Maddipati et al., Prostaglandins Other Lipid Mediat. 2011; 94 (1-2): 59-72). SPMs are hydroxylated polyunsaturated fatty acids derived from eicosapentaenoic acid, docosahexaenoic acid, or docosapentaenoic acid, 20 or 22 carbon atoms in length, with 5 or 6 double bonds arranged in diene, triene, and/or tetraene systems. For example, the 6Z, 8E, 10E triene system of Resolvin E1 (RvE1) is thermodynamically unstable, causing it to isomerize to the lower energy all-trans structure. This isomerization leads to the conversion of the 6,7-cis double bond into the 6,7-trans isomer with significantly reduced biological activity, showing 70% less activity in various assays (Lombardo Thesis, Curtin University, January 2015, at p. 33-34).

Structural modifications addressing the inherent vulnerability of the conjugated double-bond structure of SPMs, specifically the tendency of the diene, triene and tetraene systems to isomerize to a less potent trans configuration, have been proposed to stabilize SPMs. Lombardo proposed structural modification of RvE1 to stabilize the molecule, specifically via formation of a benzene analog to block isomerization of the 6,7-cis double bond. Use of cyclopropane congeners and benzene congeners of Resolvin E2 (RvE2) have been proposed to stabilize its double bond structure (Fukuda H, et al., Org Lett. 2016; 18 (24): 6224-6227; Murakami Y, et al., ACS Med Chem Lett. 2020; 11 (4): 479-484). A similar strategy was proposed for Lipoxin A4 (LxA4) via insertion of a benzo-fused ring system to counteract the tendency of the 11Z double bond in the 7E, 9E, 11Z, 13E tetraene system of LxA4 to isomerize into an all-trans configuration (Petasis et al., Bioorg Med Chem Lett. 2008; 18 (4): 1382-138). Likewise, use of benzene-fused ring was proposed to stabilize Resolvin D1 (RvD1) against isomerization of its tetraene system (Orr et al., Am J Physiol Lung Cell Mol Physiol. 2015; 308 (9): L904-L911). Although these structural modifications can stabilize the SPM against isomerization, they can also result in reduced potency compared to the native, unmodified SPM molecule. For example, Lombardo reports that the benzo-Resolvin E1 analog has four times less binding affinity to one of the known RvE1 receptors compared to the native RvE1 molecule (Lombardo 2015, p. 113). Likewise, the benzo-Lipoxin A4 compounds described by Petasis are less biologically active compared to a control Lipoxin A4 analog, ranging from 20% to 50% less potency (Table 2, Petasis 2008). In addition to potential loss of biological activity, structural SPM analogs may present additional safety and/or efficacy issues due to off-target effects compared to the native, unmodified SPM molecule.

An alternative strategy is described in WO2017210604, which demonstrates that formation of mineral amino acid chelate salts of native SPMs, such as magnesium di-lysinate resolvin E1 (RvE1-MgLys), increased their solid-state chemical stability under standard conditions, namely 20-24° C., 40% relative humidity, exposed to air. However, further studies by the present inventors revealed that these compounds exhibited undesirable levels of chemical instability over time under accelerated conditions of 40° C., 75% relative humidity, exposed to air. The present invention addresses the need to further stabilize SPMs against chemical instability when exposed to air under conditions of elevated temperature and humidity, which reduces risk of potency loss and/or appearance of unknown impurities with potential safety issues during manufacturing, formulation, packaging, storage, and distribution.

The present invention is based, in part, on the unexpected discovery that complexation with cyclodextrins stabilizes the vulnerable triene structure of RvE1. Without being bound by any theory, the unique orientation of RvE1 inside various cyclodextrins is believed to protect the triene system against degradation due to exposure to light, air, and humidity. Similar stabilization against isomerization is expected for other SPMs with similar chemical structures, notably conjugated double bond systems consisting of diene, triene and/or tetraene systems, which include the SPMs described in Table 1 below.

Accordingly, the invention provides complexes of an SPM, or a salt thereof, or an ester, or amide of an SPM molecule, and a cyclodextrin, wherein the SPM contains a diene, triene, and/or tetraene system, as well as methods for making the complexes and methods for their use in therapy. These complexes are advantageously stabilized against chemical degradation, particularly when exposed to air under conditions of elevated temperature and humidity (i.e., 40° C. and 75% relative humidity) for a period of up to 16 or 24 weeks, which would otherwise result in significant degradation of the SPM molecule and an increase in degradation products and concomitant decrease in chemical purity that together could impede use of the SPM as a pharmaceutical drug. For example, following 16 weeks of exposure to air at the elevated temperature and humidity conditions described above, the RvE1 moiety in RvE1-MgLys alone had significantly degraded from 94.0% to 80.7%, whereas the RvE1 moiety in five different cyclodextrins complexed with RvE1-MgLys degraded from 95.4% to 91.7% on average. Thus, compared to RvE1-MgLys alone, the cyclodextrins reduced RvE1 degradation by 70% on average and the gamma-cyclodextrin reduced RvE1 degradation by 91%. The term "chemical purity" as used herein refers to the amount, given as an area percentage, of the active moiety of a particular compound in a sample of the compound. Unless stated otherwise, percentages stated with respect to chemical purity throughout this specification are area percentages, calculated as the ratio of (a) the area of a peak corresponding to the SPM active moiety, isomer, epimer, other impurity or degradation product to (b) the sum of the peak areas of detectable constituents of the sample measured by high pressure liquid chromatography (HPLC).

Although cyclodextrins are known to impact the chemical and photostability of various small molecules, including eicosanoids, a comprehensive review by Popielec and Loftsson in 2017 also identified several molecules that are destabilized by cyclodextrins, underscoring the fact that the effects of a particular cyclodextrin on the stability of any particular molecule is unpredictable (Popielec A, Loftsson T., Int J Pharm. 2017; 531 (2): 532-542). For example, a study of various cyclodextrins complexed with a Prostaglandin E1 analog in solution (phosphate buffer, pH 8.0, at 60° C.) showed that six of the eight cyclodextrins tested accelerated degradation of the analog compared to control (see Table 1, Uekama K, et al., Pharm Res. 2001; 18 (11): 1578-1585). Furthermore, molecules that are stabilized in aqueous solution by a cyclodextrin can be destabilized by the same cyclodextrin in a solid dosage form (Hamada Y, et al., Chem Pharm Bull (Tokyo). 1975; 23 (6): 1205-1211; Uekama 2006; Popielec 2017). According to Uekama 2006, "cyclodextrins are known to accelerate and decelerate various kinds of reactions depending on the nature of the complex formed". In particular, the degree of inclusion and orientation of a guest molecule in a cyclodextrin, particularly with respect to the reactive site of the molecule, plays a critical role in determining the stabilizing effect of the cyclodextrin (Popielec 2017). Thus, "the use of cyclodextrins to improve the stability of a given drug cannot be predicted and must be thoroughly studied and the formulation carefully designed" (Rincón-López 2021).

The Complexes

The present invention relates to complexes of an SPM molecule, or a salt thereof, or an ester, or amide thereof, and a cyclodextrin.

The Cyclodextrin Component of the Complexes

The term "cyclodextrin" refers to a cyclic oligosaccharide consisting of at least six glucopyranose units joined by alpha-1, 4 glycosidic bonds in which the oligosaccharide ring forms a toroid or cone-like structure. In the context of the present invention, a cyclodextrin having six glucose subunits is referred to as alpha-cyclodextrin, a cyclodextrin having seven glucose subunits is referred to as beta-cyclodextrin, and a cyclodextrin having eight glucose subunits is referred to as gamma-cyclodextrin. Collectively, these cyclodextrins are known as native cyclodextrins. In addition, the term "cyclodextrin" also refers to randomly substituted derivatives of the native cyclodextrins including but not limited to 2-hydroxypropyl-alpha-cyclodextrin; randomly methylated beta-cyclodextrin; 2-O-methyl-beta-cyclodextrin; 2,6-di-O-methyl-beta-cyclodextrin; 2-hydroxypropyl-beta-cyclodextrin, heptakis (2,3,6-tri-O-methyl)-beta-cyclodextrin; carboxymethyl-beta-cyclodextrin; carboxyethyl-beta-cyclodextrin; hydroxyethyl-beta-cyclodextrin; maltosyl-beta-cyclodextrin; 3,6-(N,N,N-trimethylammonium) propyl-beta-cyclodextrin; acetyl-beta-cyclodextrin; sulfobutylether beta-cyclodextrin; 2,6-di-O-methyl-gamma-cyclodextrin; 2-hydroxypropyl-gamma-cyclodextrin; and sulfobutylether gamma-cyclodextrin.

The term "complex" refers to an inclusion compound in which a "guest" molecule is partially or completely contained within a void space or cavity of a "host" molecule or within a lattice of host molecules. In the context of the present invention, a "complex" is an inclusion compound formed by an SPM "guest" molecule and a cyclodextrin "host" molecule (also referred herein as an "SPM complex").

The SPM Component of the Complexes

The present invention relates to complexes of a specialized pro-resolving mediator (SPM), or a salt thereof, or an ester, or amide thereof, and a cyclodextrin, wherein the SPM contains a diene, triene, and/or tetraene system. The SPMs include resolvins, protectins, lipoxins, and maresins and their aspirin-triggered counterparts (e.g., aspirin-triggered lipoxins and protectins). These molecules are described, for example in U.S. Pat. Nos. 5,441,951 and 8,119,691 (lipoxins and aspirin-triggered lipoxins), U.S. Pat. No. 6,670,396 (aspirin-triggered lipid mediators), US 2006-0293288 (resolvins), U.S. Pat. Nos. 7,378,444 and 7,595,341 (analogs of lipid mediators derived from omega-3 fatty acids). An ester of an SPM may be an isopropyl, methyl, ethyl or glycerol ester (Obrosov A, et al. J Neurol Neurophysiol. 2017; 8 (6)).

In embodiments, the SPM component of the complexes described herein is selected from the molecules set forth in Table 1. In embodiments, the SPM component of the complexes described herein is, the free acid or a salt thereof, or an ester, or amide of an SPM described in Table 1. In embodiments, the SPM component of the complexes described herein is selected from RvE1, RvE2, RvE3, RvE4, AT-RvE1, AT-RvE2, AT-RvE3, RvD1, RvD2, RvD3, RvD4, RvD5, RvD6, AT-RvD1, AT-RvD2, AT-RvD3, AT-RvD4, AT-RvD5, AT-RvD6, RvT1, RvT2, RvT3, RvT4, LXA4, LXB4, AT-LXA4, AT-LXB4, PD1, PDX, AT-PD1, MaR1, and MaR2, PD1n-3 DPA or MaR1n-3 DPA, or a salt, ester, or amide thereof.

TABLE 1

SPMs Components of the Complexes

| Name | Abbrev. | Formula | Chemical Name | Double-Bond Systems |
|---|---|---|---|---|
| Resolvin E1 | RvE1 | $C_{20}H_{30}O_5$ | 5S,12R,18R-trihydroxy-6Z,8E,10E,14Z,16E-eicosapentaenoic acid | 1 triene<br>1 diene |
| Resolvin E2 | RvE2 | $C_{20}H_{30}O_4$ | 5S,18R-dihydroxy-6E,8Z,11Z,14Z,16E-eicosapentaenoic acid | 2 dienes |
| Resolvin E3 | RvE3 | $C_{20}H_{30}O_4$ | 17R,18R-dihydroxy-5Z,8Z,11Z,13E,15E-eicosapentaenoic acid | 1 triene |
| Resolvin E4 | RvE4 | $C_{20}H_{30}O_4$ | 5S,15S-dihydroxy-6E,8Z,11Z,13E,17Z-eicosapentaenoic acid | 2 dienes |
| Aspirin-triggered Resolvin E1 | AT-RvE1 | $C_{20}H_{30}O_5$ | 5S,12R,18S-trihydroxy-6Z,8E,10E,14Z,16E-eicosapentaenoic acid | 1 triene<br>1 diene |
| Aspirin-triggered Resolvin E2 | AT-RvE2 | $C_{20}H_{30}O_4$ | 5S,18S-dihydroxy-6E,8Z,11Z,14Z,16E-eicosapentaenoic acid | 2 dienes |
| Aspirin-triggered Resolvin E3 | AT-RvE3 | $C_{20}H_{30}O_4$ | 17R,18S-dihydroxy-5Z,8Z,11Z,13E,15E-eicosapentaenoic acid | 1 triene |
| Resolvin D1 | RvD1 | $C_{22}H_{32}O_5$ | 7S,8R,17S-trihydroxy-4Z,9E,11E,13Z,15E,19Z-docosahexaenoic acid | 1 tetraene |
| Resolvin D2 | RvD2 | $C_{22}H_{32}O_5$ | 7S,16R,17S-trihydroxy-4Z,8E,10Z,12E,14E,19Z-docosahexaenoic acid | 1 tetraene |
| Resolvin D3 | RvD3 | $C_{22}H_{32}O_5$ | 4S,11R,17S-trihydroxy-5Z,7E,9E,13Z,15E,19Z-docosahexaenoic acid | 1 triene<br>1 diene |
| Resolvin D4 | RvD4 | $C_{22}H_{32}O_5$ | 4S,5,17S-trihydroxy-6E,8E,10Z,13Z,15E,19Z-docosahexaenoic acid | 1 triene<br>1 diene |
| Resolvin D5 | RvD5 | $C_{22}H_{3204}$ | 78,17S-dihydroxy-4Z,8E,10Z,13Z,15E,19Z-docosahexaenoic acid | 2 dienes |
| Resolvin D6 | RvD6 | $C_{22}H_{32}O_4$ | 4S,17S-dihydroxy-5E,7Z,10Z,13Z,15E,19Z-docosahexaenoic acid | 2 dienes |
| Aspirin-triggered Resolvin D1 | AT-RvD1 | $C_{22}H_{32}O_5$ | 7S,8R,17R-trihydroxy-4Z,9E,11E,13Z,15E,19Z-docosahexaenoic acid | 1 tetraene |
| Aspirin-triggered Resolvin D2 | AT-RvD2 | $C_{22}H_{32}O_5$ | 7S,16R,17R-trihydroxy-4Z,8E,10Z,12E,14E,19Z-docosahexaenoic acid | 1 tetraene |
| Aspirin-triggered Resolvin D3 | AT-RvD3 | $C_{22}H_{32}O_5$ | 4S,11R,17R-trihydroxy-5Z,7E,9E,13Z,15E,19Z-docosahexaenoic acid | 1 triene<br>1 diene |
| Aspirin-triggered Resolvin D4 | AT-RvD4 | $C_{22}H_{32}O_5$ | 4S,5,17R-trihydroxy-6E,8E,10Z,13Z,15E,19Z-docosahexaenoic acid | 1 triene<br>1 diene |
| Aspirin-triggered Resolvin D5 | AT-RvD5 | $C_{22}H_{32}O_4$ | 7S,17R-dihydroxy-4Z,8E,10Z,13Z,15E,19Z-docosahexaenoic acid | 2 dienes |
| Aspirin-triggered Resolvin D6 | AT-RvD6 | $C_{22}H_{32}O_4$ | 4S,17R-dihydroxy-5E,7Z,10Z,13Z,15E,19Z-docosahexaenoic acid | 2 dienes |
| Resolvin T1 | RvT1 | $C_{22}H_{32}O_5$ | 7S,13R,20S-trihydroxy-8E,10Z,14E,16Z,18E-docosapentaenoic acid | 1 diene<br>1 triene |
| Resolvin T2 | RvT2 | $C_{22}H_{32}O_5$ | 7S,12R,13S-trihydroxy-8Z,10E,14E,16Z,19Z-docosapentaenoic acid | 1 tetraene |
| Resolvin T3 | RvT3 | $C_{22}H_{32}O_5$ | 7S,8R,13S-trihydroxy-9E,11E,14E,16Z,19Z-docosapentaenoic acid | 2 dienes |
| Resolvin T4 | RvT4 | $C_{22}H_{32}O_4$ | 7S,13R-dihydroxy-8E,10Z,14E,16Z,19Z-docosapentaenoic acid | 2 dienes |
| Lipoxin A4 | LxA4 | $C_{20}H_{32}O_5$ | 5S,6R,15S-trihydroxy-7E,9E,11Z,13E-eicosatetraenoic acid | 1 tetraene |
| Lipoxin B4 | LxB4 | $C_{20}H_{32}O_5$ | 58,14R,15S-trihydroxy-6E,8Z,10E,12E-eicosatetraenoic acid | 1 tetraene |
| Aspirin-triggered Lipoxin A4 | AT-LxA4 | $C_{20}H_{32}O_5$ | 5S,6R,15R-trihydroxy-7E,9E,11Z,13E-eicosatetraenoic acid | 1 tetraene |
| Aspirin-triggered Lipoxin B4 | AT-LxB4 | $C_{20}H_{32}O_5$ | 5S,14R,15R-trihydroxy-6E,8Z,10E,12E-eicosatetraenoic acid | 1 tetraene |
| Protectin D1 | PD1 | $C_{22}H_{32}O_4$ | 10R,17S-dihydroxy-4Z,7Z,11E,13E,15Z,19Z-docosahexaenoic acid | 1 triene |
| Protectin DX | PDX | $C_{22}H_{32}O_4$ | 10S,17S-dihydroxy-4Z,7Z,11E,13Z,15E,19Z-docosahexaenoic acid | 1 triene |
| Aspirin-triggered Protectin D1 | AT-PD1 | $C_{22}H_{32}O_4$ | 10R,17R-dihydroxy-4Z,7Z,11E,13E,15Z,19Z-docosahexaenoic acid | 1 triene |
| $PD1_{n\text{-}3\ DPA}$ * | $PD1_{n\text{-}3\ DPA}$ | $C_{22}H_{32}O_4$ | 10R,17S-dihydroxy-7Z,11E,13E,15Z,19Z-docosapentacnoic acid | 1 triene |

TABLE 1-continued

| SPMs Components of the Complexes | | | | |
|---|---|---|---|---|
| Name | Abbrev. | Formula | Chemical Name | Double-Bond Systems |
| Maresin 1 | MaR1 | $C_{22}H_{32}O_4$ | 7R,14S-dihydroxy-4Z,8E,10E,12Z,16Z,19Z-docosahexaenoic acid | 1 triene |
| Maresin 2 | MaR2 | $C_{22}H_{32}O_4$ | 13R,14S-dihydroxy-4Z,7Z,9E,11E,16Z,19Z-docosahexaenoic acid | 1 triene |
| $MaRl_{n\text{-}3\ DPA}$ * | $MaR1_{n\text{-}3\ DPA}$ | $C_{20}H_{32}O_4$ | 7S,14S-dihydroxy-8E,10E,12Z,16Z,19Z-docosapentaenoic acid | 1 triene |

* DPA n-3 refers to SPMs derived from docosapentaenoic acid wherein the terminal carbon-carbon double bond is in the omega three-position.

Salts

The SPM component of an SPM-cyclodextin complex described herein may be a salt of the SPM molecule. In embodiments, the salt of the SPM molecule may be a pharmaceutically acceptable base addition salt, including salts with basic organic or inorganic moieties; or a salt described by Formula I, or the dipeptide and polypeptide salts described in WO2017210604 or WO2019108605

Base Addition Salt

In embodiments, an SPM salt consisting of a pharmaceutically acceptable base addition salt is prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred organic salts derived from organic bases. They include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are lysine, isopropylamine, diethylamine, ethanolamine, trimethylamine, dicyclohexylamine, choline and caffeine.

In embodiments, the SPM salt is described by Formula I, and contains two molecules of the same SPM ionically bound to two basic functions provided by a scaffold as described in Formula I, wherein the scaffold is a divalent metal-amino acid chelate or divalent metal-peptide chelate. In general, the carboxylic acid moiety of the SPM molecule or molecules forming the SPM component is deprotonated to form an ionic bond with a basic function (or functions) of the scaffold portion of the compound. These scaffolds and their SPM salts are described in WO2017210604 and WO2019108605. SPMs that may form the SPM component of a salt of Formula I in accordance with the present invention are given in Table 1. It is understood that the neutral compounds described in the table may become charged (i.e., deprotonated) if solvated at the appropriate pH, and form the anion component described in a compound of Formula I. The compounds represented by Formula I each contain two SPM molecules, which may be referred to herein as the "SPM component" of the compound, and a scaffold portion to which the SPM component is ionically bound. The terms "bis" refer to two (bis) SPM molecules in the salt compound. In embodiments, the two SPM molecules are the same and are selected from RvE1, RvE2, RvE3, RvE4, AT-RvE1, AT-RvE2, AT-RvE3, RvD1, RvD2, RvD3, RvD4, RvD5, RvD6, AT-RvD1, AT-RvD2, AT-RvD3. AT-RvD4, AT-RvD5, AT-RvD6, RvT1, RvT2, RvT3, RvT4. LXA4, LXB4, AT-LXA4, AT-LXB4, PD1, PDX, AT-PD1, MaR1, and MaR2, PD1n-3 DPA or MaR1n-3 DPA.

The abbreviations used herein have their conventional meaning within the chemical and biological arts. The chemical structures and formulae set forth herein are constructed according to the standard rules of chemical valency known in the chemical arts. For example, in instances where a substituents such as —NH3 are shown without a charge, it is understood to possess a formal charge, i.e. NH3+.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., C1-C10 means one to ten carbons).

The term "basic function" refers to a positively charged or protonated primary amine, a positively charged secondary amine, a positively charged tertiary amine, or a positively charged guanidine. In embodiments, basic function refers to —NH3+, —NHC(NH2+)NH2, —NHR6R7, —NR6R7R8, wherein R6, R7, and R8 are each independently hydrogen, —CN, —COOH, —CONH2, unsubstituted alkyl, unsubstituted heteroalkyl, unsubstituted cycloalkyl, unsubstituted heterocycloalkyl, unsubstituted aryl, or unsubstituted heteroaryl; R6 and R7 substituents bonded to the same nitrogen atom may optionally be joined to form a unsubstituted heterocycloalkyl or unsubstituted heteroaryl. In embodiments, the basic function is a hydrogen bond acceptor. In embodiments, the basic function is a positively charged amine.

It is understood that due to resonance a charge may be distributed across the molecule. The chemical structures and formulae set forth herein are constructed according to the standard rules of chemical valency known in the chemical arts, and as such one of skill in the art would recognize the equivalency of the moieties possessing resonance structures.

In embodiments, the "side chain of an amino acid" or "side chain" or "side-chain" as used herein is used in accordance with its ordinary meaning and refers to the functional substituent contained on naturally occurring amino acids. Naturally occurring amino acids are those encoded by the genetic code (e.g. alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine), as well as those amino acids that are later modified, e.g., hydroxyproline, gamma-carboxyglutamate, and O-phosphoserine. In embodiments, the side chain of an amino acid is ionized (e.g., it has a formal charge).

In embodiments, the side chain is selected from the group consisting of H,

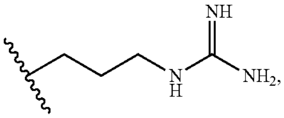, 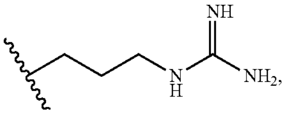, 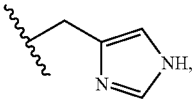, 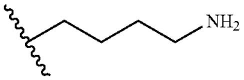, 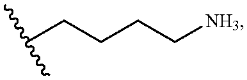, 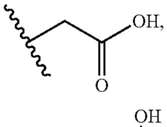, 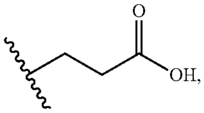, 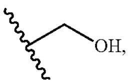, 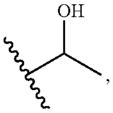, 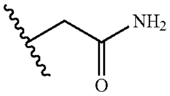, 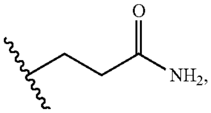, 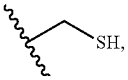, 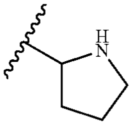, 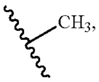, 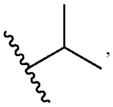, 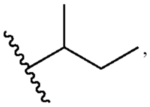, 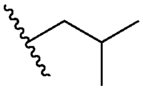, 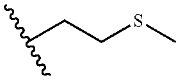, 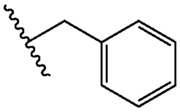, 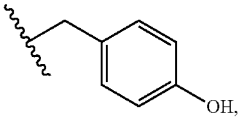 or 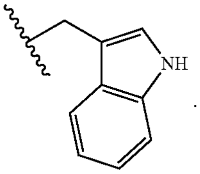.

In embodiments, the side chain is H. In embodiments, the side chain is

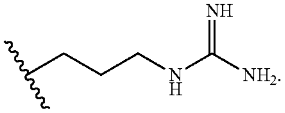 [SMILES: *CCCNC(=N)N]

In embodiments, the side chain is

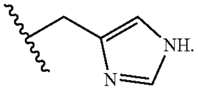 [SMILES: *Cc1c[nH]cn1]

In embodiments, the side chain is

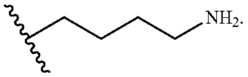 [SMILES: *CCCCN]

In embodiments, the side chain is

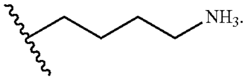

In embodiments, the side chain is

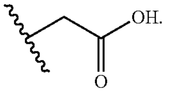 [SMILES: *CC(=O)O]

In embodiments, the side chain is

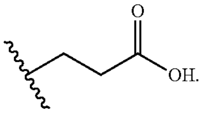

In embodiments, the side chain is

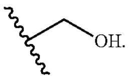 [SMILES: *CO]

In embodiments, the side chain is

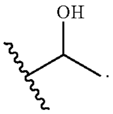 [SMILES: *C(C)O ; "."]

In embodiments, the side chain is

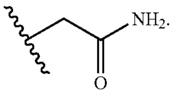 [SMILES: *CC(N)=O]

In embodiments, the side chain is

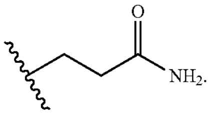 [SMILES: *CCC(N)=O]

In embodiments, the side chain is

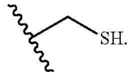 [SMILES: *CS]

In embodiments, the side chain is

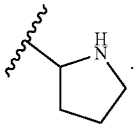 [SMILES: *C1CCCN1]

In embodiments, the side chain may optionally be joined to an adjacent nitrogen to form a unsubstituted heterocycloalkyl (e.g., pyyrolidinyl).

In embodiments, the side chain is

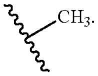

In embodiments, the side chain is

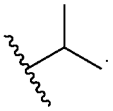 [SMILES: *C(C)C]

In embodiments, the side chain is

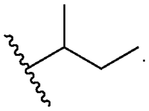 [SMILES: *C(C)CC]

In embodiments, the side chain is

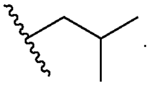 [SMILES: *CC(C)C]

In embodiments, the side chain is

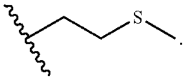 [SMILES: *CCSC]

In embodiments, the side chain is

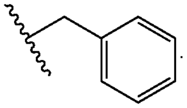 [SMILES: *Cc1ccccc1]

In embodiments, the side chain is

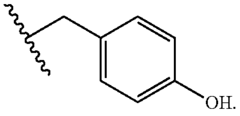 [SMILES: *Cc1ccc(O)cc1]

In embodiments, the side chain is

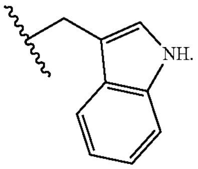 [SMILES: *Cc1c[nH]c2ccccc12]

The side chain of glycine is H. The side chain of arginine is

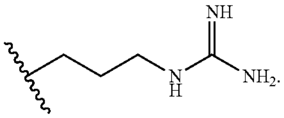 [SMILES: *CCCNC(=N)N]

The side chain of histidine is

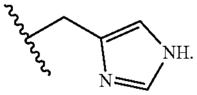 [SMILES: *Cc1c[nH]cn1]

The side chain of lysine is

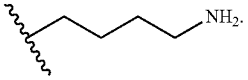 [SMILES: *CCCCN]

The side chain of aspartic acid is

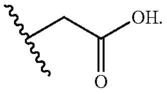 [SMILES: *CC(=O)O]

The side chain of glutamic acid is

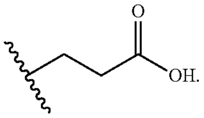 [SMILES: *CCC(=O)O]

The side chain of serine is

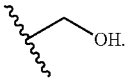 [SMILES: *CO]

The side chain of threonine is

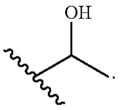 [SMILES: *C(C)O]

The side chain of asparagine is

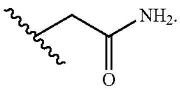

The side chain of glutamine is

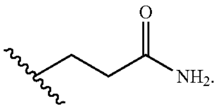 [SMILES: *CCC(N)=O]

The side chain of cysteine is

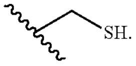

The side chain of proline is

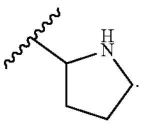 [SMILES: *C1CCCN1]

The side chain of alanine is

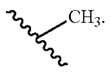

The side chain of valine is

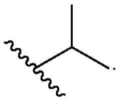 [SMILES: *C(C)C]

The side chain of isoleucine is

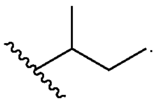 [SMILES: *C(C)CC]

The side chain of leucine is

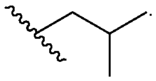 [SMILES: *CC(C)C]

The side chain of methionine is

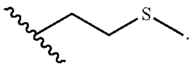

The side chain of phenylalanine is

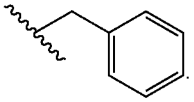 [SMILES: *Cc1ccccc1]

The side chain of tyrosine is

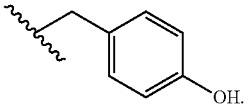 [SMILES: *Cc1ccc(O)cc1]

The side chain of tryptophan is

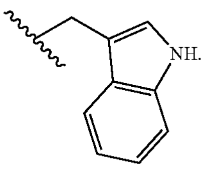 [SMILES: *Cc1c[nH]c2ccccc12]

The term “non-natural amino acid side-chain” refers to the functional substituent of compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium, allylalanine, 2-aminoisobutyric acid. Non-natural amino acids are non-proteinogenic amino acids that either occur naturally or are chemically synthesized. Such analogs have modified R groups (e.g., norleucine) or modified peptide backbones, but retain the same basic chemical structure as a naturally occurring amino acid. Non-limiting examples include exo-cis-3-Aminobicyclo[2.2.1]hept-5-ene-2-carboxylic acid hydrochloride, cis-2-Aminocycloheptanecarboxylic acid hydrochloride, cis-6-Amino-3-cyclohexene-1-carboxylic acid hydrochloride, cis-2-Amino-2-methylcyclohexanecarboxylic acid hydrochloride, cis-2-Amino-2-methylcyclopentanecarboxylic acid hydrochloride,2-(Boc-aminomethyl)benzoic acid, 2-(Boc-amino)octanedioic acid, Boc-4,5-dehydro-Leu-OH (dicyclohexylammonium), Boc-4-(Fmoc-amino)-L-phenylalanine, Boc-beta-Homopyr-OH, Boc-(2-indanyl)-Gly-OH, 4-Boc-3-morpholineacetic acid, 4-Boc-3-morpholineacetic acid, Boc-pentafluoro-D-phenylalanine, Boc-pentafluoro-L-phenylalanine, Boc-Phe (2-Br)—OH, Boc-Phe (4-Br)—OH, Boc-D-Phe (4-Br)—OH, Boc-D-Phe (3-Cl)—OH, Boc-Phe (4-NH2)-OH, Boc-Phe (3-NO2)-OH, Boc-Phe (3,5-F2)-OH, 2-(4-Boc-piperazino)-2-(3,4-dimethoxyphenyl) acetic acid purum, 2-(4-Boc-piperazino)-2-(2-fluorophenyl) acetic acid purum, 2-(4-Boc-piperazino)-2-(3-fluorophenyl) acetic acid purum, 2-(4-Boc-piperazino)-2-(4-fluorophenyl) acetic acid purum, 2-(4-Boc-piperazino)-2-(4-methoxyphenyl) acetic acid purum, 2-(4-Boc-piperazino)-2-phenylacetic acid purum, 2-(4-Boc-piperazino)-2-(3-pyridyl) acetic acid purum, 2-(4-Boc-piperazino)-2-[4-(trifluoromethyl)phenyl] acetic acid purum, Boc-beta-(2-quinolyl)-Ala-OH, N-Boc-1,2,3,6-tetrahydro-2-pyridinecarboxylic acid, Boc-beta-(4-thiazolyl)-Ala-OH, Boc-beta-(2-thienyl)-D-Ala-OH, Fmoc-N-(4-Boc-aminobutyl)-Gly-OH, Fmoc-N-(2-Boc-aminoethyl)-Gly-OH, Fmoc-N-(2,4-dimethoxybenzyl)-Gly-OH, Fmoc-(2-indanyl)-Gly-OH, Fmoc-pentafluoro-L-phenylalanine, Fmoc-Pen(Trt)-OH, Fmoc-Phe (2-Br)—OH, Fmoc-Phe (4-Br)—OH, Fmoc-Phe (3,5-F2)-OH, Fmoc-beta-(4-thiazolyl)-Ala-OH, Fmoc-beta-(2-thienyl)-Ala-OH, 4-(Hydroxymethyl)-D-phenylalanine.

Formula I Compounds

In embodiments, the disclosure provides compounds of Formula I:

(Formula I)

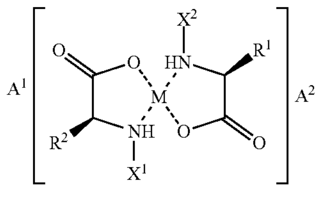

wherein

M is a divalent metal;

A1 and A2 are each the same SPM anion;

R1 and R2 are each independently a C1-C10 alkyl comprising at least one basic function;

X1 and X2 are each independently H or CO—Z and Z is a peptide comprising 1 to 5 amino acids or a pharmaceutically acceptable salt thereof.

Compounds of Formula I have two amino acid moieties coordinated around a divalent metal cation as the amino acid component and two SPM molecules. In embodiments, the divalent metal cation is Mg2+, Ca2+, Mn2+, Fe2+, Cu2+, Co2+, Ni2+, Mo2+ or Zn2+. In embodiments, the divalent metal cation is Mg2+. In embodiments, the divalent metal cation is Ca2+. In embodiments, the divalent metal cation is Zn2+.

In embodiments, the amino acid component includes or consists of lysine or arginine. In embodiments, the amino acid component includes lysine or arginine. In embodiments, the basic function of R1 and R2 is selected from a primary amine, a secondary amine, a tertiary amine, and a guanidine. In embodiments, basic function refers to —NH3, —NHC(NH2+)NH2, —NHR6R7, or —NR6R7R8, wherein R6, R7, R8 are each independently hydrogen, —CN, —COOH, —CONH2, unsubstituted alkyl, unsubstituted heteroalkyl, unsubstituted cycloalkyl, unsubstituted heterocycloalkyl, unsubstituted aryl, or unsubstituted heteroaryl; R6 and R7 substituents bonded to the same nitrogen atom may optionally be joined to form an unsubstituted heterocycloalkyl or unsubstituted heteroaryl. In embodiments, the basic function is a hydrogen bond acceptor. In embodiments, the basic function is a hydrogen bond donor. In embodiments, the basic function is a positively charged amine.

In embodiments, R1 and R2 are each the side chain of an amino acid residue having a basic function. In embodiments, R1 and R2 are the same and the amino acid residue is lysine or arginine.

In embodiments, R1 and R2 are independently selected from —(CH2) 3-Y1, and —(CH2) 4-Y2, where Y1 and Y2 are each a basic function which may be the same or different. In embodiments, R1 is —CH2CH2NH3. In embodiments, R2 is —CH2CH2NH3. In embodiments, R1 is —CH2CH2CH2CH2NH3. In embodiments, R2 is —CH2CH2CH2CH2NH3.

In embodiments, R1 and R2 are both-(CH2) 4-Y2, and Y2 is —NH3+.

In embodiments, R1 and R2 are both-(CH2) 3-Y1, and Y1 is —NHC(NH2+)NH2.

In embodiments, R1 is —(CH2) 3-Y1, Y1 is —NHC (NH2+)NH2, Y2 is —(CH2) 4-Y2, and Y2 is —NH3+. In embodiments, R1 is —(CH2) 4-Y2, Y2 is —NH3+, R2 is —(CH2) 3-Y1, and Y1 is NHC(NH2+)NH2.

In embodiments, X1 and X2 are the same and are hydrogen (H). In embodiments, X1 is hydrogen. In embodiments, X2 is hydrogen.

In an embodiment of the compound of Formula I, A1 and A2 are selected from RvE1, RvE2, RvE3, RvE4, AT-RvE1, AT-RvE2, AT-RvE3, RvD1, RvD2, RvD3, RvD4, RvD5, RvD6, AT-RvD1, AT-RvD2, AT-RvD3. AT-RvD4, AT-RvD5, AT-RvD6, RvT1, RvT2, RvT3, RvT4. LxA4, LxB4, AT-LxA4, AT-LxB4, PD1, PDX, AT-PD1, MaR1, and MaR2, PD1n-3 DPA or MaR1n-3 DPA; M is Mg2+, Ca2+, or Zn2+, R1 and R2 are both-(CH2) 4-Y2 and Y2 is NH3+; and X1 and X2 are H. This selection of R1, R2, and Y2 may be referred to herein as the metal "di-lysinate", e.g., "magnesium di-lysinate" or "Mg-di-lysinate". In this embodiment, the peptide component consists of a lysine dipeptide.

In an embodiment of the compound of Formula I, A1 and A2 are the same and selected from an E series Resolvin. In embodiments, the E series Resolvin is selected from RvE1, RvE2, RvE3, RvE4, AT-RvE1, AT-RvE2, and AT-RvE3, M is Mg2+, Ca2+, or Zn2+, R1 and R2 are both-(CH2) 4-Y2 and Y2 is NH3+; and X1 and X2 are H. This selection of R1, R2, and Y2 may be referred to herein as the metal "di-lysinate", e.g., "magnesium di-lysinate" or "Mg-di-lysinate".

In an embodiment of the compound of Formula I, A1 and A2 are the same and selected from a D series Resolvin. In embodiments, the D series Resolvin is selected from RvD1, RvD2, RvD3, RvD4, RvD5, RvD6, AT-RvD1, AT-RvD2, AT-RvD3, AT-RvD4, AT-RvD5, AT-RvD6, M is Mg2+, Ca2+, or Zn2+, R1 and R2 are both (CH2) 4 Y2 and Y2 is NH3+; and X1 and X2 are H. This selection of R1, R2, and Y2 may be referred to herein as the metal "di-lysinate", e.g., "magnesium di-lysinate" or "Mg-di-lysinate".

In an embodiment of the compound of Formula I, A1 and A2 are the same and selected from LxA4 or AT-LxA4, M is Mg2+, Ca2+, or Zn2+, R1 and R2 are both-(CH2) 4-Y2 and Y2 is NH3+; and X1 and X2 are H. This selection of R1, R2, and Y2 may be referred to herein as the metal "di-lysinate", e.g., "magnesium di-lysinate" or "Mg-di-lysinate".

Physical Properties

The complexes described here and compositions comprising same possess advantageous chemical and physical properties compared to the free SPMs and salts, esters, or amides thereof. For example, in embodiments the SPM component of a complex described here may be stabilized against chemical degradation, as a solid or as a solution in deionized water, compared to the corresponding free SPM or SPM salt, ester, or amide under accelerated conditions of 40° C., 75% relative humidity, and exposed to air. In embodiments, the complexes are stable against chemical degradation, including oxidative degradation. In embodiments, the complexes are stabilized against degradation induced by exposure to air, oxygen, and humidity as evidenced by a relative lack of change in physical properties, such as flow characteristics, and/or in chemical properties, as measured, for example, by spectroscopic techniques such as nuclear magnetic resonance (NMR) or high pressure liquid chromatography (HPLC). In embodiments, the increased stability is evidenced by a relative lack of chemical degradation at 8 or 16 or 24 weeks compared to the SPM in the form of sodium salt or a mineral amino acid chelate salt. In embodiments, the SPM component of a complex described here is stabilized against chemical degradation as evidenced by significantly reduced degradation products at 8 or 16 or 24 weeks, compared to the SPM in the form of a salt or ester thereof.

In embodiments, the complexes are physically solid, free flowing substances suitable for formulation into solid dosage forms such as powders, tablets, capsules, film, or caplets, and into parenteral dosage forms such as solutions, suspensions, emulsions, and dry powders for reconstitution. For example, in embodiments, the complexes maintain their form as a solid, free flowing substance for up to 168 hours, with no visible changes when exposed to air at temperatures between 18 to 22° C. and relative humidity between 50% to 75%, compared to the corresponding free SPM or SPM salt, ester, or amide, which turns from a brown/orange powder into a gel-like or oil-lie substance within 24 hours. In embodiments, the complexes can be blended with standard pharmaceutical excipients such as fillers, gliding agents, disintegrants and lubricants with flow properties that are suitable for gravity feed in a rotary press. For example, in embodiments, when the complexes are blended with a standard mixture of pharmaceutical excipients in a ratio of approximately 1 to 4.3 (weight/weight), without further dry or wet milling (i.e., granulation), the resulting blend has a particle size distribution with flow characteristics that are suitable for compression by a gravity-fed rotary press. In embodiments, the core tablets produced using the aforementioned blend of 1 to 4.3, using a gravity-fed rotary press, with tablet hardness between 18 kilopond and 30 kilopond, have friability and disintegration properties that are consistent with a specification considered suitable for an immediate release oral dosage form or for enteric coating as a delayed-release oral dosage form. In addition, the complexes and compositions of the invention can be readily combined, Pharmaceutical Compositions The present disclosure provides pharmaceutical compositions comprising an SPM, such as a resolvin, protectin, lipoxin, or maresin, or a salt thereof, or an ester, or amide thereof, complexed with a cyclodextrin. In embodiments, the salt of the SPM may be a simple salt, such as a sodium, potassium, calcium, zinc, or magnesium salt, any other pharmaceutically acceptable base addition salt or a salt described by Formula I.

A pharmaceutical composition as described herein may be formulated for any suitable route of administration, for example, oral, pulmonary, rectal, parenteral, transdermal, subcutaneous, intravenous, intramuscular, intraperitoneal, inhalational, buccal, sublingual, intrapleural, intrathecal, intranasal, vaginal, and the like. Dosage forms for the topical or transdermal administration of a compound of this invention include powders, sprays, ointments, pastes, creams, lotions, gels, solutions, patches and inhalants.

In embodiments, the pharmaceutical composition is formulated as a parenteral dosage form such as a sterile aqueous solution or dispersion suitable for parenteral administration. In embodiments, the parenteral dosage form is selected from an intravenous dosage form, an intra-arterial dosage form, or an intramuscular dosage form. In embodiments, the dosage form is suitable for administration by a subcutaneous route.

In embodiments, the pharmaceutical composition is in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof.

In accordance with any of these embodiments, the dosage form may be in the form of a clear aqueous solution, which may optionally be frozen, or in the form of a lyophilized solid, preferably a sterile lyophilized solid e.g., contained in container, such as a pre-filled syringe, vial or ampule. In some embodiments, the container contains lyophilized composition and is suitable for reconstitution with a specified amount of sterile water, aqueous buffer, or other commonly used parenteral diluent, e.g., 5% dextrose solution, normal saline solution, etc., for administration by a parenteral route, e.g., intravenous, intra-arterial, or an intramuscular, subcutaneous.

In embodiments, the pharmaceutical composition is formulated as an oral or peroral dosage form. In embodiments, the oral formulation is in the form of e.g., a tablet, capsule, powder, solution, suspension, or emulsion.

In embodiments, the pharmaceutical composition is formulated as a sublingual dosage form. In embodiments, the sublingual formulation is in the form of a tablet, film or spray.

In embodiments, the pharmaceutical composition is formulated for administration via inhalation through the nose or mouth. In embodiments, the inhalable dosage form is a liquid formulation, such as an aqueous solution formulation adapted for pulmonary delivery via a nebulizer, including jet, vibrating mesh, and static mesh or orifice nebulizers. In embodiments, the inhalable dosage form is a dry powder for inhalation (DPI). In embodiments, the inhalable dosage form is a propellant-based aerosol formulation suitable for administration using a metered dose inhaler (MDI).

In embodiments, a pharmaceutical composition comprising a SPM complex is in the form of a unit dose of the SPM in the complex. In embodiments, the unit dosage form is a sterile, freeze-dried composition in a suitable container, such as an ampule or vial. The term "freeze-dried" is synonymous with the term "lyophilized" in this context. In embodiments, the unit dose contains from 0.5 microgram (ug) to 100 milligrams (mg) of the SPM active moiety. In embodiments, the unit dose contains 1, 25, 50, 100, 250, or 500 micrograms of the SPM active moiety. In embodiments, the unit dose contains 1, 2, 3 or 5 milligrams of the SPM active moiety or multiples thereof between 1 and 100 milligrams.

The compositions described here may be formulated using one or more suitable excipients or carriers. A suitable excipient or carrier is one suitable for human or animal use. The term "excipient" refers to an additive that serves some purpose in the composition other than a carrier, for example as a stabilizer, solubilizing agent, bulking agent, compression aid, flow modifier, lubricant, disintegrant, or suspending agent. Often, a carrier will serve a dual purpose as a simple carrier or diluent and an excipient. Examples of pharmaceutically acceptable excipients may thus include carriers. Non-limiting examples of excipients for use in the compositions of the invention include sterile liquids, water, buffered saline, ethanol, polyols (for example, glycerol, propylene glycol, polyethylene glycol and the like), oils, detergents, suspending agents, carbohydrates (e.g., glucose, lactose, sucrose or dextran), antioxidants (e.g., ascorbic acid or glutathione), chelating agents, low molecular weight peptides, and suitable mixtures thereof.

A suitable excipient or carrier is typically a pharmaceutically acceptable carrier or excipient for use in humans or animals. The term "pharmaceutically acceptable" indicates approval by a regulatory agency of the Federal or a state government or listed in the U.S. Pharmacopeia or other generally recognized pharmacopeia such as the European Pharmacopeia, for use in animals, and more particularly in humans. In the context of the pharmaceutical compositions of the invention, a "carrier" refers to, for example, a solvent, a diluent, or vehicle with which the complexes of the invention are formulated for delivery. Examples of pharmaceutically acceptable carriers for use in the compositions of the invention include, without limitation, sterile aqueous and non-aqueous liquids, water, buffered saline, ethanol, polyols (for example, glycerol, propylene glycol, liquid polyethylene glycol and the like), and oils, for liquid dosage forms; or carbohydrates (e.g., glucose, lactose, sucrose or dextran) for solid dosage forms.

The disclosure also provides packaging and kits comprising pharmaceutical compositions for use in the methods of the present invention. The kit can comprise one or more containers selected from the group consisting of a bottle, a vial, an ampule, a blister pack, infusion pump, and a syringe. The kit can further include one or more of instructions for use, one or more syringes, one or more applicators, or a sterile solution suitable for reconstituting a pharmaceutical composition of the present invention.

In embodiments, the pharmaceutical composition is a solid dosage form comprising a SPM complex blended with one or more excipients or carriers. The blend of the SPM complex and the excipients may be filled directly into capsules or compressed into tablets, with or without prior granulation of the blend. In embodiments, the SPM complex and the excipients are present in a weight-to-weight ratio ranging from 10:1 to 1:5, or optionally 5:1 to 1:3, or 3:1 to 1:2, or 2:1 to 1:1.5.

Methods of Preparing Complexes

The present invention provides methods for complexation of a cyclodextrin with an SPM, or its salt, comprising dissolution of the SPM, or its salt, and the cyclodextrin in aqueous solution, which may be, for example, water, or an organic solvent/water mixture. In accordance with the methods described here, the pH of the aqueous solution is preferably between 5 and 9. The resulting complexes are isolated by removal of the aqueous solvent, for example by one or more techniques such as crystallization (Loftsson T, et al., J Pharm Pharmacol. 2016; 68 (5): 544-555), or by using a drying technique, such as co-evaporation under reduced pressure, spray drying, or freeze-drying (Desai N. S., et al., J. Incl. Phenom. Macrocycl. Chem. 2011; 70:217-225; Maestrelli F, et al., Eur J Pharm Biopharm. 2011 August; 78 (3): 385-93; Jablan J, et al., J Pharm Biomed Anal. 2012 December; 71:35-44; Bragagni M., et al., J. Incl. Phenom. Macrocycl. Chem. 2010; 68:437-445; Jug M, et al., Drug Dev Ind Pharm. 2009 July; 35 (7): 796-807; Promzeleva M., et al., ACS Biomater. Sci. Eng. 2018; 4:491-501).

Pharmaceutical Uses

The inflammatory response in humans has two phases: initiation and resolution.

At the cellular level, initiation is a protective response characterized by the production and release of pro-inflammatory mediators to activate the innate immune response, resulting in an influx of polymorphonuclear cells (PMNs) from blood to kill and clear foreign invaders and damaged cells. This initiation phase is an active process driven by metabolites of arachidonic acid including the prostaglandins, which are chemo-attractants for eosinophils, neutrophils and monocytes, and the leukotrienes, which elicit adhesion, chemotaxis, and aggregation of leukocytes.

During the peak of inflammation, as the inflammatory stimulus is being reduced, the resolution phase begins, marked by a reduction of pro-inflammatory signals and a switch from the production and release of pro-inflammatory mediators to the production and release of SPMs, including resolvins, protectins, lipoxins, and maresins. SPMs activate and coordinate the resolution phase by halting PMN infiltration and stimulating the recruitment and activation of monocytes and pro-resolving macrophages to clear the tissue of cellular debris in a non-phlogistic manner, enabling the return to tissue homeostasis (Serhan et al., Cold Spring Harb Perspect Biol 2015; 7:a016311).

Unresolved inflammation is widely recognized as a unifying aspect of many chronic diseases and disorders. Accordingly, the ability to resolve excessive inflammation is of paramount importance to human health (Serhan, C. N., Nature 2014 510:92-101; Coussens et al. Nature 2002; 420, 860-867, Grivennikov et al., Cell. 2010; 140 (6):883-99, Todoric et al., Cancer Prev Res. 2016; 9 (12):895-905; Fishbein et al., Pharmacol Ther. 2021; 218:107670).

Researchers have demonstrated efficacy of SPMs in preventing and/or treating disease in numerous preclinical models, including those relating to Alzheimer's disease, burn wounds, chronic pancreatitis, diabetic wounds, dermatitis, pulmonary inflammation, peripheral nerve injury, obesity, allergic airway response, amyotrophic lateral sclerosis, acute lung injury, fibrosis, bacterial infection, peritonitis, dry eye, tissue regeneration, pain, adipose tissue inflammation, localized aggressive periodontitis, colitis, temporomandibular joint inflammation, arthritis, postoperative pain, postsurgical cognitive decline, endotoxin shock, HSV-keratitis, allograft rejection, heart ischemia, bacterial pneumonia, cigarette smoke-induced lung inflammation, vascular inflammation, fibromyalgia, and vagotomy (Serhan C N, et al., Cold Spring Harb Perspect Biol 2015; 7:016311).

Lim et al. describes the analgesic potency of SPMs in a large number of inflammatory pain models and characterizes resolvins and related substances as therapeutic candidates for preventing deterioration of inflammation and pathologic pain (Lim J Y, et al., BioMed Research International 2015, pp. 1-14). Lim also notes that "the powerful potencies" and "negligible adverse effects" of these molecules make them attractive candidates for clinical use.

U.S. Pat. Nos. 8,008,282 and 6,627,658 describe lipoxin analogs and their use as inhibitors of angiogenesis. U.S. Pat. Nos. 5,441,951, 5,648,512, 6,048,897, 6,316,648, 6,569,075, 6,887,901, 7,288,569, and 7,294,728, 7,741,369, and 7,741,369 describe lipoxin compounds and their use in treating cell proliferative disorders. U.S. Pat. No. 8,119,691 describes lipoxins and aspirin triggered lipoxins and their analogs in the treatment of asthma and inflammatory airway disease.

US20060293288 describes the use of resolvins to treat gastrointestinal inflammation and diseases such as ulcerative colitis, Crohn's disease, infectious enteritis, antibiotic associative diarrhea, *Clostridium difficile* colitis, microscopic or lymphocytic colitis, collagenous colitis, colon polyps, familial polyps, familial polyposis syndrome, Gardner's Syndrome, *Helicobacter pylori*, irritable bowel syndrome, nonspecific diarrheal illnesses, and intestinal cancers. U.S. Pat. Nos. 6,670,396, 7,053,230, 7,378,444, 7,585,856, 7,595,341, 7,709,669, 7,737,178, 8,349,896, 8,461,201, 8,569,542 and 8,853,437 describe resolvins and their use in methods for treating inflammatory, angio-proliferative, cardiovascular, thrombophlebotic, vascular, ocular, dermatologic, neurodegenerative, pulmonary, endocrine, reproductive, rheumatologic and gastrointestinal diseases, for example where the inflammation manifests as Crohn's disease, ulcerative colitis, distal proctitis, rheumatoid spondylitis, arthritis, rheumatoid arthritis, osteoarthritis, gouty arthritis, psoriasis, dermatitis, eczematous dermatitis, atopic or seborrheic dermatitis, allergic or irritant contact dermatitis, eczema craquelee, photoallergic dermatitis, phototoxic dermatitis, phytophotodermatitis, radiation dermatitis, stasis dermatitis, arterial inflammation, coronary infarct damage, restenosis, uveitis, iritis, conjunctivitis, adult respiratory distress syndrome, bronchitis, cystic fibrosis, a spasmogenic condition, asthma, idiopathic bronchial asthma, arterial smooth muscle constriction, coronary spasm, myocardial infarction, ischemia-induced myocardial injury, cerebral spasm, stroke, inflammatory bowel disorder, spastic colon, mucous colitis, an allergic condition, eczema, an allergic bowel disease, coeliac disease, an allergic eye condition, hay fever, allergic rhinitis, allergic conjunctivitis, a condition involving blood platelet aggregation, coronary thrombosis, phlebitis, or phlebothrombosis, and methods of treating cardiovascular disease.

US20120245229 describes resolvins and methods of treating neuropathic pain, including pain associated with diabetic neuropathy or HIV infection, methods of treating postoperative pain, inflammatory pain, pain associated with cancer, and pain associated with fibromyalgia, by administering resolvins.

U.S. Pat. No. 10,233,167 describes maresins and methods of treating or preventing inflammation associated with neurodegeneration, memory loss, wrinkles, psoriasis, dandruff, dermatitis, arterial inflammation, arthritis, psoriasis, urticaria, vasculitis, asthma, ocular inflammation, pulmonary inflammation, pulmonary fibrosis, seborrheic dermatitis, pustular dermatosis, AIDS, allergic responses, Alzheimer's disease, inflammatory diseases, atherosclerosis, bone diseases, breast cancer, cancer, cardiovascular diseases, colon cancer, congenital defects, degenerative neurologic disorders, dementia, dermatology disorders, diabetes mellitus, endocrine disorders, eye diseases, gastrointestinal disorders, genitourinary disorders, hearing disorders, hematologic disorders, hepatobiliary disorders, hypertension, immunologic disorders, infectious diseases, leukemia/lymphoma, lung cancer, metabolic disorders, neonatology, neurological disorders, neuromuscular disorders, obesity/eating disorders, orthopedic disorders, parasitic diseases, perinatal disorders, prostate cancer, psychiatric disorders, pulmonary disorders, renal disorders, reproduction disorders, rheumatic diseases, stroke, surgical transplantation disorders, vascular disorders, oral infections, periodontal diseases, brain injury, trauma and neuronal inflammation.

US20200010398 and US20200048177 describe novel mono-hydroxy, di-hydroxy and tri-hydroxy derived from docosapentaenoic acid and methods to treat or prevent inflammation associated with arterial inflammation, arthritis, psoriasis, urticara, vasculitis, asthma, ocular inflammation, pulmonary inflammation, pulmonary fibrosis, seborrheic dermatitis, pustular dermatosis, cardiovascular diseases, recruitment of neutrophils, leukocytes and/or cytokines, addiction, AIDS, alcohol-related disorders, allergy, Alzheimer's disease, arthritis, asthma, atherosclerosis, bone diseases, breast cancer, cancer, cardiovascular diseases, colon cancer, congenital defects, decision analysis, degenerative neurologic disorders, dementia, dermatology, diabetes mellitus, endocrine disorders, eye diseases, fetal and maternal medicine, gastrointestinal disorders, gene therapy, genetic diagnostics, genetics, genitourinary disorders, geriatric medicine, growth and development, hearing, hematologic disorders, hepatobiliary disorders, hypertension, infectious diseases, leukemia, lymphoma, lung cancer, metabolic disorders, neonatology, neurological disorders, neuromuscular disorders, obesity, orthopedic, parasitic diseases, perinatal disorders, pregnancy, prostate cancer, psychiatric disorders, pulmonary disorders, renal disorders, reproduction, rheumatic diseases, stroke, surgery, transplantation, vaccines, vascular medicine, wounds, oral infections, periodontal disease, brain injury, trauma and neuronal inflammation.

U.S. Pat. Nos. 8,273,792, 9,364,454 and 9,782,379 describes protectins, including Protectin D1 and Protectin DX, and methods of treating or preventing airway inflammation as well regulating blood glucose and suppressing lipid-induced inflammation and other related inflammatory conditions such as insulin resistance, metabolic syndrome, type-2 diabetes, hypertension and cardiovascular diseases.

In embodiments, the present invention provides methods of treating a disease or disorder amendable to therapy with SPMs, including cancer, gastrointestinal diseases and disorders, inflammatory disorders, infectious diseases and disorders, metabolic diseases and disorders, neurological disorders, and pulmonary diseases and disorders. In embodiments, the methods comprise administering to the subject in need of such therapy a pharmaceutical composition containing a complex of an SPM and a cyclodextrin as described herein, wherein the complex comprises an amount of an SPM effective to treat the disease or disorder. In the context of the methods described here, the term "treating" refers to the regression, stabilization, or reduced progression of the disease or disorder being treated, or the amelioration or stabilization of one or more clinical symptoms associated with the disease or disorder being treated.

Cancer

The present disclosure provides methods for treating cancer in a subject in need of such treatment, the methods comprising administering to the subject a pharmaceutical composition containing a complex as described herein, wherein the complex comprises an amount of an SPM effective to treat the cancer.

In accordance with the methods described here, administration may be alone as monotherapy, or in combination therapy with one or more additional therapeutic agents. In embodiments, the combination therapy is an adjunctive therapy, for example as an adjunct to chemotherapy, targeted therapy, immunotherapy, hormone therapy, gene therapy, or microbiome therapy. In embodiments, the combination therapy is an immune checkpoint inhibitor therapy. In embodiments, the combination therapy is an adjuvant or neoadjuvant therapy to surgery or radiation therapy. In embodiments, the composition may be administered as first line, second line, third line or palliative therapy, alone or in combination with other therapies, for example, surgery, radiation therapy, chemotherapy, targeted therapy, immunotherapy, hormone therapy, gene therapy, or microbiome therapy. The terms “therapy” and “therapies” refer to any method, protocol and/or agent that can be used in the treatment or management of the cancer.

In the context of the methods described here, the term “treating” may refer to the amelioration or stabilization of one or more clinical symptoms associated with the cancer being treated. In embodiments, treating leads to the elimination of a clinical symptom of the cancer being treated, however, elimination is not required. In embodiments, the severity of the symptom is decreased. In the context of cancer, such symptoms may include clinical markers of severity or progression including size of a solid tumor, amount of growth factors or other biomarkers secreted by a solid tumor, tumor vascularization, tumor metastasis, or number of metastases. Accordingly, treating cancer according to the methods described here can result in a reduction in size or volume of a tumor, also referred to as tumor regression; a decrease in the number of tumors; or a decrease in the number of metastatic lesions in other tissues or organs distant from the primary tumor site. Such symptoms may also include cancer cachexia or pain. Accordingly, treating cancer according to the methods described here can result in a reduction in cancer cachexia or pain, wherein the reduction in cachexia or pain is due to the administration of a complex, as described herein. In embodiments, “treating” cancer according to the methods described here results in increased overall survival and/or increased progression free survival in the subject being treated. In the context of the present disclosure, the term “treating” is not meant to encompass the amelioration or stabilization of clinical symptoms that are not associated with the cancer being treated, and instead, for example, are associated with a treatment modality, such as a side effect or adverse event related to another therapy such as radiation therapy or chemotherapy, unless explicitly stated. In addition, the term “treating” is not intended to encompass prevention, or the administration of an SPM complex prior to diagnosis of a cancer in the subject being treated.

In embodiments, the present invention provides methods for the amelioration of an adverse event or side effect of chemotherapy, targeted therapy, immunotherapy, or radiation therapy, for example, gastrointestinal toxicities such as oral or gastrointestinal mucositis, colitis, enteritis, gastritis, nausea, vomiting, and diarrhea, cardiovascular toxicities such as cardiomyopathy, myocardial ischemia, pericarditis, myocarditis, valvular heart disease, arrhythmia, congestive heart failure, hypertension, coronary, cerebral, and peripheral vascular events, or congestive heart failure, dermatological toxicities such as pruritis or severe rash, hepatotoxicities, pulmonary toxicities such as pulmonary hypertension and pneumonitis, endocrinopathies such as hypothyroidism, hyperthyroidism, and hypophysitis, neurotoxicities such as such as Guillain-Barré syndrome, myasthenia gravis, posterior reversible encephalopathy syndrome, aseptic meningitis, enteric neuropathy, transverse myelitis, pancerebellitis, autoimmune encephalitis, and cranial and peripheral neuropathies, or other side effects such as pancreatitis, acute kidney injury, and cytokine release syndrome, the methods comprising administering a complex as described herein, to a subject that is undergoing or will be undergoing chemotherapy, targeted therapy, immunotherapy, or radiation therapy, wherein the resolvin is effective to mitigate or prevent an adverse event or side effect of the chemotherapy, targeted therapy, immunotherapy, or radiation therapy.

In accordance with the methods described here, a therapeutically effective amount of the SPM complex is administered to the subject in need of therapy. The therapeutically effective amount is an amount or dose of the SPM active moiety sufficient to treat the cancer, or sufficient to achieve a desired therapeutic outcome, for example, the amelioration or stabilization of one or more biomarkers of disease progression or one or more clinical symptoms.

Gastrointestinal Diseases and Disorders

In embodiments, the present disclosure provides a method for treating a gastrointestinal disease or disorder in a subject in need thereof by administering to the subject a pharmaceutical composition containing a complex as described herein, wherein the complex comprises an amount of an SPM effective to treat the gastrointestinal disease or disorder.

In embodiments, gastrointestinal disease or disorder is selected from ulcerative colitis, Crohn’s disease, proctitis, pouchitis, eosinophilic colitis, lymphocytic colitis, collagenous colitis, diversion colitis, chemical colitis, ischemic colitis, infectious colitis, pseudomembranous colitis and indeterminate colitis. In embodiments, the gastrointestinal disease or disorder is selected from ulcerative colitis, and Crohn’s disease.

In embodiments, the gastrointestinal disease or disorder is selected from bowel obstruction, chronic pancreatitis, colitis, colon cancer, congenital gastrointestinal anomalies, gastroschisis, high-output fistula, parenteral nutrition associated liver disease, postoperative ileus, postoperative intestinal inflammation, short bowel syndrome, and sporadic polyposis. In embodiments, the gastrointestinal disease or disorder is selected from eosinophilic esophagitis, Behcet’s disease, irritable bowel syndrome, celiac disease, Intestinal mucositis, NSAID enteropathies, enteric infections, diverticulosis, diverticulitis, gastritis, pancreatitis, viral gastroenteritis, and Whipple’s disease.

In embodiments, the gastrointestinal disease or disorder is postoperative intestinal inflammation, postoperative ileus, or a combination thereof. In embodiments, the gastrointestinal inflammatory disease or disorder is postoperative ileus (POI).

In preferred embodiments, the gastrointestinal disease or disorder is inflammatory bowel disease (referred herein as “IBD”), which is the term given for two conditions, Crohn’s disease and ulcerative colitis, both characterized by chronic inflammation of the gastrointestinal tract. Crohn’s disease may affect any portion of the gastrointestinal tract, including the oral cavity and anus, but most often affects the lower gastrointestinal tract, especially the ileum and/or colon. Ulcerative colitis affects the colon and rectum. The terms “large intestine” and “colon” are used interchangeably in the present disclosure.

Standard of care treatment of mild-to-moderate IBD is aimed at achieving and maintaining remission by controlling inflammation in the target tissues of the gastrointestinal tract. In adults, 5 aminosalicylates (5-ASA), alone or in combination with corticosteroids may be used to induce remission. Generally, corticosteroid treatment is administered for short-term control of symptoms, e.g., to treat acute flare-ups and induce remission of disease symptoms. Longer-term, or maintenance therapy, generally involves the use of non-steroidal agents including 5-ASA, and immune modulators such as azathioprine.

Standard of care treatment of moderate-to-severe IBD is also aimed at achieving and maintaining remission by controlling inflammation in the target tissues of the gastrointestinal tract. In adults, anti-TNF therapy using adalimumab, golimumab, or infliximab alone or in combination with a corticosteroid, thiopurine, or 5-ASA may be used to induce remission. For patients with moderate-to-severe IBD that have failed anti-TNF therapy, an integrin receptor antagonist such as vedolizumab, a Sphingosine-1-phosphate receptor modulators such as ozanimod, or a Janus kinase inhibitor such as tofacitinib may be used. Longer-term, or maintenance therapy, generally involves continuation of anti-TNF therapy, with or without a thiopurine, or continuation of the other therapies described above.

In embodiments, the present disclosure provides for treatment of IBD by administering to the subject a pharmaceutical composition containing a complex as described herein either as monotherapy or in a combination therapy with a second IBD therapeutic agent. In embodiments, the second IBD therapeutic agent is selected from a corticosteroid, 5-ASA, azathioprine, anti-TNF therapy, an integrin receptor antagonist, a Sphingosine-1-phosphate receptor modulator, or a Janus kinase inhibitor. In embodiments, the disclosure provides bis RvE1 magnesium di-lysinate for use in a method of treating IBD in combination with an IBD maintenance therapy, optionally 5-ASA, azathioprine, anti-TNF therapy, integrin receptor antagonist, Sphingosine-1-phosphate receptor modulator, or Janus kinase inhibitor. In embodiments, the disclosure provides bis RvE1 magnesium di-lysinate for use in a method of treating IBD in combination with any one or more of 5-ASA, azathioprine, a corticosteroid, anti-TNF therapy, integrin receptor antagonist, Sphingosine-1-phosphate receptor modulator, or Janus kinase inhibitor. In embodiments, the disclosure provides bis RvE1 magnesium di-lysinate for use in a method of treating IBD in combination with a corticosteroid. In accordance with the foregoing embodiments of combination therapy of bis RvE1 magnesium di-lysinate with a corticosteroid, the corticosteroid may be selected from the group consisting of prednisone, prednisolone, budesonide, hydrocortisone, and beclometasone dipropionate, where the dosage form is an oral dosage form, or from hydrocortisone, prednisolone, and budesonide, where the dosage form is adapted for rectal delivery, for example in the form of an enema or suppository. In accordance with the foregoing embodiments of combination therapy of bis RvF1 magnesium di-lysinate with an anti-TNF therapy, integrin receptor antagonist, Sphingosine-1-phosphate receptor modulator, or Janus kinase inhibitor, the second IBD therapeutic agent may be selected from the group consisting of adalimumab, golimumab, infliximab, vedolizumab, ozanimod, etrasimod, tofacitinib or filgotinib.

Inflammatory Disorders

The compounds described here may be particularly useful in the treatment of diseases and disorders having a significant inflammatory component, due to the ability of the SPMs to mediate resolution of inflammation, and the ability of the compounds described here to deliver therapeutically effective amounts of SPMs to the tissue of a subject in need of treatment for inflammation.

In embodiments, the present disclosure provides a method for treating an inflammatory disease or disorder in a subject a pharmaceutical composition containing a complex as described herein, wherein the complex comprises an amount of an SPM effective to treat the inflammatory disease or disorder.

In embodiments, the inflammatory disease or disorder is selected from the group consisting of acne, adipose tissue inflammation, allograft rejection, arthritis, bacterial infection, burn wounds, chelitis, chronic pancreatitis, corneal wound, dermatitis, diabetic wounds, dry eye syndrome, eczema, endometriosis, endotoxin shock, glossitis, heart ischemia, HSV-keratitis, ischemia reperfusion injury, localized aggressive periodontitis, lyme arthritis, macular edema, oral mucositis, osteoarthritis, periodontitis, peritonitis, post-operative pain, postsurgical cognitive decline, pruritus, psoriasis, pyoderma gangrenosum or hidradenitis suppurativa, retinopathy, rheumatoid arthritis, scleroderma, Sjogren's syndrome, steroid-induced rosacea, stomatitis, systemic inflammatory response syndrome, temporomandibular joint inflammation, and vascular inflammation.

Infectious Diseases and Disorders Caused by an Infectious Agent

In embodiments, the present disclosure provides a method for treating a disease or disorder caused by an infectious agent, such as a bacterium, a fungus, or a virus, in a subject in need thereof by administering to the subject a pharmaceutical composition containing a complex as described herein, wherein the complex comprises an amount of an SPM effective to treat the infectious disease or disorder.

In embodiments, the disease or disorder is a bacterial infection. In embodiments, the bacterial infection is bacterial pneumonia. In embodiments, the bacterial infection is an *E. coli* infection. In embodiments, the bacterial infection is a *Mycobacterium tuberculosis* infection.

In embodiments, the disease or disorder is a yeast infection. In embodiments, the yeast infection is a *Candida* yeast infection.

In embodiments, the disease or disorder is sepsis. In embodiments, the sepsis is burn wound sepsis.

Metabolic Diseases and Disorders

In embodiments, the present disclosure provides a method for treating a metabolic disease or disorder in a human subject in need thereof by administering to the subject a pharmaceutical composition containing a complex as described herein, wherein the complex comprises an amount of an SPM effective to treat the metabolic disease or disorder.

In embodiments, the metabolic disease or disorder is abnormal glucose metabolism manifesting in diabetes, including type 2 diabetes, or pre-diabetes, insulin resistance, abnormal lipid metabolism manifesting as hypertriglyceridemia, i.e., elevated triglycerides, mixed dyslipidemia, hypercholesterolemia, fatty liver, and combined abnormal glucose and lipid metabolism manifesting in obesity; or a dyslipidemic disorder selected from hypertriglyceridemia, hypercholesterolemia and mixed dyslipidemias.

In embodiments, the metabolic disease or disorder is insulin resistance, mixed dyslipidemia, nonalcoholic steatohepatitis (NASH), type 2 diabetes, primary biliary syndrome, and primary schlerosing cholangitis.

In accordance with the methods described here, administration may be alone as monotherapy, or in combination therapy with one or more additional therapeutic agents, including but not limited to an antihyperlipidemic agent or an anti-diabetic agent. Antihyperlipidemic agents that may be used include HMG CoA enzyme inhibitors (e.g., statins), cholesterol absorption inhibitors, and cholesterol esterase transfer protein (CETP) inhibitors. In embodiments, the antihyperlipidemic agent is selected from a statin, a cholesterol absorption inhibitor, a CETP inhibitor, and pharmaceutically-acceptable salts and prodrugs of any of the foregoing.

Neurological Disorders

In embodiments, the present disclosure provides a method for treating a neurological disorder in a subject in need thereof by administering to the subject a pharmaceutical composition containing a complex as described herein, wherein the complex comprises an amount of an SPM effective to treat the neurological disorder.

In embodiments, the neurological diseases and disorders that may be treated include, without limitation, Alzheimer's disease, peripheral nerve injury, amyotrophic lateral sclerosis, pain, and fibromyalgia. In embodiments, the neurological disease or disorder is selected from postoperative delirium, acute postsurgical pain, fibromyalgia, endometriosis, lower genital tract pain, vulvodynia, chronic lower back pain, treatment or management of pain associated with osteoarthritis, diabetic peripheral neuropathy and musculoskeletal injury or trauma. In the context of the methods described here, the term "treating" may refer to the amelioration or stabilization of one or more clinical symptoms associated with the disease or disorder being treated.

In embodiments, the amount is effective to treat one or more symptoms of the neurological disorder.

In embodiments, the neurological disorder is a psychiatric disorder. In embodiments, the psychiatric disorder is selected from attention deficit hyperactivity disorder (ADHD) and depression. In embodiments, the neurological disease or disorder is postoperative cognitive dysfunction (POCD) or postoperative delirium.

The disclosure also provides methods for treating or managing pain. In embodiments, the pain is nociceptive pain and the method comprises administering to a subject in need of treatment for nociceptive pain a pharmaceutical composition comprising an effective amount a compound described here, or mixtures thereof.

In embodiments, the disclosure provides methods for treating or managing pain associated with inflammation, fibromyalgia, endometriosis, vulvodynia, osteoarthritis, diabetic peripheral neuropathy, and musculoskeletal injury or trauma.

In embodiments, the disclosure also provides methods for treating or managing acute postsurgical pain and chronic lower back pain.

Pulmonary Diseases and Disorders

In embodiments, the present disclosure provides a method for treating a pulmonary disorder in a human subject in need thereof by administering to the subject a pharmaceutical composition containing a complex as described herein, wherein the complex comprises an amount of an SPM effective to treat the pulmonary disease or disorder.

In embodiments, the pulmonary and vascular diseases and disorders that may be treated include, without limitation, asthma, pulmonary inflammation, bronchopulmonary dysplasia, also referred to as chronic lung disease of infancy, cystic fibrosis, allergic airway response, acute lung injury, acute respiratory distress syndrome, lung injury, idiopathic pulmonary fibrosis, bacterial pneumonia, cigarette smoke-induced lung inflammation, and vascular inflammation.

EXAMPLES

Despite having promising pharmacology for treating inflammatory diseases and cancer, SPMs are chemically unstable in part due to a tendency for isomerization of their cis double bonds into a thermodynamically more favorable trans configuration, which has been found to have less potency than the native SPMs. Therefore, the object of this invention is to provide SPM complexes, wherein the stability of the SPM active moiety is remarkably improved, to enable their use in pharmaceutical compositions, To improve the solid-state stability of Resolvin E1 (RvE1), a resolvin that is representative of SPMs with conjugated double bonds vulnerable to isomerization, the inventors evaluated several approaches to protect the RvE1 from exposure to oxygen, light and moisture without use of analog modifications to the chemical structure of the SPM molecule. These approaches included: (i) the suspension of RvE1-MgLys in various lipid excipients including peceol, maisine, labrasol ALF, Span 80, poloxamer Kollisov P124 and Tween 80; (ii) the spray coating of RvE1-MgLys mixed with hydroxypropyl cellulose in a 1:4 ratio (w/w) in isopropyl alcohol using a Wurster fluid-bed process onto microcrystalline cellulose beads with a seal coat of hydroxypropyl cellulose; (iii) the addition of anti-oxidants (0.5% w/w), including alpha-tocopherol, ascorbyl palmitate, propyl gallate, BHT, and BHA, to RvE1-MgLys in methanol and freeze-drying to form a dry powder; and (iv) the use of cyclodextrins, including alpha-CD, beta-CD, gamma-CD, HP-beta-CD and SBE-beta-CD, to complex with RvE1-MgLys. Importantly, only the complexation of RvE1-MgLys with the cyclodextrins provided adequate stabilization of the RvE1 active moiety. This finding was surprising because it has been shown that the stabilizing effects of cyclodextrins can be positive or negative depending on the specific interaction of the reactive part of the guest molecule inside the cyclodextrin cavity, and whether the complex is solid-state or in solution. Given the unique conjugated double-bond systems of SPMs and their known vulnerability to isomerization, a person skilled in the art would not predict a priori that they would be stabilized by one or more cyclodextrins under the specific conditions tested as described below.

Experimentally, RvE1-MgLys was complexed with various cyclodextrins in solution, followed by lyophilization to form a powder, and the resulting compounds were characterized by NMR spectroscopic studies to confirm their novelty through complex formation, the intensity of intramolecular interactions, and the unique orientation of RvE1 inside the CD cavities. The utility of these new compounds was established by their improved chemical stability relative to RvE1-MgLys alone over a period of 16 weeks under accelerated conditions.

Preparation of the Complexes

Example 1: General Methods for Preparation of the Complexes

The main techniques available for cyclodextrin complexation with water-soluble drugs include dissolving the guest and cyclodextrin in water or organic solvent/water mixtures, and then isolating the complex by removal of the solvent via crystallization, co-evaporation under reduced pressure, spray-drying, or freeze-drying. Based on the high solubility of RvE1-MgLys and the small quantities prepared in this experiment, the freeze-drying approach was selected for the initial preparation of the complexes. However, the other isolation techniques described above may be suitable for producing the SPM complexes.

The following steps were used to prepare the SPM complexes for the NMR and stability studies. First, the calculated amounts of RvE1-MgLys were mixed in a molar ratio of 1:2 with the calculated amounts of the various cyclodextrins (see Table 2) and dissolved in 1400 uL of D20, stirred for one hour, and filtered (0.22 μm, MF-Millipore). For NMR studies, the filtrate was transferred to standard 5 mm glass NMR tube for testing. For the stability studies, the filtrate was freeze-dried (VirTis BenchTop Pro freeze dryer) and transferred to open test tubes.

TABLE 2

Sample Preparations of the RvE1-MgLys Cyclodextrin Complexes

| Complex | Components | Quantity |
|---|---|---|
| alpha-CD | RvE1-MgLys | 5.27 mg |
| | alpha-CD | 11.11 mg |
| beta-CD | RvE1-MgLys | 5.56 mg |
| | beta-CD | 13.67 mg |
| gamma-CD | RvE1-MgLys | 5.40 mg |
| | gamma-CD | 15.17 mg |
| HP-beta-CD | RvE1-MgLys | 5.07 mg |
| | HP-beta-CD | 16.93 mg |
| SBE-beta-CD | RvE1-MgLys | 5.04 mg |
| | SBE-beta-CD | 24.48 mg |

NMR Interaction Studies Confirming Complexation with Cyclodextrins

The 1H NMR and 2D ROESY NMR experiments were performed at 298 K on a 600 MHz Varian DDR NMR spectrometer equipped with a 5 mm inverse-detection gradient (IDPFG) probe. Standard pulse sequences and processing routines available in VNMRJ 4.1 were used. 1H chemical shifts (δ) were referenced to the residual HOD peak (δ=4.7900 ppm) present in D20.

Figure 2A:
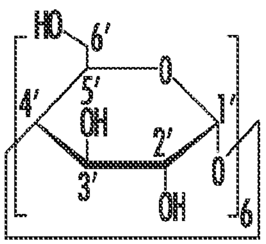
FIG. 2A-C: Structure and atom number assignment of alpha-cyclodextrin (alpha-CD, A), beta-cyclodextrin (beta-CD, B), and gamma-cyclodextrin (gamma-CD, C).
Figure 2B:
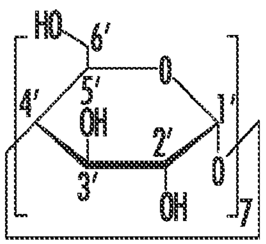
Figure 2C:
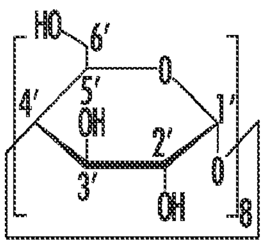
Figure 3A:
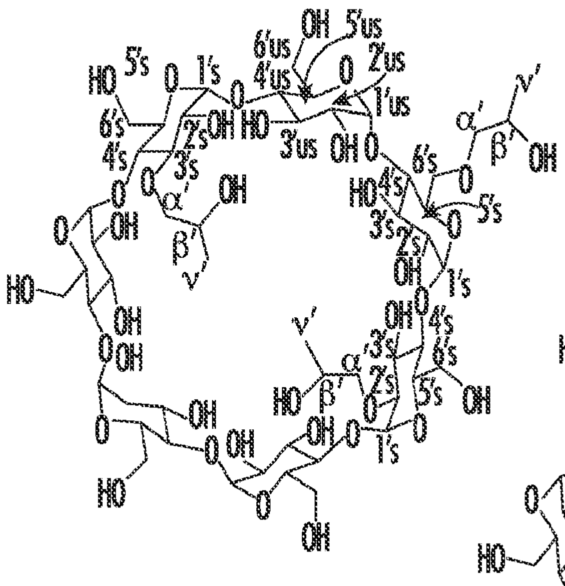
FIG. 3A-B: Structure and atom number assignment of 2-hydroxypropyl-beta cyclodextrin (HP-beta-CD, A), and sulfobutylether beta-cyclodextrin (SBE-beta-CD, B).
Figure 3B:
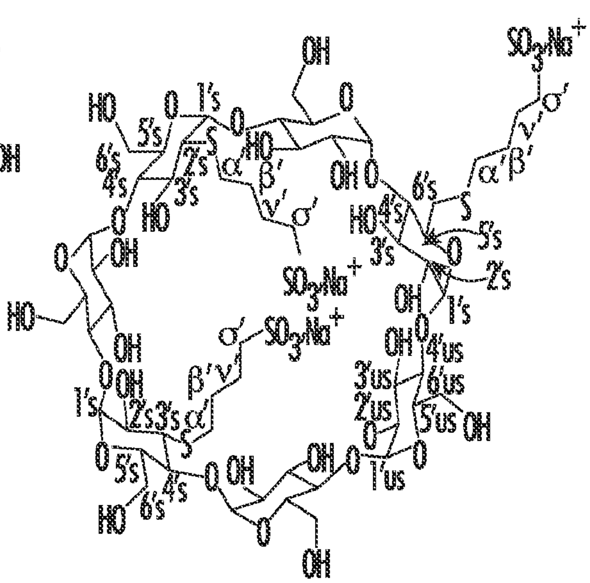

1H spectra were recorded from 16 scans with 2 s relaxation delay applied. 2D Rotating Frame Overhauser Enhancement Spectroscopy (ROESY) spectra were recorded from 8 scans/increment using 2s relaxation delay and 200 increment for native cyclodextrin complexes and 512 increments for randomly substituted cyclodextrin complexes, the spinlock time was set to 300 milliseconds in each case. Additional analyses were conducted using Heteronuclear Single Quantum Coherence (HSQC) NMR to determine proton-carbon single bond correlations. The atom numbering schema of RvE1-MgLys and the alpha-CD, beta-CD, gamma-CD, HP-beta-CD and SBE-beta-CD cyclodextrins used for the NMR spectroscopic studies are shown in FIG. 1-3.

Figure 4:
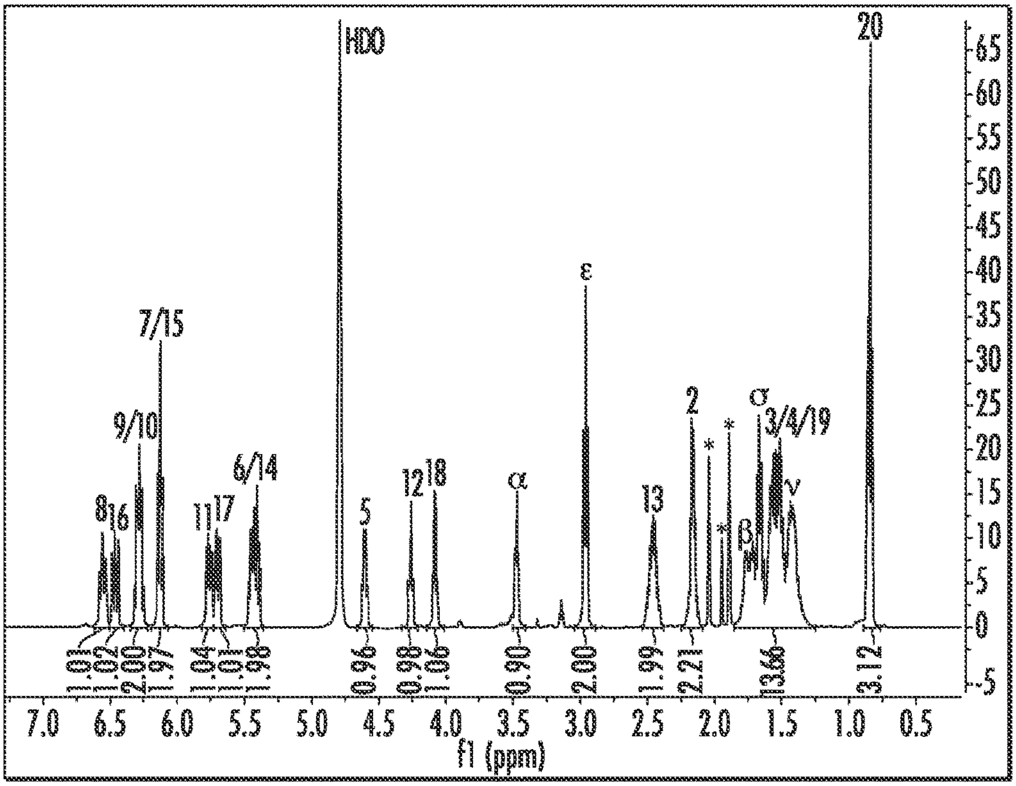
FIG. 4: 1H NMR spectrum of RvE1-MgLys with full assignment, without complexation to a cyclodextrin.

Example 2: NMR Characterization and Intramolecular Interaction of RvE1-MgLys Alone The 1H-NMR spectrum of RvE1-MgLys with full assignment is shown in FIG. 4. Signals of RvE1 are depicted with roman numbers, Greek letters are assigned for the signals of magnesium lysinate, and possible impurities related to RvE1-MgLys are depicted with an asterisk.

From the 1H-NMR spectrum shown in FIG. 4, three well defined regions of RvE1 were identified: (1) the unsaturated region between δ1H=6.5 to 5 ppm; (2) the chiral centers, with secondary hydroxyl groups between δ1H=4.7 to 4 ppm; and (3) the aliphatic region between δ1H=2.5 to 0.7 ppm. The assignment of RvE1-MgLys was done by using further 2D ROESY and 13C NMR experiments.

Figure 5:
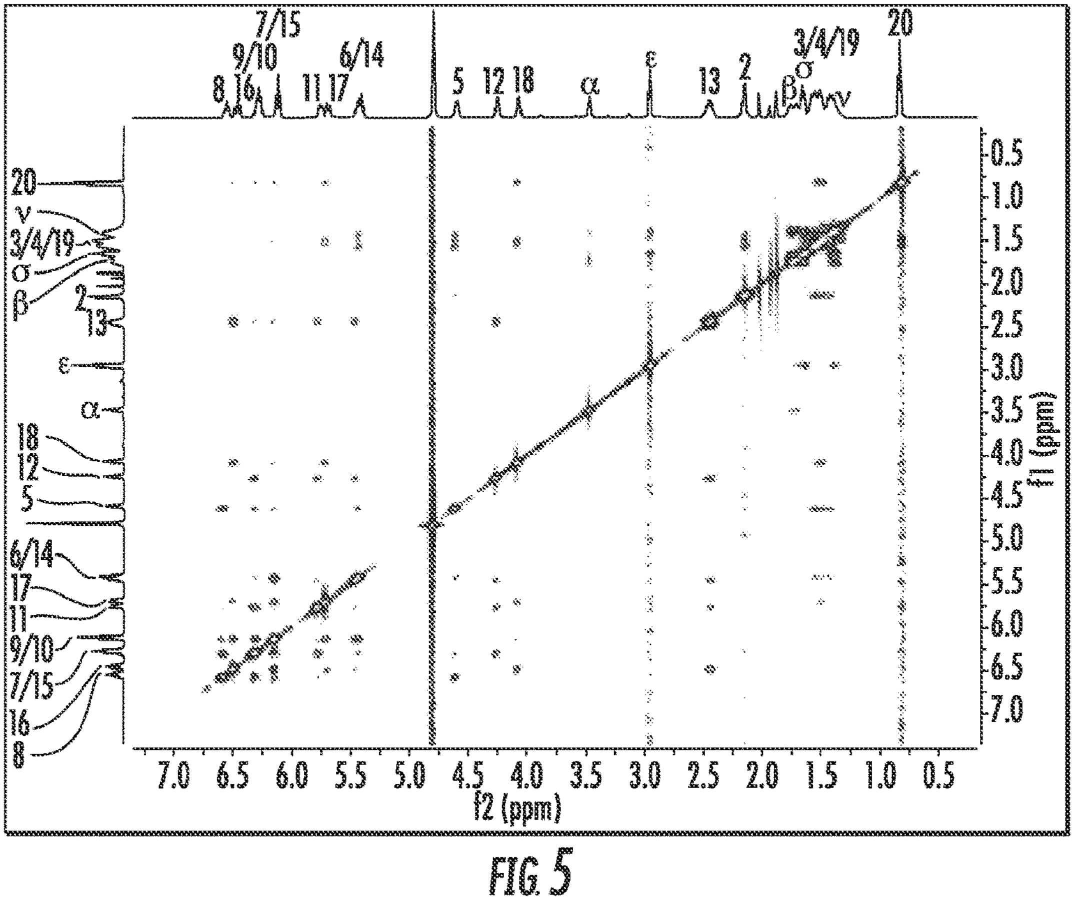
FIG. 5: 2D ROESY spectrum of RvE1-MgLys, without complexation to a cyclodextrin.

To map the intramolecular interactions, and any intermolecular interactions between the components of RvE1-MgLys, analysis by 2D ROESY was performed (FIG. 5).

Figure 6:
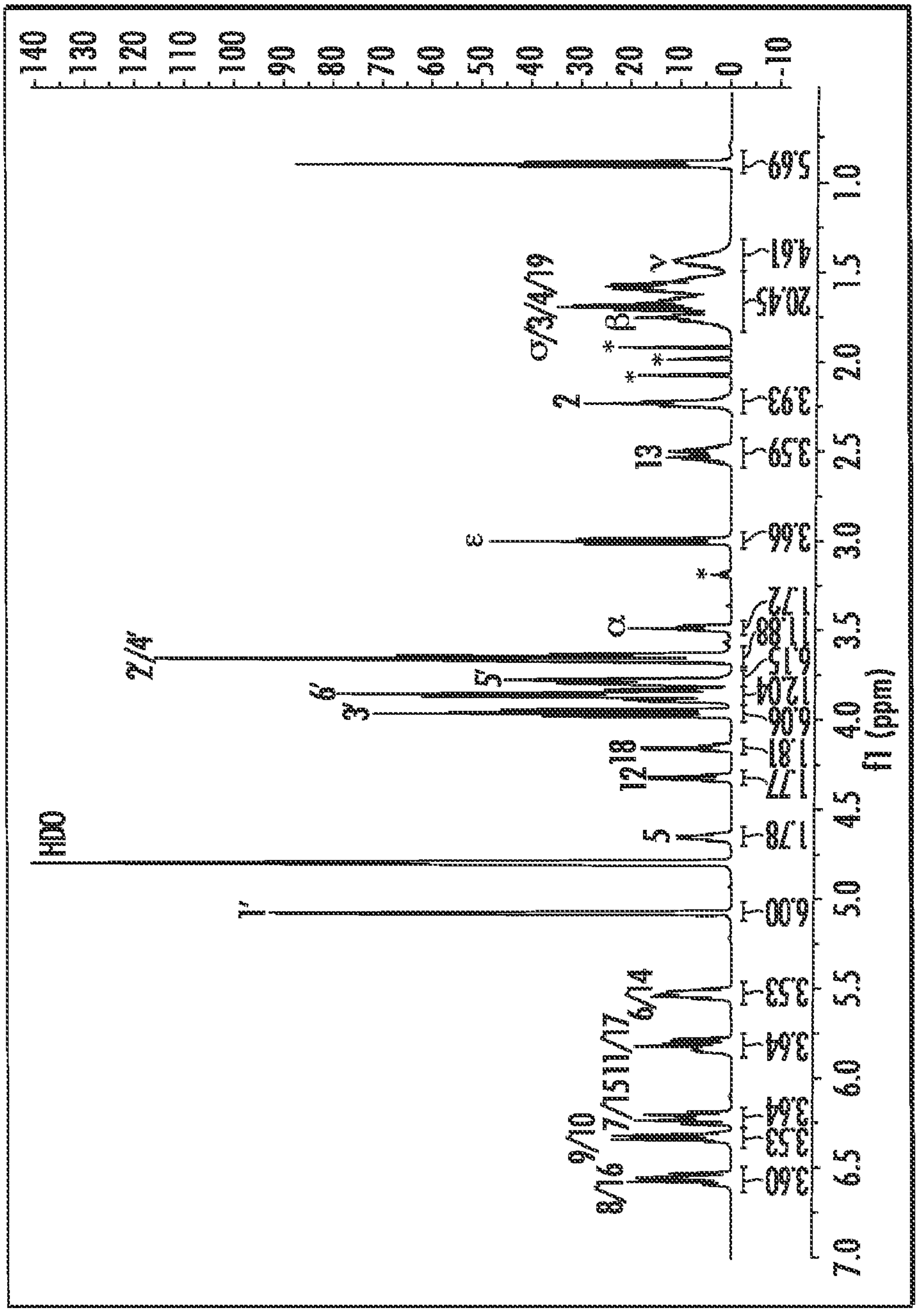
FIG. 6: 1H NMR spectrum of RvE1-MgLys complexed with alpha-CD with full assignment.

Example 3: NMR Characterization and Intermolecular Interaction Studies of RvE1-MgLys Complexed with Alpha-Cyclodextrin As shown in FIG. 6, the NMR signals of the alpha-CD complex are found in a well-defined region of the spectrum. The anomeric protons appear between δ1H=5.0-5.2 ppm, while the other protons of the glucopyranose units resonate between δ1H=3.5-4.0 ppm (frequently referred as the core region).

In general, complex formation will induce shifts in the 1H-NMR spectra of the guest and host molecules such that previously non-overlapping signals between the guest and host may become overlapping (called multiplets) and overlapping signals may shift apart partially or completely.

Figures 7A, 7B, 7C, 7D, 7E, 7F:
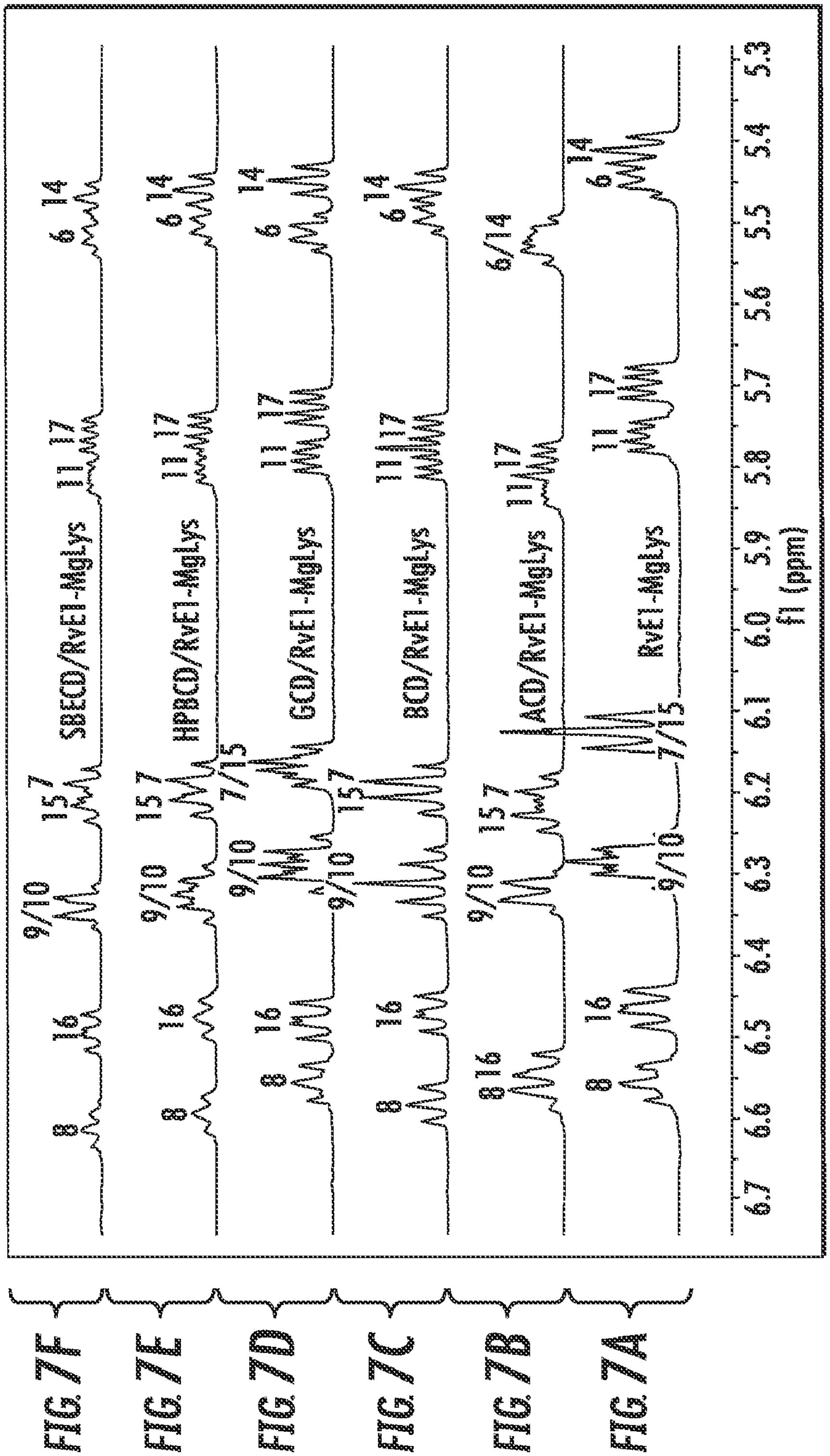
FIG. 7A-F: Stacked partial 1H NMR spectrum of the unsaturated region of RvE1-MgLys alone (A, first from bottom) and complexed with alpha-CD, beta-CD, gamma-CD, HP-beta-CD and SBE-beta-CD (B—F, respectively).

Signal shifts associated with complex formation of RvE1-MgLys and alpha-CD were indicated by comparing the 1H-NMR spectra of the unsaturated region of RvE1-MgLys alone (FIG. 7*a*) to the 1H-NMR spectra of the unsaturated region of RvE1-MgLys in the alpha-CD complex (FIG. 7*b*) It was observed that several signals in the unsaturated region of RvE1-MgLys that were previously separate became overlapping multiplets (e.g., 8/16 and 11/17), while some of the originally overlapping signals shifted apart (7/15). Importantly, minimal shifts were observed in the saturated region of RvE1-MgLys alone compared to RvE1-MgLys in the alpha-CD complex (FIG. 8), indicating minimal interaction in this region of the RvE1 molecule.

Figure 9:
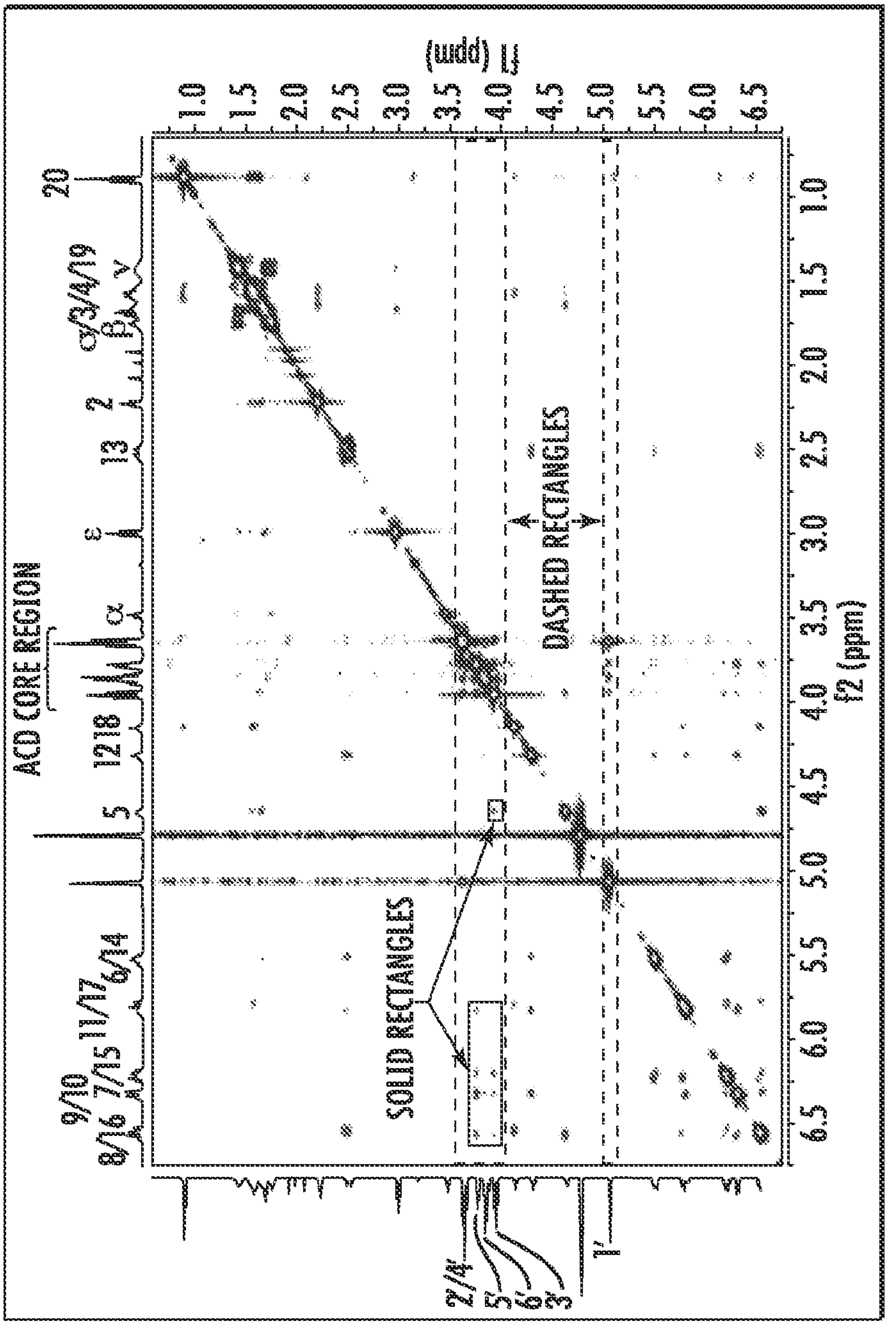
FIG. 9: 2D ROESY spectrum of RvE1-MgLys complexed with alpha-CD with full assignment.

2D ROESY spectrum analyses were performed to provide detailed information on the plausible host-guest interactions of RvE1-MgLys with alpha-CD (FIG. 9). As the signals of alpha-CD appear in a well-defined range of the spectrum, the likely areas of intermolecular interactions can be determined, shown in dashed rectangles, while specific interactions between the guest and host are emphasized by solid rectangles. Using 2D ROESY spectrum analysis, intermolecular correlations were demonstrated between the protons of alpha-CD that are inside the alpha-CD cavity (3' and 5') and on the primary rim of the cavity (6') and the protons of RvE1-MgLys attached to the unsaturated carbons (6 to 12) and one adjacent to them (5). Further, no crosspeaks between the amino acid chelate (MgLys) components of RvE1-MgLys and the alpha-CD were detected.

Figure 10:
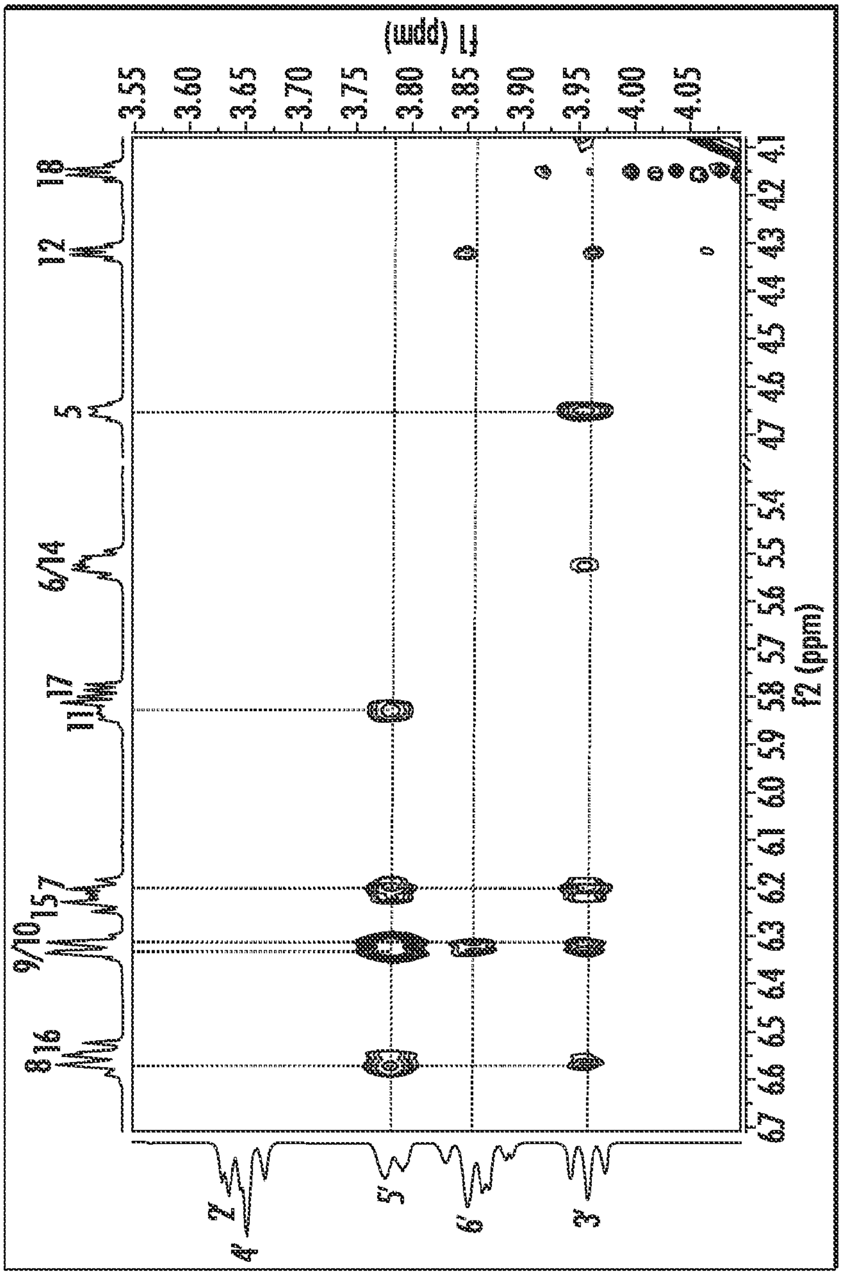
FIG. 10: Partial 2D ROESY spectrum of RvE1-MgLys complexed with alpha-CD.
Figure 23A:
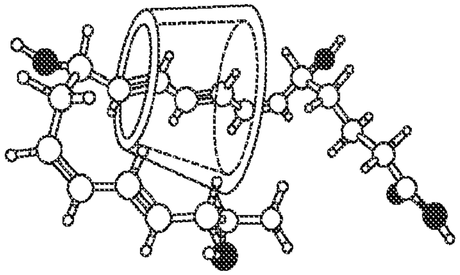
FIG. 23A-E: Schematics illustrating the molecular orientation of RvE1 in the cavities of alpha-CD, beta-CD, gamma-CD, HP-beta-CD, and SBE-beta-CD, A-E respectively.

FIG. 10 shows the enlarged section of the intermolecular interactions, which enable determination of the exact mode of interaction. These spectra indicate that the protons of RvE1-MgLys interacting with alpha-CD are 5, 7, 8, 9, 10 and 11. Based on these data, the plausible orientation of RvE1 inside the alpha-CD cavity is provided in FIG. 23*a*.

Figure 11:
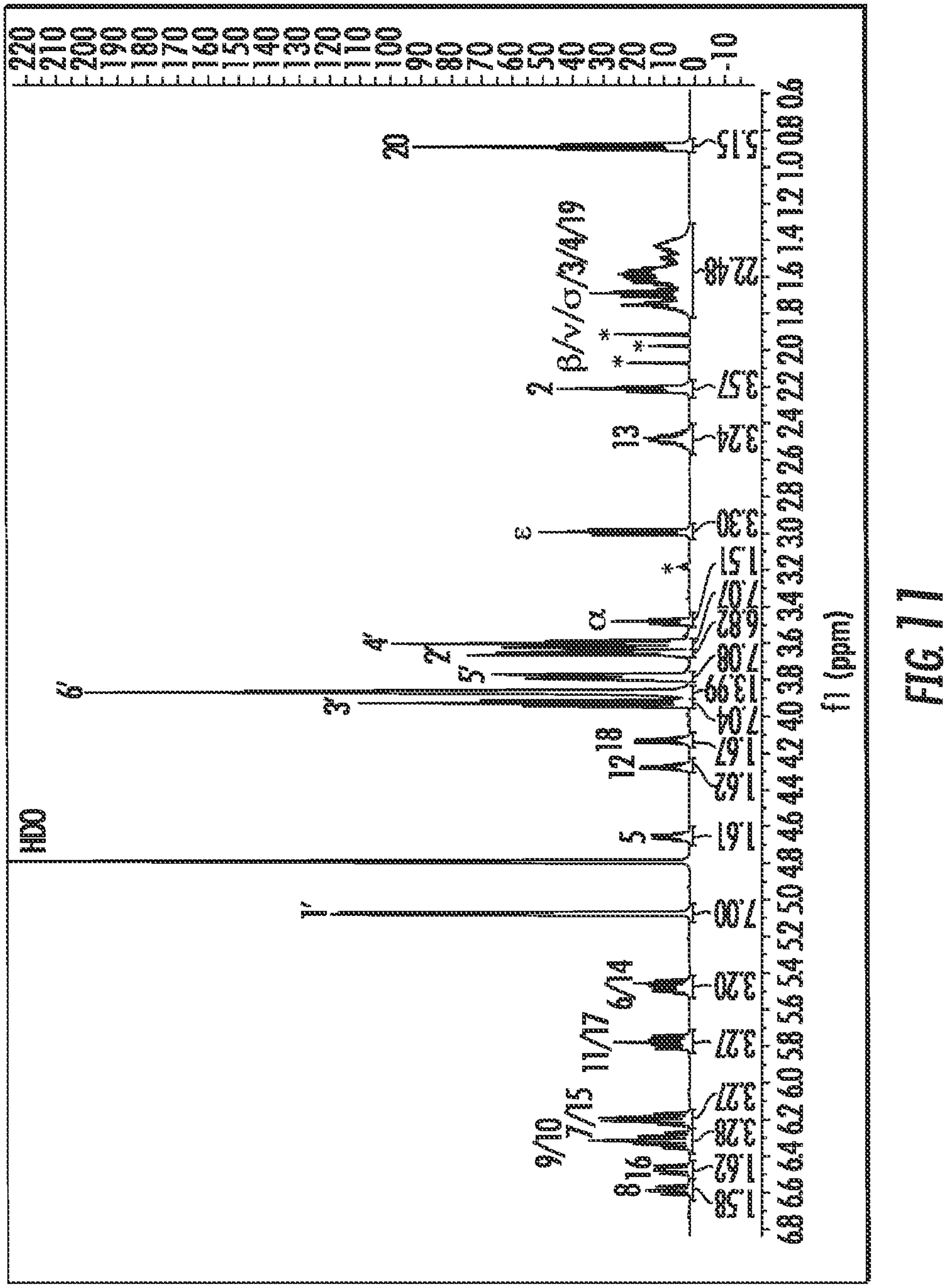
FIG. 11: 1H NMR spectrum of RvE1-MgLys complexed with beta-CD with integration and full assignment.

Example 4: NMR Characterization and Intermolecular Interaction Studies of RvE1-MgLys Complexed with Beta-Cyclodextrin FIG. 11 indicates that the NMR signals of the beta-CD complex are found in a well-defined region of the spectrum similar to the alpha-CD complex.

As shown in FIG. 7, signals of the 8/16 and 6/14 multiplets were completely and partially separated, respectively, while separation of 7/15 was somewhat decreased compared to RvE1-MgLys alone, indicative of complex formation.

Figures 8A, 8B, 8C, 8D, 8E, 8F:
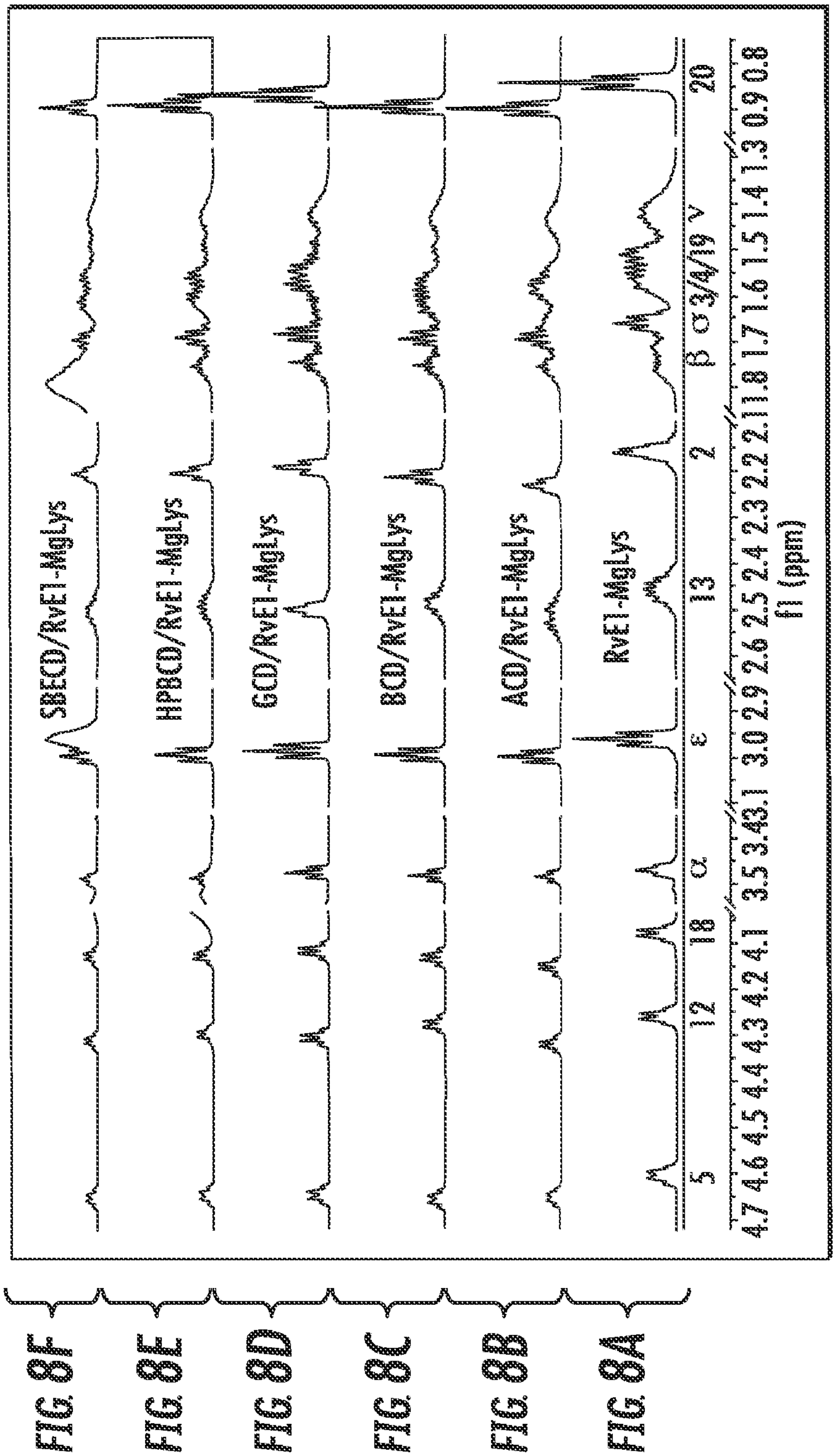
FIG. 8A-F: Stacked partial 1H NMR spectrum of the saturated region of RvE1-MgLys alone and complexed with alpha-CD, beta-CD, gamma-CD, HP-beta-CD and SBE-beta-CD, A-F respectively from bottom.

Minimal signal shifts were observed in saturated part of RvE1-Mg-Lys in the beta-CD complex (FIG. 8).

Figure 12:
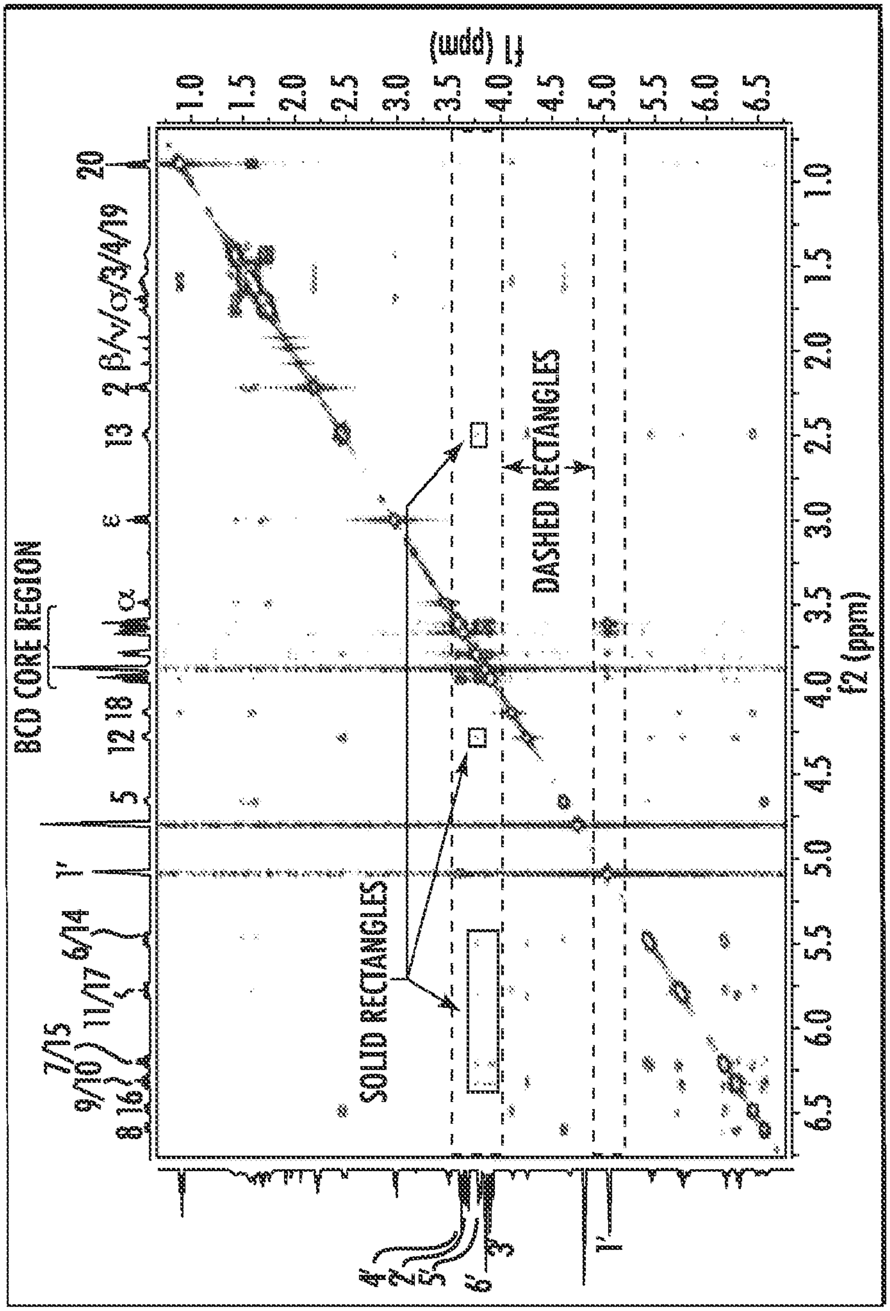
FIG. 12: 2D ROESY spectrum of RvE1-MgLys complexed with beta-CD with full assignment.
Figure 13:
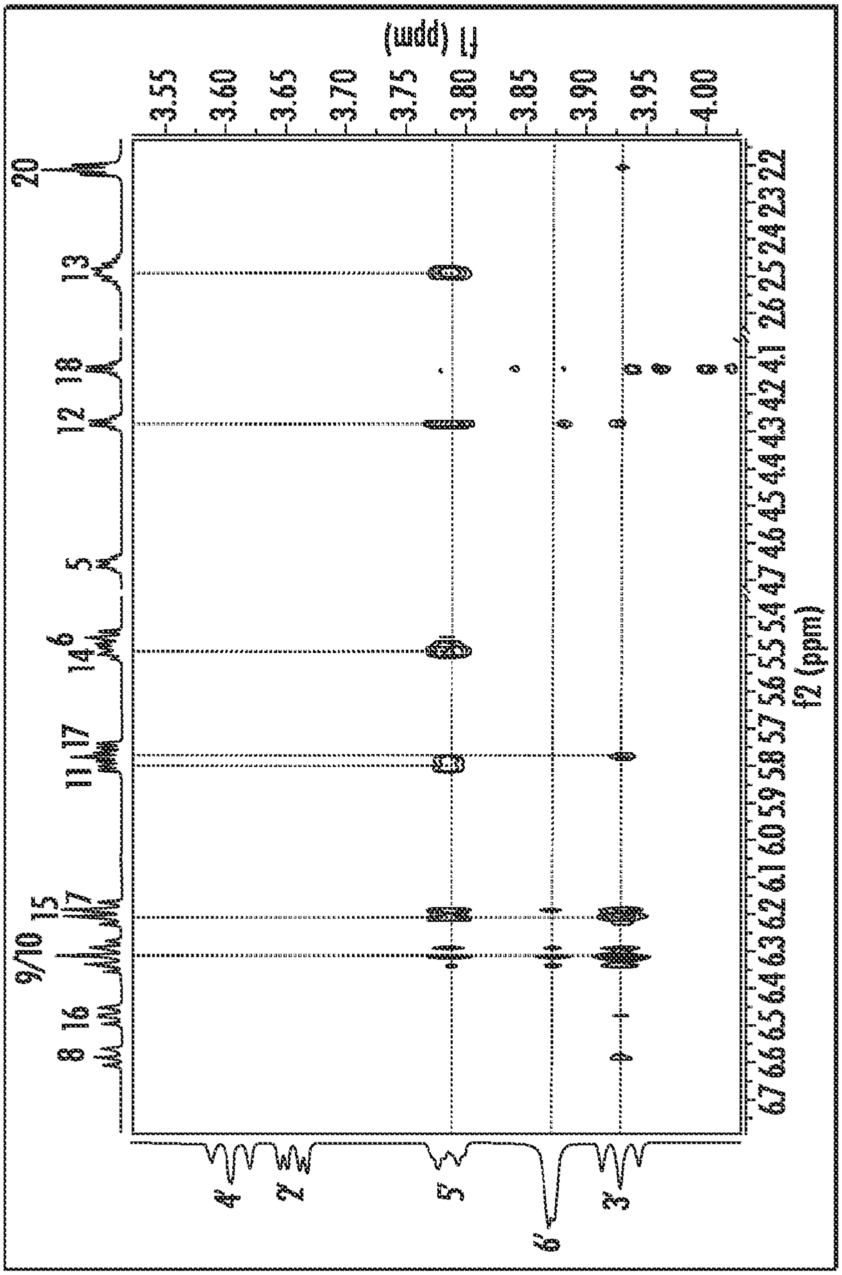
FIG. 13: Enlarged partial 2D ROESY spectrum of RvE1-MgLys complexed with beta-CD.
Figure 23B:
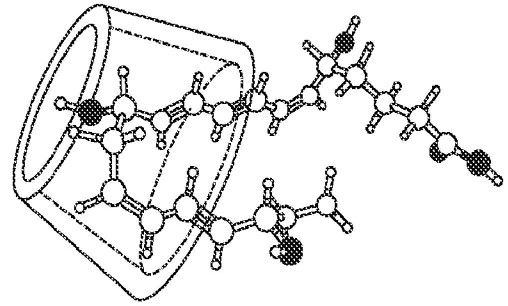

2D ROESY spectrum analyses were also performed to provide detailed information on the plausible host-guest interactions of RvE1-MgLys with beta-CD (FIG. 12), with the likely areas of intermolecular interactions shown in dashed rectangles and specific interactions highlighted by solid rectangles. The 2D ROESY analysis indicates that some of the signals of RvE1-MgLys in the core region have spatial proximity with the inner protons of beta-CD (3' and 5'), indicating the formation of a host-guest complex. Further analysis of the enlarged section of the intermolecular interactions in the 2D ROESY spectrum (FIG. 13) was completed to determine the exact site and mode of inclusion, which showed unequivocal spatial proximity between the middle part of RvE1 (protons 8-15) and the inner side of beta-CD cavity (protons 3' and 5'). Based on these data, the plausible orientation of RvE1 inside the beta-CD cavity is provided in FIG. 23*b*.

Figure 14:
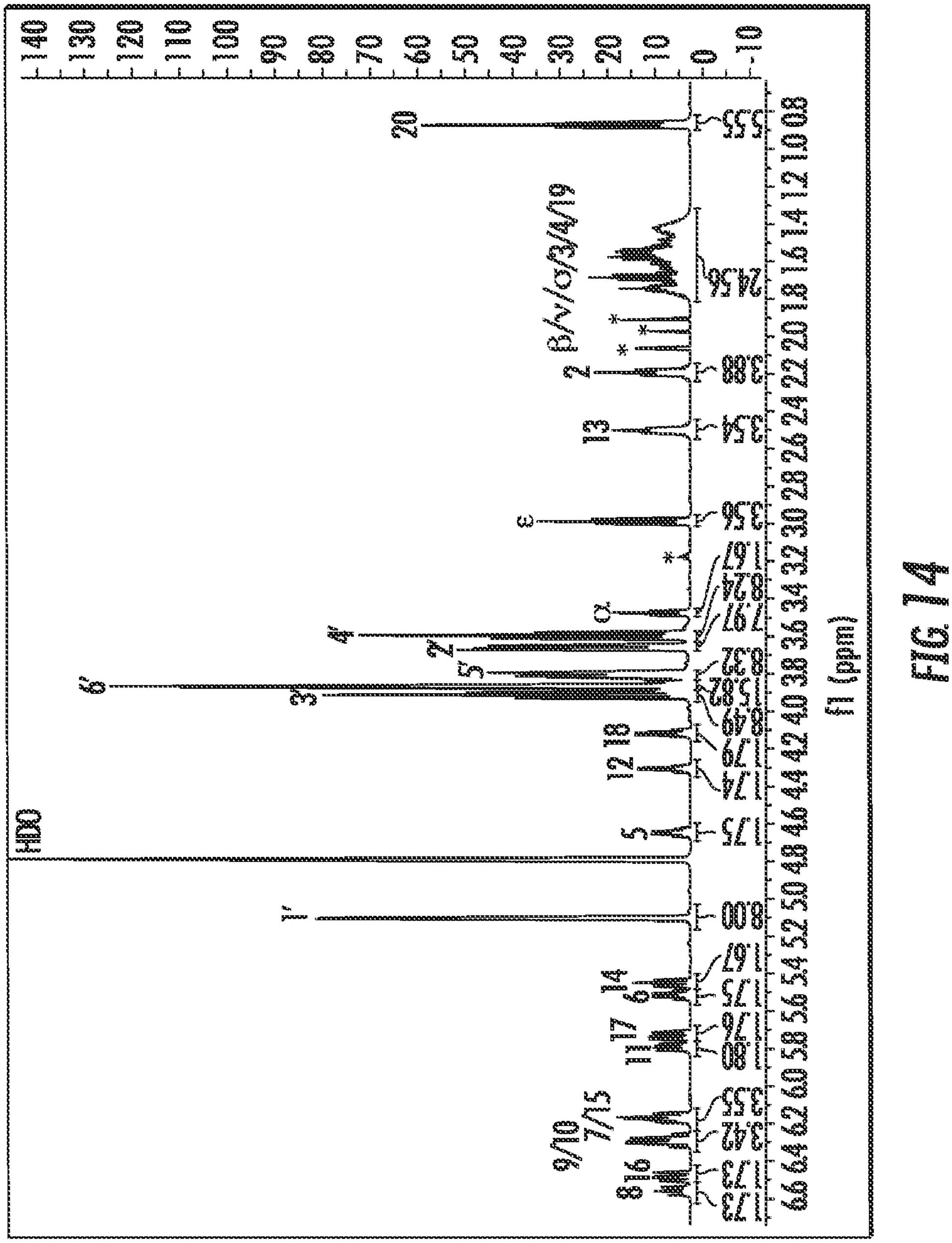
FIG. 14: 1H NMR spectrum of RvE1-MgLys complexed with gamma-CD with integration and full assignment.

Example 5: NMR Characterization and Intermolecular Interaction Studies of RvE1-MgLys Complexed with Gamma-Cyclodextrin FIG. 14 indicates that the NMR signals of the gamma-CD complex are found in a well-defined region of the spectrum, similar to the alpha-CD and beta-CD complexes.

As shown in FIG. 7, the original overlapping signals of 8/16 and 6/14 are partially and completely separated, respectively, indicating complex formation between the unsaturated region of RvE1-MgLys and gamma-CD. As with the alpha-CD and beta-CD complexes, minimal signal shifts were observed in saturated part of RvE1-Mg-Lys in the gamma-CD complex (FIG. 8).

Figure 15:
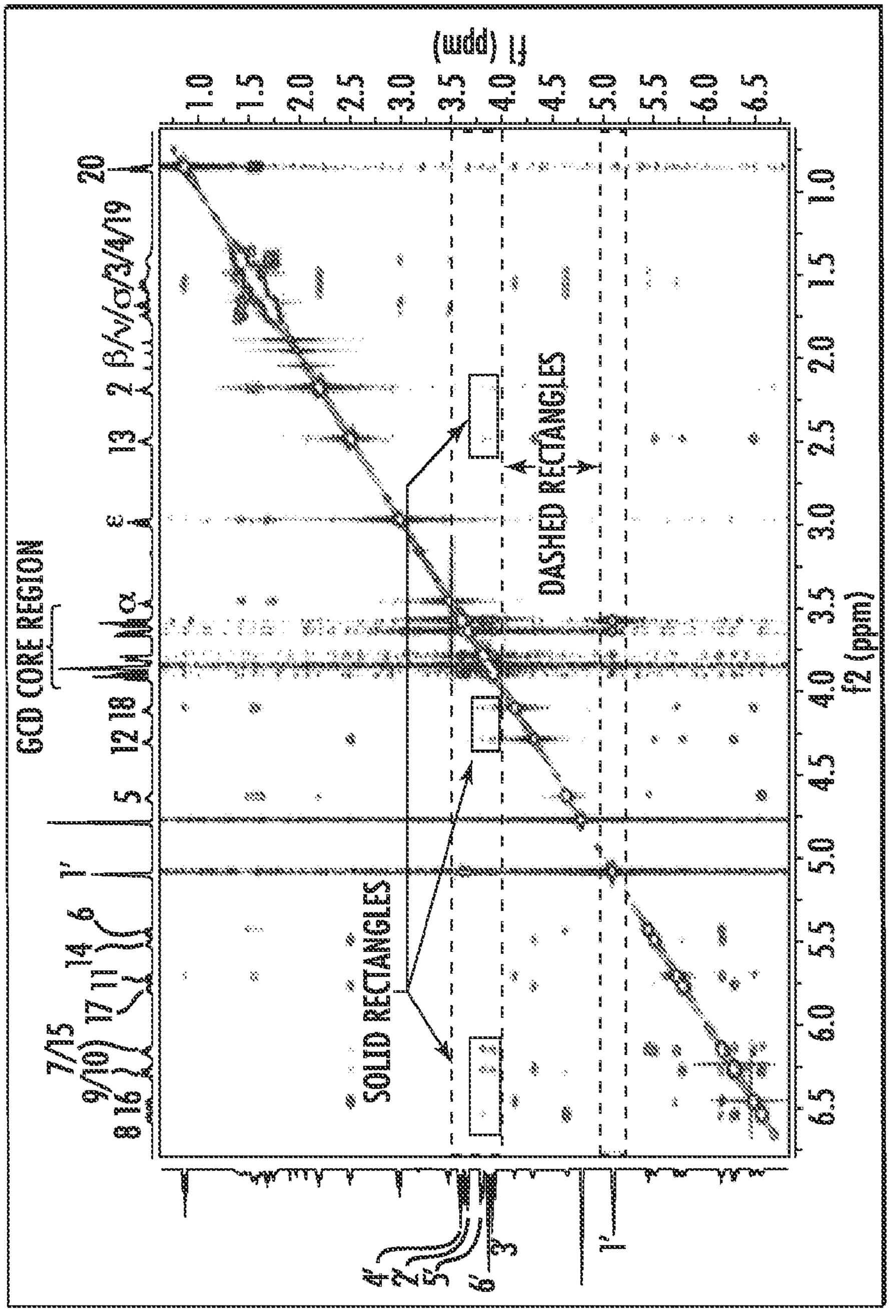
FIG. 15: 2D ROESY spectrum of RvE1-MgLys complexed with gamma-CD with full assignment.
Figure 16:
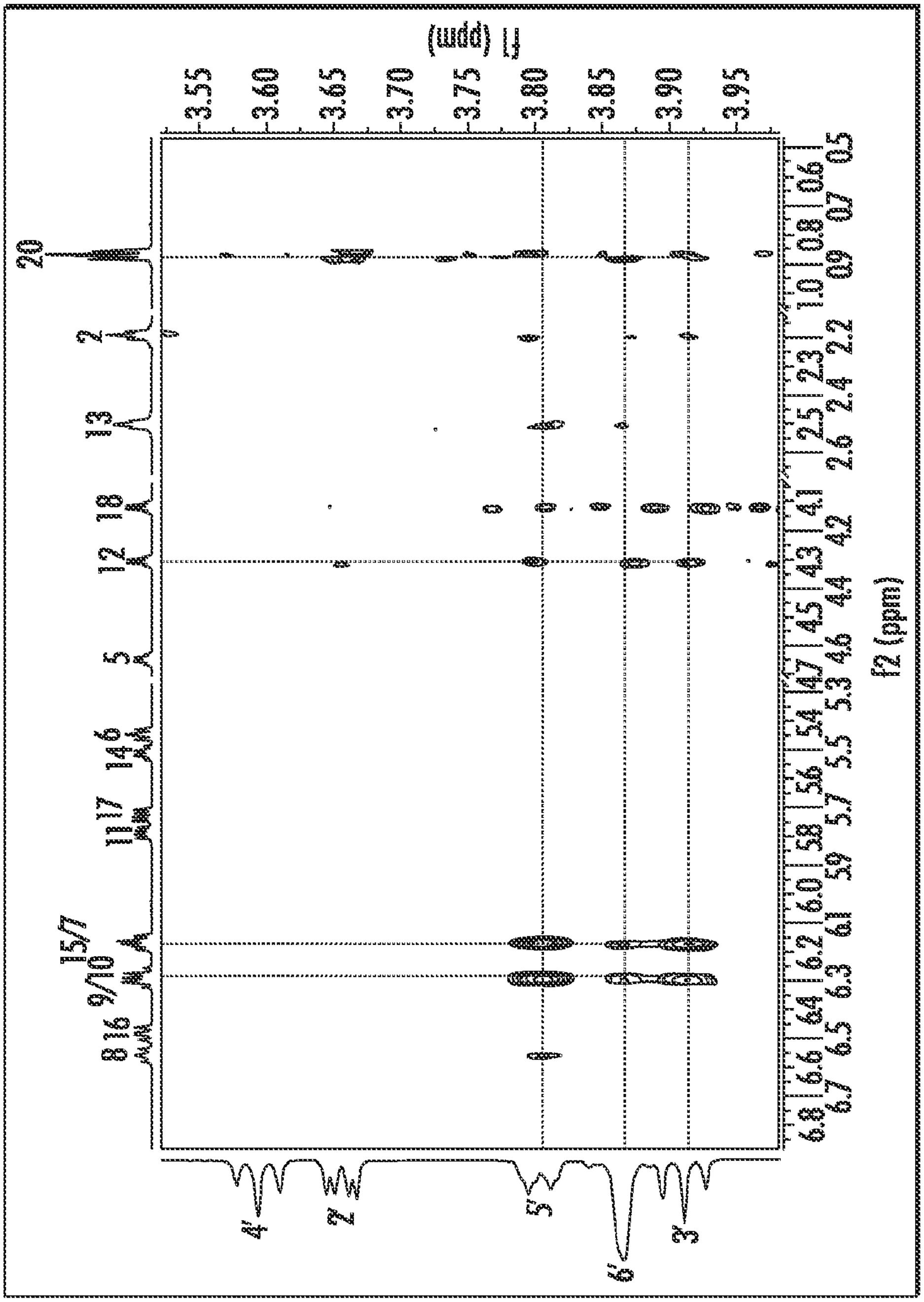
FIG. 16: Enlarged partial 2D ROESY spectrum of RvE1-MgLys complexed with gamma-CD.
Figure 23C:
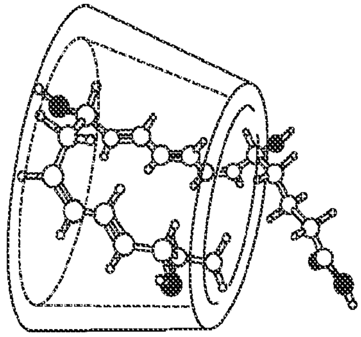

2D ROESY spectrum analyses were performed on the gamma-CD complex to provide detailed information on the plausible host-guest interactions (FIG. 15). This analysis detected cross-peaks between signals of RvE1-MgLys and the core region of gamma-CD in the designated areas of the intermolecular correlations indicated by dashed rectangles. The most intensive cross-peaks indicating correlation between the inner protons of gamma-CD (3' and 5') and signals of the unsaturated region of RvE1-MgLys are highlighted by solid rectangles. Further analysis of the enlarged section of the intermolecular interactions in 2D ROESY spectrum (FIG. 16) was completed to determine the exact site and mode of inclusion. The most intensive cross-peaks in the gamma-CD can be observed between 9, 10 and 15 protons of RvE1-MgLys (located in the center of the molecule) and 3', 5' and 6' protons of gamma-CD. Additional signals were between the same protons of gamma-CD and the 12 and 20 protons of RvE1-MgLys. Based on these data, the plausible orientation of RvE1 inside the gamma-CD cavity is provided in FIG. 23*c*.

Figure 17:
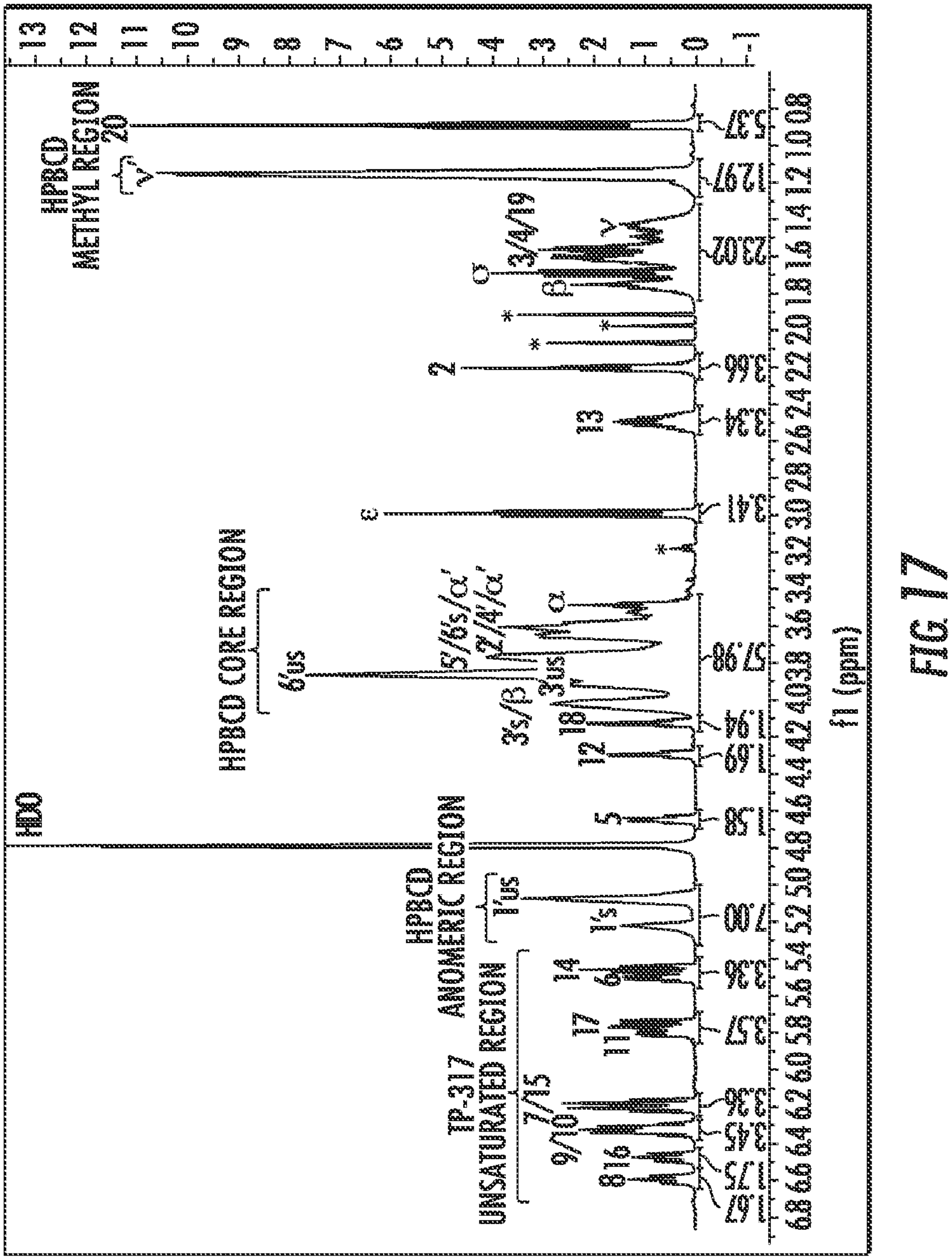
FIG. 17: 1H NMR spectrum of RvE1-MgLys complexed with HP-beta-CD with integration and full assignment.

Example 6: NMR Characterization and Intermolecular Interaction Studies of RvE1-MgLys Complexed with 2-Hydroxypropyl-Beta-Cyclodextrin Based on FIG. 17, the NMR signals of the HP-beta-CD complex can be grouped into three separate regions. The anomeric protons appear between δ1H=5.0-5.2 ppm. Because HP-beta-CD is randomly substituted derivative of the native CDs, there are two types of anomeric signals in HP-beta-CD: one represents the unsubstituted type, while the other (usually the one with higher chemical shift) stands for the substituted type. The HP-beta-CD core is found between δ1H=3.5-4.2 ppm and includes the signals of the sidechain (α' and β'). The methyl (γ') protons of the sidechain establish the third group of signals of HP-beta-CD around δ1H=1.0-1.2 ppm.

As shown in FIG. 7, slight signal changes of RvE1-MgLys in the HP-beta-CD complex compared to its spectra as RvE1-MgLys alone indicate chemical shifts induced by the presence of HP-beta-CD. The pattern is similar to that observed in the case of beta-CD system, where the greatest difference is the partial separation of 7/15 signals, and partial overlapping of 11/17 signals.

Figure 18:
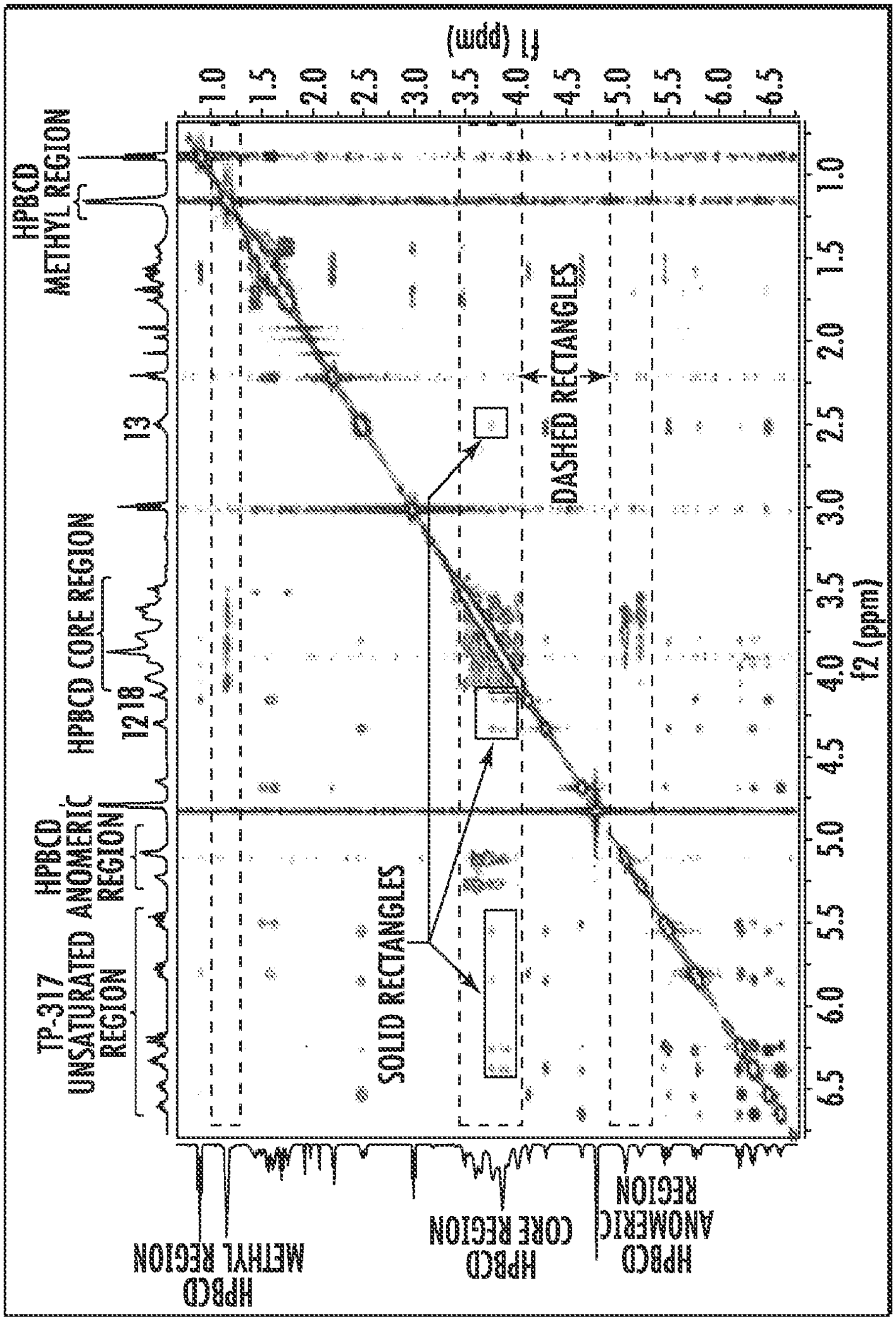
FIG. 18: 2D ROESY spectrum of RvE1-MgLys complexed with HP-beta-CD with full assignment.
Figure 19:
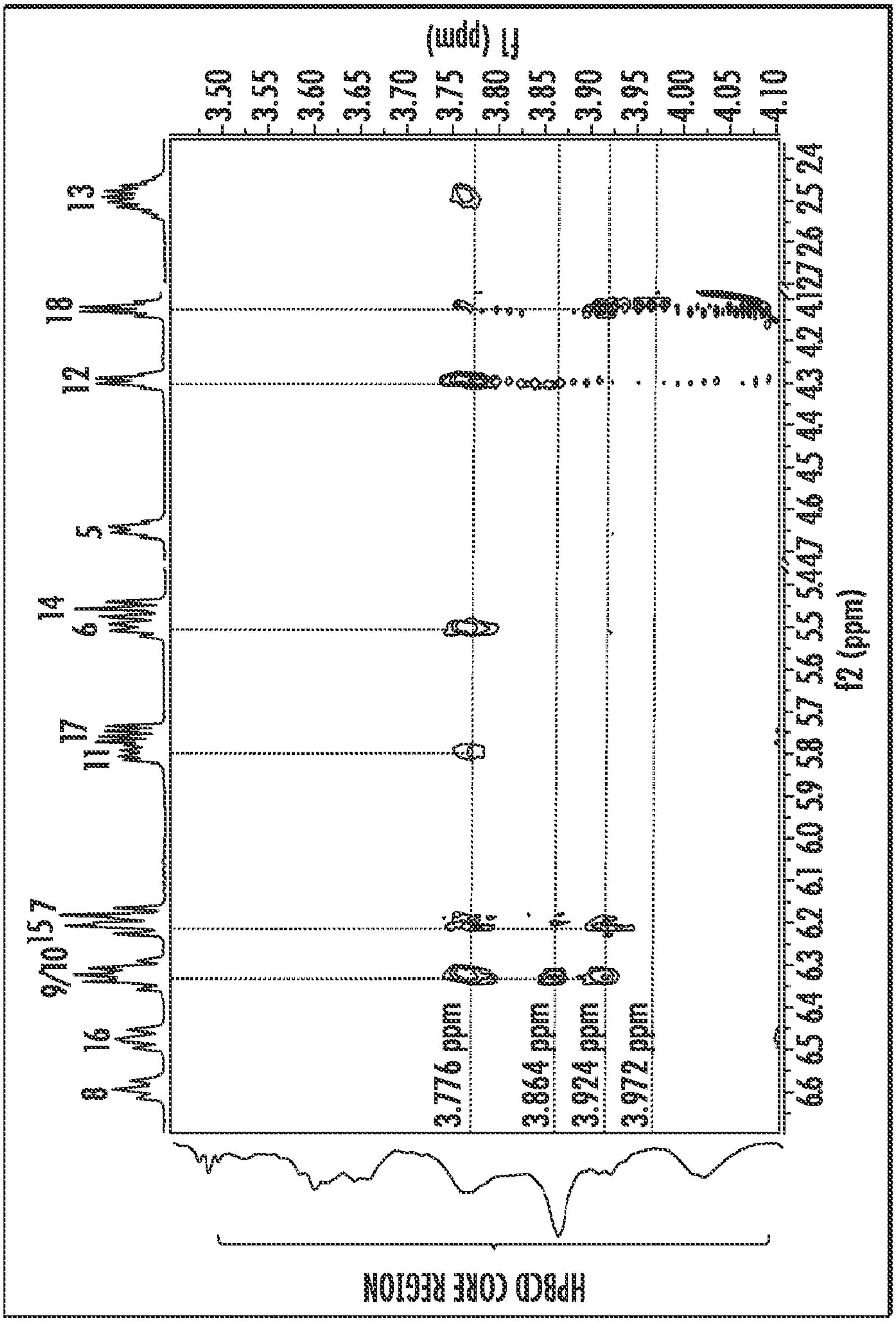
FIG. 19: Enlarged partial 2D ROESY spectrum of RvE1-MgLys complexed with HP-beta-CD.
Figure 23D:
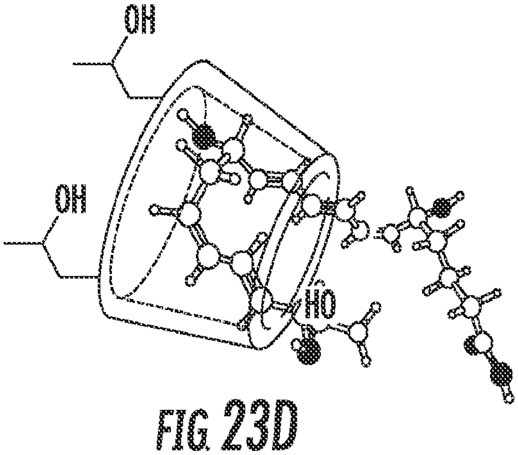

As shown in the 2D ROESY spectrum analysis of the HP-beta-CD complex in FIG. 18, in the designated area of the intermolecular correlations indicated by the dash rectangles, some cross-peaks can be detected between signals of RvE1-MgLys and the core region of HP-beta-CD. Further analysis of the enlarged section of the intermolecular interactions in 2D ROESY spectrum indicate that the most intensive cross-peaks are those of protons 9, 10, 12 and 18, with additional interactions detected for protons 6, 11 and 13 (FIG. 19). Based on these data, it is clear that the observed intermolecular interactions are located in the interior HP-beta-CD at the 3', 5' and 6' protons, indicating complex formation inside the cavity, with a plausible orientation as provided in FIG. 23*d*.

Figure 20:
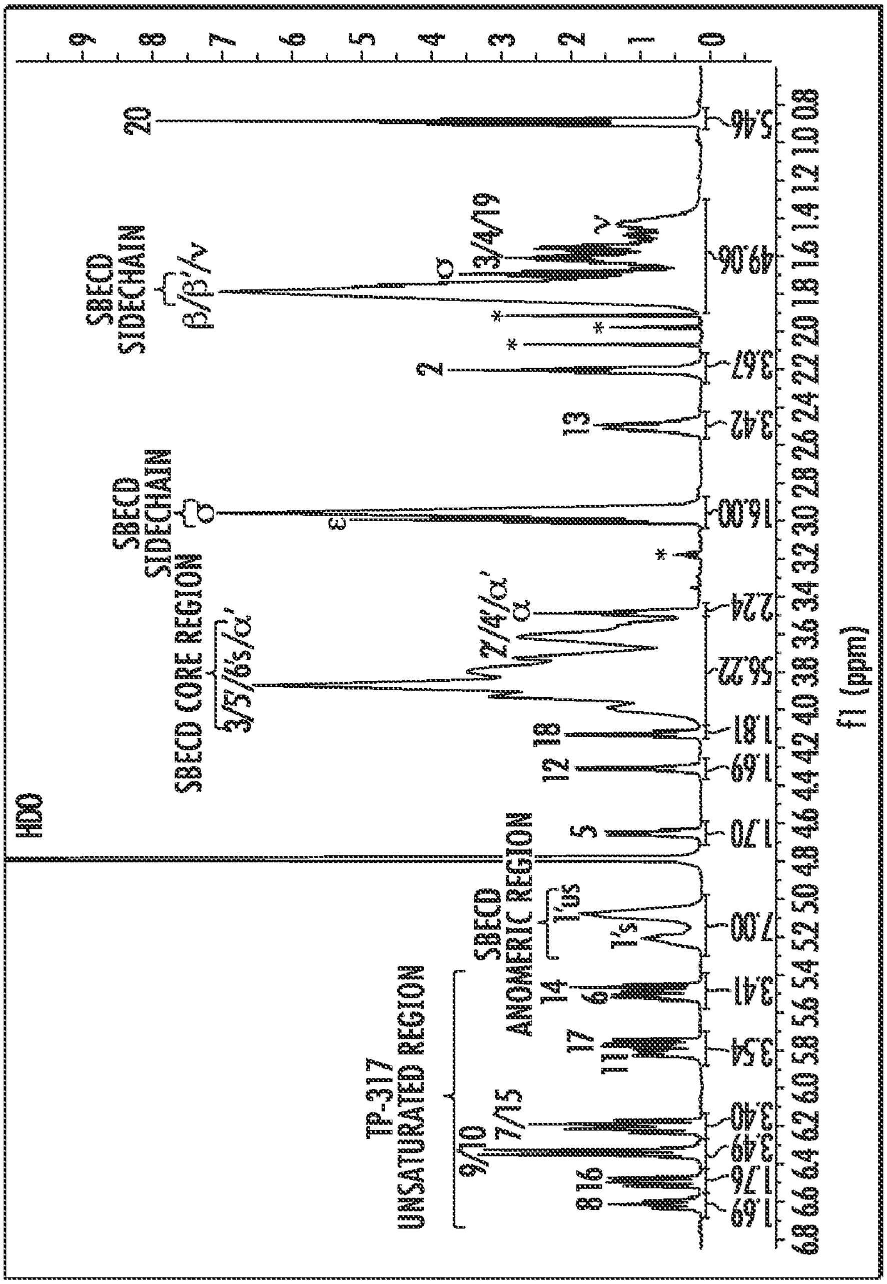
FIG. 20: 1H NMR spectrum of RvE1-MgLys complexed with SBE-beta-CD with integration and full assignment.

Example 7: NMR Characterization and Intermolecular Interaction Studies of RvE1-MgLys Complexed with Sulfobutylether Beta-Cyclodextrin Based on FIG. 20, the 1H NMR signals of the SBE-beta-CD complex also can be grouped into three separate regions. The anomeric protons appear between δ1H=5.0-5.2 ppm. As with HP-beta-CD, SBE-beta-CD has two types of anomeric signals: one represents the unsubstituted type, while the other (usually the one with higher chemical shift) stands for the substituted type. The SBE-beta-CD core is found between δ1H=3.5-4.1 ppm. The α' protons of the sidechain overlaps with the core region, and the remaining signals of the sidechain comprise two separated regions, one between δ1H=2.9-3.0 ppm representing the δ' protons and another between δ1H=1.7-1.9 ppm, including the middle protons of the sidechain, β' and γ'.

Figure 21:
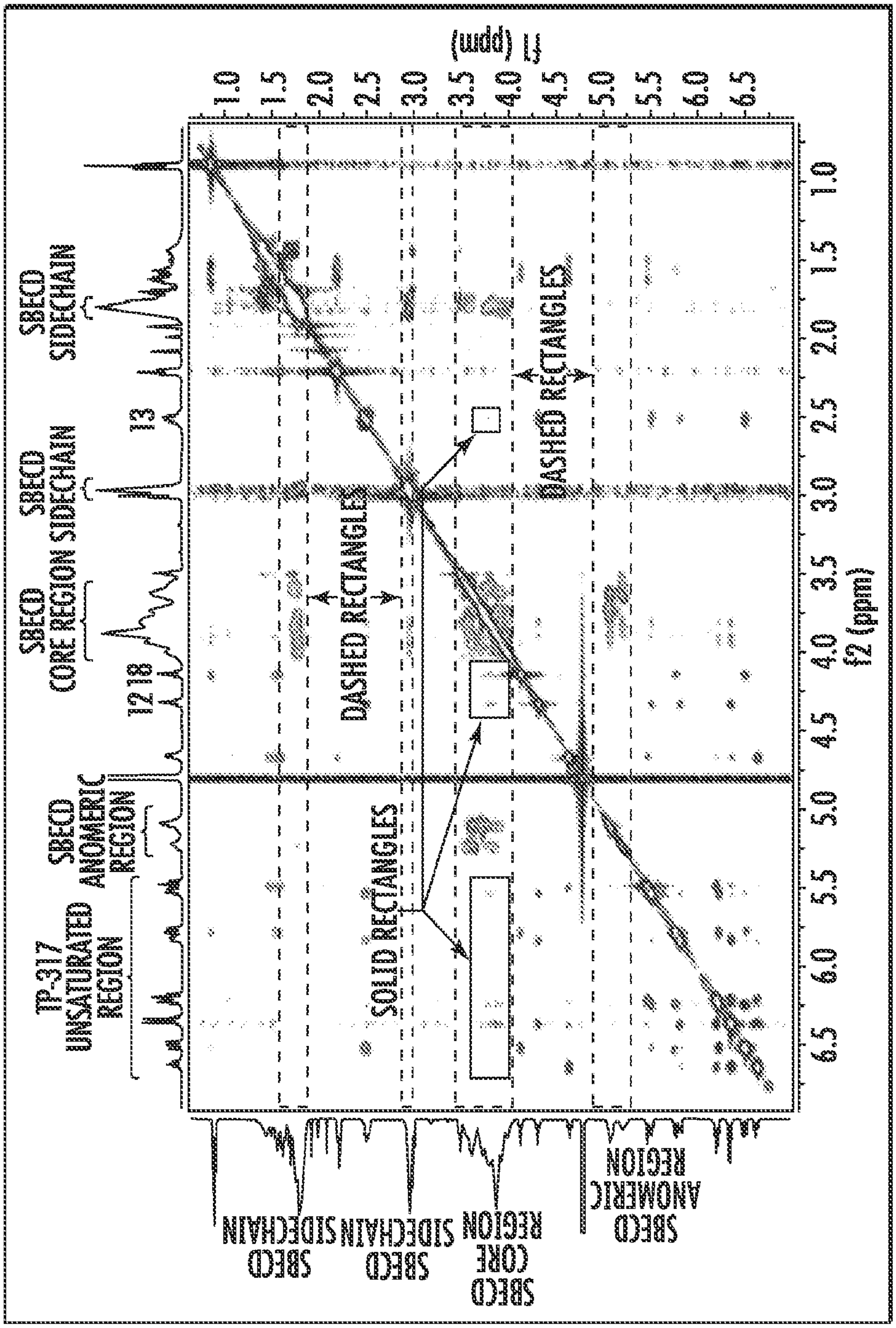
FIG. 21: 2D ROESY spectrum of RvE1-MgLys complexed with SBE-beta-CD with full assignment.
Figure 22:
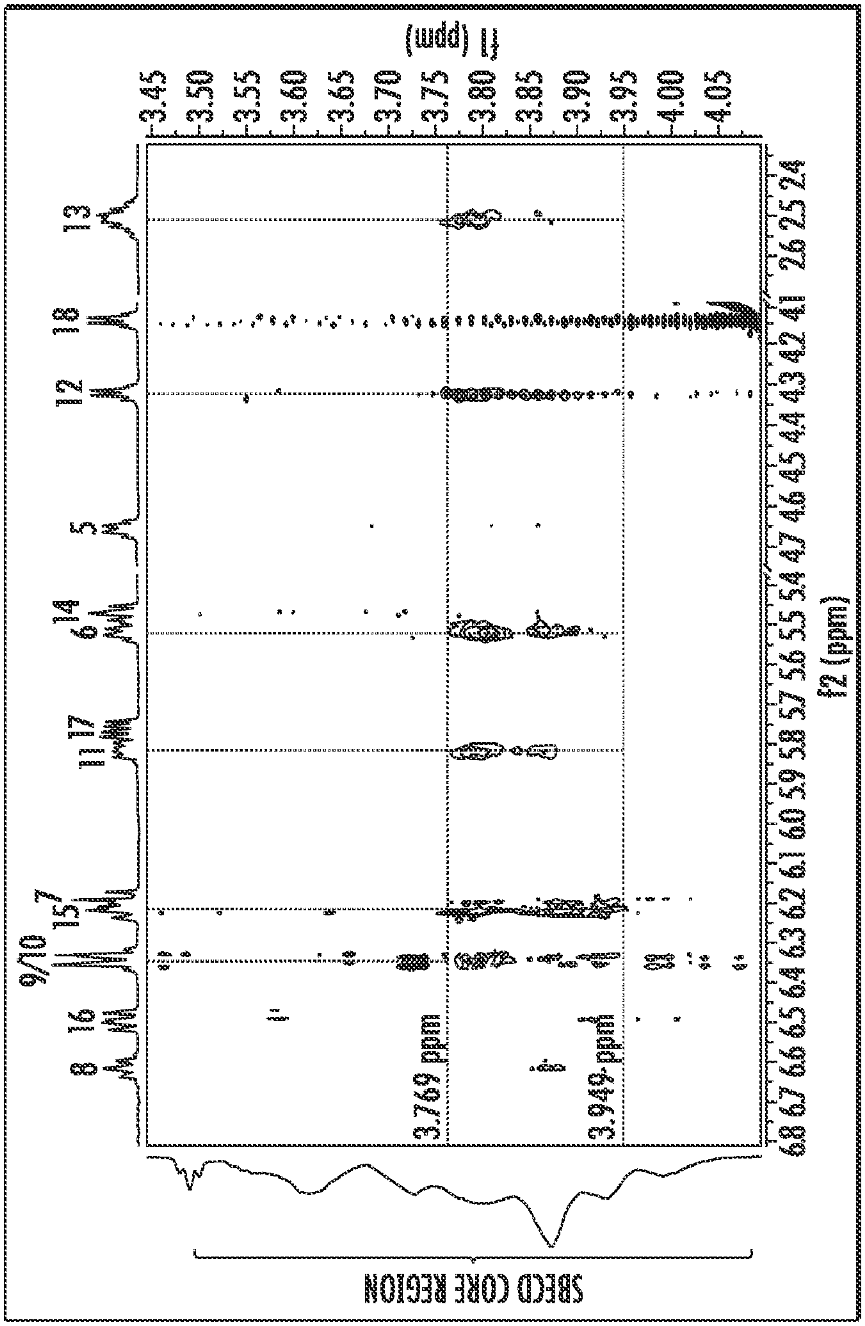
FIG. 22: Enlarged partial 2D ROESY spectrum of RvE1-MgLys complexed with SBE-beta-CD.
Figure 23E:
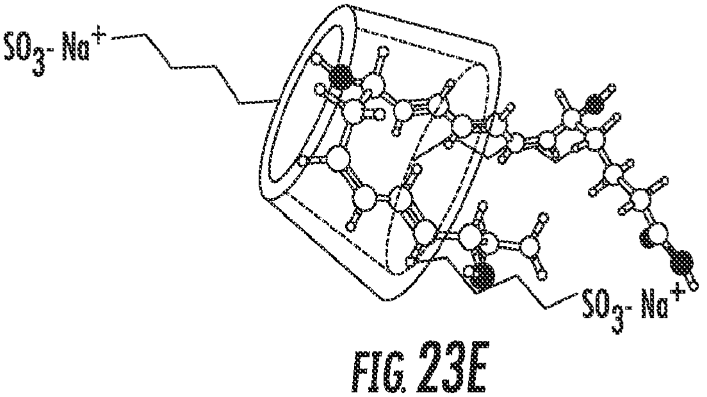
Figure 24A:
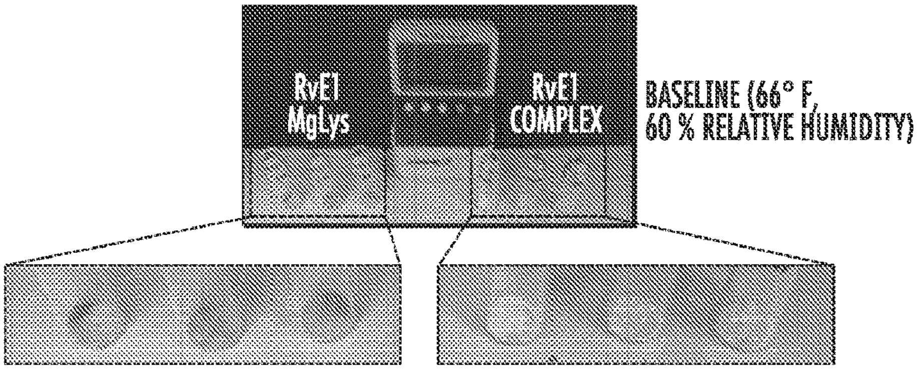
FIG. 24A-D: Photographs at baseline, 8 hours, 24 hours and 168 hours of samples of RvE1 MgLys alone and RvE1 MgLys complexed with gamma-CD exposed to air under ambient conditions.
Figure 24B:
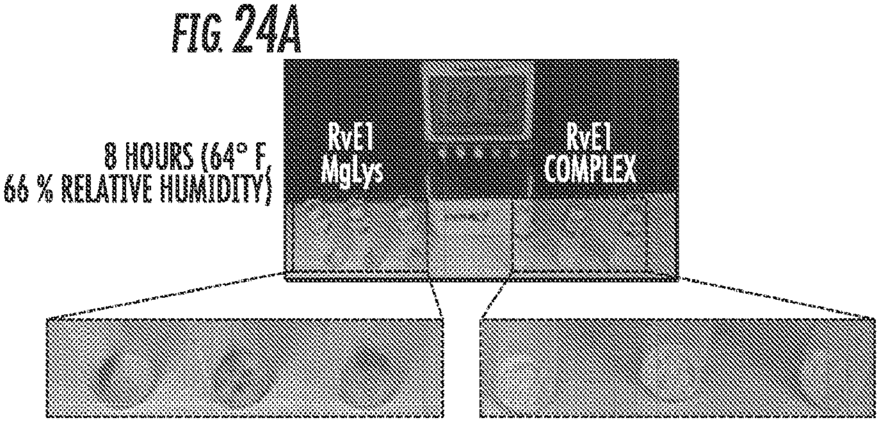
Figure 24C:
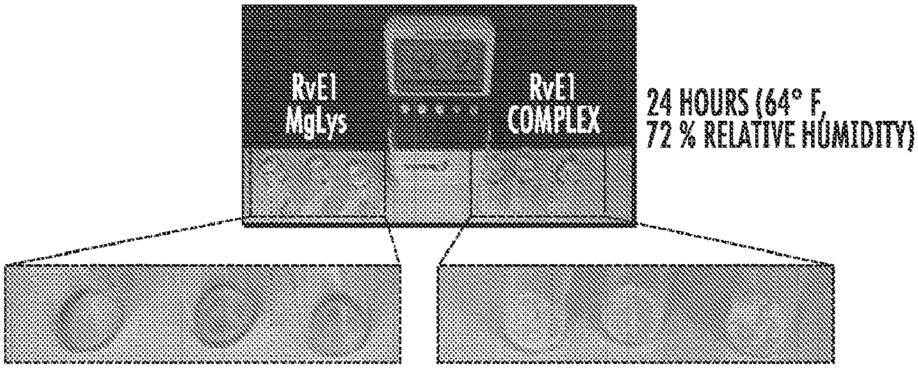
Figure 24D:
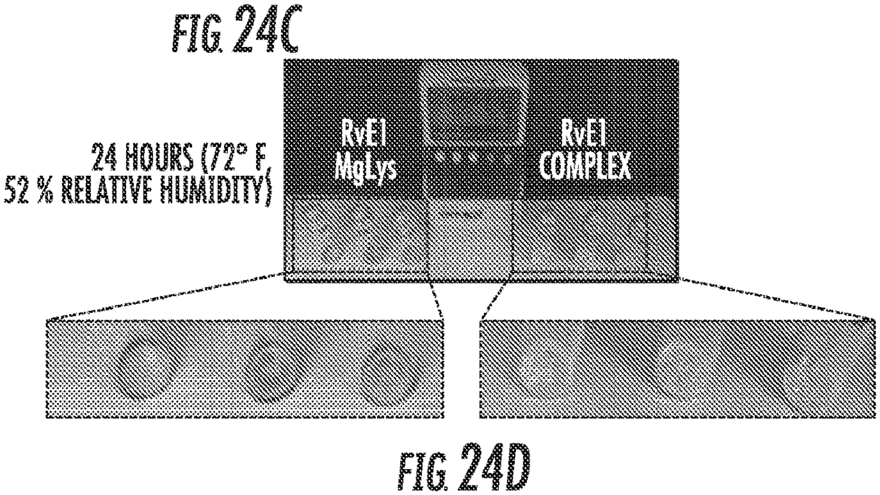

As shown by the dashed and solid rectangles in FIG. 21, intermolecular interaction are indicated between signals of RvE1-MgLys and the core region of SBE-beta-CD. Further analysis of the enlarged section of the intermolecular interactions in 2D ROESY spectrum (FIG. 22) indicate cross-peaks in the region of 3', 5', 6' and α' protons inside the SBE-beta-CD cavity, with a plausible orientation as provided in FIG. 23*e*.

Stability, Pharmacokinetic and Formulation Studies with the Complexes

Example 8: Stabilizing Effects of the Investigated Cyclodextrins on RvE1-MgLys

The stability of RvE1-MgLys alone ("RvE1 Control") and complexed with cyclodextrins ("RvE1 CD Complexes") was evaluated. Samples of the test articles were placed in open test tubes and maintained at 40° C. and 75% relative humidity, exposed to air, for 16 weeks. Quantitative demonstration of stability was determined using HPLC analytic methods. Briefly, HPLC analysis was performed on a Halo Guard column (Halo C18 4.6×150 mm, 2.7 μm), mounted on an Agilent HPLC system equipped with a UV detector (272 nm detection). The mobile phase consisted of a gradient between solution A, water, and solution B, methanol, both containing 100 mM of ammonium formate at pH 4.0. The gradient program was 95-0% with respect to solution A and 5-100% with respect to solution B. The flow rate was 0.9 mL/min over 50 minutes. Lack of stability was indicated by a reduction in the area percent purity (area %) of the single major peak of RvE1 (retention time of 31.3 minutes) and the appearance of new HPLC peaks or an increase in the area % of pre-existing impurities. All HPLC measurements of RvE1 purity and degradant levels were calculated based on area percent relative to the detectable components of the molecule including isomers and epimers of RvE1, impurities and degradants induced by the test conditions.

At the initial time point (baseline), RvE1 eluted as a single major peak, with area % purity of 94% in the RvE1 Control sample and 95.3% to 95.5% in the samples of the RvF1 CD Complexes (Table 3). Following 16 weeks of exposure to the test conditions described above, the RvE1 moiety in the control group had significantly degraded, indicated by the main peak declining to 80.7%. In contrast, the RvE1 moiety in the various RvE1 CD Complexes degraded to a much lesser degree under the same conditions.

As shown in Table 3, the stabilizing effects of complexation with cyclodextrins can be expressed by the change in RvE1 purity from baseline to week 16, otherwise called the degradation rate. The degradation rate of the RvE1 Control at week 16 was 14.1% versus an average degradation rate of 3.9% for the RvE1 CD Complexes. Thus, the degradation rates of the RvE1 in the RvE1 CD complexes were substantially reduced for each cyclodextrin tested.

TABLE 3

RvE1 Purity of RvE1 CD Complexes at 8 and 16 Weeks Under Accelerated Conditions Compared to RvE1 Control

| Test Article | RvE1 Area % Baseline | Week 8 | Week 16 | % Change at Week 16 vs Baseline |
|---|---|---|---|---|
| RvE1 Control | 94.0% | 86.7% | 80.7% | 14.1% |
| RvE1 CD Complexes: | | | | |
| alpha-CD | 95.4% | 92.7% | 92.4% | 3.1% |
| beta-CD | 95.5% | 90.3% | 90.1% | 5.6% |
| gamma-CD | 95.4% | 95.5% | 94.1% | 1.3% |
| HP-beta-CD | 95.3% | 94.5% | 92.9% | 2.5% |
| SBE-beta-CD | 95.5% | 92.6% | 88.9% | 6.9% |
| Average | 95.4% | 93.1% | 91.7% | 3.9% |

Importantly, the superior stability of the RvE1 CD Complexes was also associated with the formation of far fewer degradation peaks greater than or equal to 0.2% or 1.0% at 8 and 16 weeks relative to RvE1 Control under the same conditions (Table 4). Notably, the RvE1 Mg-Lys gamma-cyclodextrin complex demonstrated the fewest number of degradation peaks greater than 0.2%. Overall, the enhanced stability of the RvE1 CD Complexes reduces the risk of potency loss and/or appearance of unknown impurities with potential safety issues during manufacturing, formulation, packaging, storage, and distribution.

TABLE 4

Number of Impurities ≥0.2% and 1.0% at 8 and 16 Weeks Under Accelerated Conditions

| System | # of Deg. Peaks ≥0.20% Baseline | Week 8 | Week 16 | # of Deg. Peaks ≥1.00% Baseline | Week 8 | Week 16 |
|---|---|---|---|---|---|---|
| RvE1 Control | 6 | 19 | 19 | 2 | 4 | 8 |
| RvE1 CD Complexes: | | | | | | |
| alpha-CD | 3 | 12 | 13 | 1 | 2 | 2 |
| beta-CD | 4 | 14 | 15 | 1 | 2 | 2 |
| gamma-CD | 4 | 7 | 7 | 1 | 0 | 2 |
| HP-beta-CD | 4 | 7 | 10 | 1 | 1 | 1 |
| SBE-beta-CD | 4 | 13 | 14 | 1 | 2 | 2 |

Example 9: Long-Term Stabilizing Effects of Cyclodextrins on RvE1-MgLys and Sodium RvE1

A study of the chemical stability of both RvE1-Mg-Lys alone and sodium RvE1 ("Na-RvE1") alone and complexed with cyclodextrins was evaluated over 24 weeks. Samples of the test articles as solids were placed in open test tubes and maintained at 40° C. and 75% relative humidity, exposed to air. Quantitative demonstration of stability was determined using HPLC analytic methods as described above.

As shown in Table 5, at the initial time point (baseline), RvE1 eluted as a single major peak, with area % purity of 94.8% in the sample of RvE1-MgLys alone ("RvE1 MgLys control"), 96.2% in the sample of sodium RvE1 alone ("Na-RvE1 control") and 95.9% to 96.8% in the samples of the cyclodextrin complexes formed from each RvE1 salt ("RvE1 CD Complexes"). Following 24 weeks of exposure to the test conditions described above, the RvE1 moiety of the RvE1-MgLys Control group had significantly degraded, indicated by the main peak declining to 79.1% (consistent with results shown in Table 3), and the RvE1 moiety in the Na-RvE1 Control group had completely degraded to 0%. In contrast, the RvE1 moiety in the RvE1 CD Complexes degraded to a much lesser degree under the same conditions. Importantly, the results shown in Table 5 indicate that the superior stability enabled by complexation with cyclodextrins can be achieved with different initial forms of the RvE1 moiety, in this example with either the sodium or magnesium lysinate salt forms of RvE1.

At week 24, the degradation rates of the RvE1-MgLys control and the Na-RvE1 control were 16.6% and 100%, respectively, versus 0% for the RvE1-MgLys gamma-cyclodextrin complex, 3.4% for the RvE1-MgLys HP-beta-CD complex, and 4.3% for the Na-RvE1 HP-beta-CD complex, consistent with the findings shown in Table 3.

TABLE 5

| RvE1 Purity of -SPM CD Complexes at 24 Weeks Under Accelerated Conditions | | | | | |
|---|---|---|---|---|---|
| | RvE1 Area % (error +/− 1%) | | | | % Change at Week 24 vs |
| Test Article | Baseline | Week 8 | Week 16 | Week 24 | Baseline |
| RvE1 Controls: | | | | | |
| RvE1 Mg-Lys | 94.8% | 88.4% | 82.3% | 79.1% | 16.6% |
| Na-RvE1 | 96.2% | 78.0% | 49.8% | 0.0% | 100.0% |
| RvE1 CD Complexes: | | | | | |
| RvE1 MgLys gamma-CD | 95.9% | 95.7% | 95.5% | 96.1% | 0.0% |
| RvE1 MgLys HP-beta-CD | 95.9% | 93.7% | 92.8% | 92.7% | 3.4% |
| Na-RvE1 HP-beta-CD | 96.8% | 95.6% | 93.7% | 92.6% | 4.3% |

Example 10: Stabilizing Effects of Cyclodextrins on RvE1 Salts in Solution

The chemical stability of RvE1-MgLys or Na-RvE1 alone and complexed with cyclodextrins in solution was evaluated. Samples of the test articles dissolved in deionized water at a concentration of 2 mg/ml of RvE1 were placed in open test tubes and maintained at 40° C. and 75% relative humidity, exposed to air, over a period of 16 weeks. Quantitative demonstration of stability was determined using HPLC analytic methods as described above.

As shown in Table 6, at the initial time point (baseline), RvE1 eluted as a single major peak in all samples, with area % purity of 94.8% to 96.2% in the samples of RvE1-MgLys alone ("RvE1-MgLys Control") and Na-RvE1 alone ("Na-RvE1 Control") and 95.9% to 96.8% in the samples of the RvE1 cyclodextrin complexes ("RvE1 CD Complexes"). Following 16 weeks of exposure to the test conditions described above, the RvE1 moiety in the two control groups had significantly degraded, indicated by the main peak declining to 51.5 in the RvE1-MgLys Control group and 18.6% in the Na-RvE1 Control group. In contrast, the RvE1 moiety in the RvE1 CD Complexes degraded to a much lesser degree under the same conditions.

Together, the superior stability of the RvE1 CD Complexes in solution was unexpected, as there are examples of cyclodextrin compounds that have superior stability as a solid but less stability in solution, or greater stability as a solution but less stability as a solid (Hamada Y, et al., Chem Pharm Bull (Tokyo). 1975; 23 (6): 1205-1211; Uekama 2006; Popielec 2017). Furthermore, the results with both RvE1 Mg-Lys and Na-RvE1 complexed with cyclodextrins indicate that the enhanced stability can be achieved with distinct forms of the RvE1 moiety, in this example, two RvE1 salts with very different stability profiles under accelerated conditions when they are not complexed with cyclodextrins.

TABLE 6

| RvE1 Purity of SPM Complexes In Solution Under Accelerated Conditions | | | | |
|---|---|---|---|---|
| | RvE1 Area % | | | % Change at |
| Test Article | Base-line | Week 8 | Week 16 | Week 16 vs Baseline |
| Controls: | | | | |
| RvE1 Mg-Lys | 94.8% | 84.3% | 51.5% | 45.7% |
| Na-RvE1 | 96.2% | 36.0% | 18.6% | 80.7% |
| SPM Complexcs: | | | | |
| RvE1 MgLys gamma-CD | 95.9% | 91.9% | 87.0% | 9.2% |
| RvE1-MgLys HP-beta-CD | 95.9% | 92.0% | 86.4% | 10.0% |
| Na-RvE1 HP-beta-CD | 96.8% | 93.8% | 83.1% | 14.1% |

Example 11: Solid-State Physical Stability of RvE1 MgLys Gamma-Cyclodextrin Complex The solid-state physical stability of RvE1 MgLys alone ("RvE1 Control") and the RvE1-MgLys gamma-cyclodextrin complex ("RvE1 Complex") was evaluated (FIG. 24A-D). Samples of the test articles as solids were placed in open test tubes under ambient conditions over a period of 168 hours, at temperature between 18-22° C. and relative humidity between 52% and 72%. The solid-state physical stability was assessed visually based on whether the substance retained its form as a solid powder or transitioned to a liquid form.

At the initial time point (baseline) (FIG. 24A), the RvE1 Control and the RvE1 Complex samples were in powder form. At 8 hours (FIG. 24B), the RvE1-Control and the RvE1 Complex samples remained in powder form, although the RvE1 Control samples began to agglomerate and turn a darker color. At 24 and 168 hours (FIG. 24C-D), the RvE1 Control samples had become a gel-like substance, while the samples of the RvE1 Complex maintained their form as solid, off-white powder.

Example 12: Oral Pharmacokinetics of RvE1 Control Versus RvE1 CD Complex

To establish the comparative oral pharmacokinetics ("PK") of RvE1 MgLys alone ("RvE1 Control") and RvE1 MgLys complexed with gamma-cyclodextrin ("RvE1 Complex"), a study was conducted to investigate RvE1 exposure in blood plasma following a single dose of RvE1 Control or RvE1 Complex administered via oral gavage at various timepoints up to 8 hours of 4 mg/kg of RvE1. Quantitative measurement of RvE1 in blood plasma was determined by HPLC-MS/MS performed on a Halo Guard column (Halo C18 4.6×150 mm, 2.7 μm), mounted on an Agilent HPLC system equipped with a UV detector (272 nm detection).

Sixty five (65) male C57B16 mice were randomized into 3 experimental groups at 8 weeks of age: baseline control ("Baseline", n=5), RvE1 Control (n=30) and the RvE1 Complex (n=30). Prior to administration of test article, the mice in the Baseline group were sacrificed and blood was drawn to establish the endogenous levels of RvE1 in plasma. The 60 remaining mice received a single dose of RvE1 Control or RvE1 Complex. Five (5) mice in each group were sacrificed at each of the following timepoints to enable the determination of an RvE1 concentration-versus-time curve: 15 minutes, 30 minutes, 1, 2—, 4- and 8-hours post-dose. At the time of sacrifice blood was drawn into EDTA-treated tubes and immediately frozen.

As shown in the PK curves and the summary of PK metrics in Table 7, the plasma PK of RvE1 Control and RvE1 Complex groups were comparable in terms of area under the cover (AUC, ng/ml*hr), Cmax (ng/ml), and Tmax (min). Together, these data indicate oral administration of the RvE1 Complex is able to deliver comparable levels of RvE1 to systemic circulation as compared to RvE1 Control, thus supporting the utility of cyclodextrins for pharmaceutical development of RvE1.

TABLE 7

Oral Pharmacokinetics of the RvE1 Control Compared to RvE1 Complex

| | RvE1 Control | RvE1 Complex |
|---|---|---|
| Pharmacokinetic time course (ng/ml): | | |
| Pre-dose | 0.1 | 0.1 |
| 15 min | 45.5 | 35.6 |
| 30 min | 6.3 | 9.9 |
| 1 hr | 1.2 | 1.8 |
| 2 hr | 0.2 | 0.3 |
| 4 hr | 0.3 | 0.4 |
| 8 hr | 0.1 | 0.0 |
| Summary: | | |
| AUC (ng/ml*hr) (0 to 8 hrs) | 15.2 | 14.5 |
| Cmax (ng/ml) | 45.5 | 35.6 |
| Tmax | 15 min | 15 min |

Example 13: Formulation Feasibility Study of the RvE1 MgLys Gamma-Cyclodextrin Complex in a Direct Blend with Pharmaceutical Excipients To determine the feasibility of preparing an oral tablet using a salt of RvE1 complexed with a cyclodextrin, a study was conducted to test the flow and compression properties of a direct blend consisting of the RvE1 MgLys gamma-cyclodextrin complex ("RvE1 Complex") and standard pharmaceutical excipients as shown in Table 8 ("Direct Blend"), with no granulation to improve flow characteristics.

TABLE 8

Direct Blend of the RvE1 Complex with Standard Pharmaceutical Excipients

| Ingredient | Function | mg/tab | % w/w |
|---|---|---|---|
| RvE1 MgLys gamma-CD complex | API | 93.0 | 18.6 |
| Avicel PH-200 | Filler | 210.0 | 42.0 |
| Super Tab 11 SD | Filler | 186.5 | 37.3 |
| Colloidal Silicon Dioxide | Gliding agent | 1.0 | 0.2 |
| Sodium Starch Glycolate | Disintegrant | 7.5 | 1.5 |
| Magnesium Stearate | Lubricant | 2.0 | 0.4 |
| TOTAL | | 500.0 | 100.0 |

In the flow portion of the study, the Direct Blend without granulation was first evaluated to determine the particle size distribution ("PSD") using screen meshes ranging from #40 (course) to #325 (fine), corresponding to mesh diameters ranging from 400 to 44 microns. As shown in Table 9, approximately 75% of the Direct Blend particles were more than or equal to 100 microns (coarser) and approximately 25% were less than 100 microns in diameter (finer). Once the particle size distribution of the Direct Blend was established, a flow experiment was conducted using an orifice with a diameter of 16 mm. In this portion of the study, the Direct Blend without additional granulation demonstrated adequate flow to pass through the 16 mm orifice, which is sufficient to enable gravity feed during compression on a rotary press or direct fill into a capsule.

TABLE 9

Particle Size Distribution of the Direct Blend

| | Mesh # | | | | | | | |
|---|---|---|---|---|---|---|---|---|
| | 40 | 60 | 80 | 100 | 140 | 200 | 325 | Fines |
| Diameter (micron) | 400 | 250 | 177 | 149 | 105 | 74 | 44 | <44 |
| PSD (%) | 0.7 | 19.6 | 16.6 | 18.4 | 19.3 | 11.7 | 8.0 | 5.8 |

| Particle Size Distribution Summary (%) | |
|---|---|
| Total >100 microns (courser) | 75% |
| Total <100 microns (finer) | 25% |

Figure 25A:
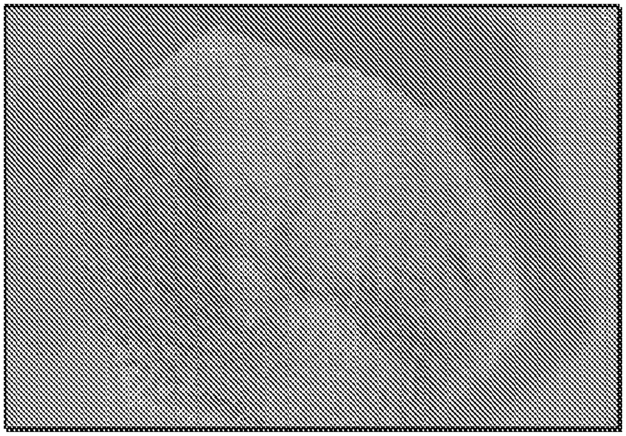
FIG. 25A-B: Photographs of a direct blend of RvE1 MgLys complexed with gamma-CD and standard pharmaceutical excipients without additional granulation before tableting (A) and after compression into core tablets (B).
Figure 25B:
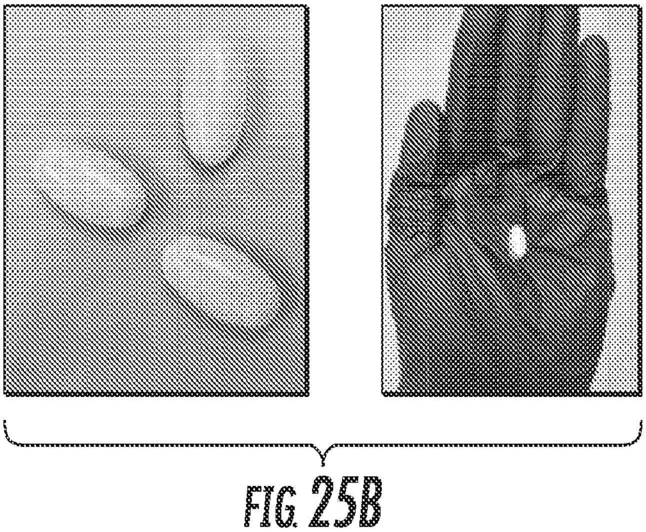
Figure 26:
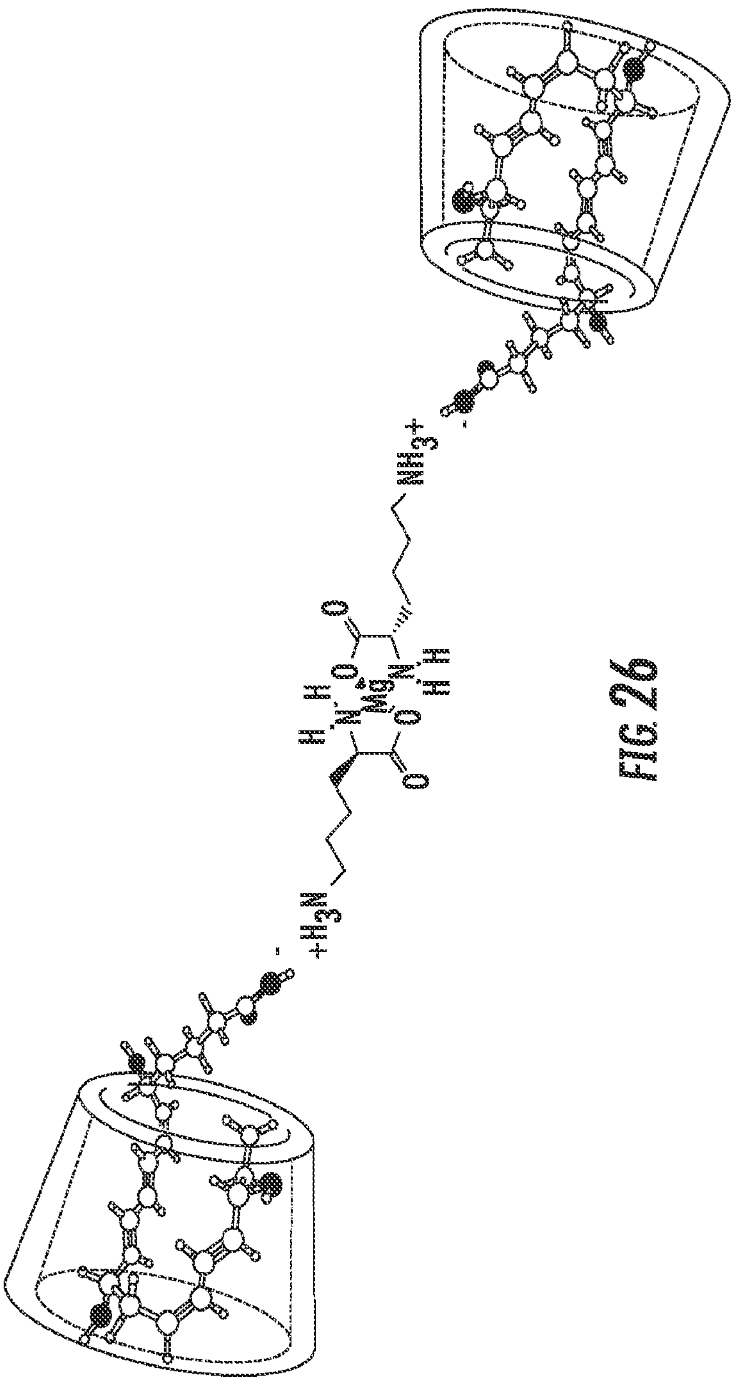
FIG. 26: Schematic representation of the complex of RvE1 magnesium dilysinate (RvE1 MgLys) and gamma-cyclodextrin (gamma-CD).

In the compression portion of the study, the Direct Blend was compressed on a rotary press with oval shaped tooling (0.5457 cm×2852 cm) at a compression force of approximately 100 bar, producing a tablet of approximately 5.8 mm in thickness (see FIG. 25A-B). The tablets with a target gross weight of 500 mg per tablet were prepared in two groups: low and high hardness (18 and 30 kilopond, respectively), As shown in Table 10, the tablets in both groups had minimal weight variation and exhibited hardness, friability and disintegration time characteristics that were consistent with the target specification.

TABLE 10

Compression Study of the GCD Complex Direct Blend

| Parameter | Low (18 kp) | High (30 kp) |
|---|---|---|
| Individual weight (mg) | 503-507 | 498-501 |
| Thickness (mm) | 7.3 | 6.3 |

TABLE 10-continued

| Compression Study of the GCD Complex Direct Blend | | |
|---|---|---|
| Parameter | Low (18 kp) | High (30 kp) |
| Hardness (kp) | 17-20 | 27-30 |
| Friability (%) | 0.1 | 0.0 |
| Disintegration | 1 min 12 sec | 5 min 23 sec |

EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A complex of a resolvin E1 (RvE1), or a salt, ester, or amide thereof, and gamma-cyclodextrin (gamma-CD), wherein the molar ratio of RvE1 to gamma-CD in the complex is 1:1.

2. The complex of claim 1, wherein the RvE1 is in the form of a salt.

3. The complex of claim 2, wherein the RvE1 is in the form of a sodium, potassium, calcium, zinc, magnesium, or magnesium dilysinate salt.

4. The complex of claim 3, wherein the RvE1 is an RvE1 sodium salt.

5. The complex of claim 3, wherein the RvE1 is in the form of a salt described by Formula I:

(Formula I)

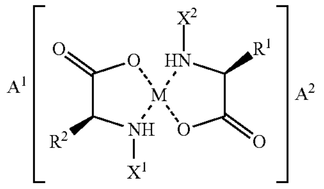

wherein

M is a divalent metal selected from magnesium ($Mg^{2+}$), calcium ($Ca^{2+}$), and zinc ($Zn^{2+}$);

$A^1$ and $A^2$ are each RvE1;

$R^1$ and $R^2$ are each independently a $C_1$-$C_{10}$ alkyl comprising at least one basic function; and $X^1$ and $X^2$ are each independently H or CO—Z and Z is a peptide comprising 1 to 5 amino acids.

6. The complex of claim 5, wherein M is selected from magnesium ($Mg^{2+}$) or calcium ($Ca^{2+}$).

7. The complex of claim 5, wherein $R^1$ and $R^2$ are each independently $—(CH_2)_3—Y^1$, and $—(CH_2)_4—Y^2$, and $Y^1$ and $Y^2$ are each selected from a positively charged primary amine, a positively charged secondary amine, a positively charged tertiary amine, and a positively charged guanidine.

8. The complex of claim 5, wherein $X^1$ and $X^2$ are each H.

9. The complex of claim 5, wherein $R^1$ and $R^2$ are each $—(CH_2)_4—Y^2$ and $Y^2$ is $—NH_3^+$.

10. The complex of claim 5, wherein M is magnesium ($Mg^{2+}$), $R^1$ and $R^2$ are each $—(CH_2)_4—Y^2$ and $Y^2$ is $—NH_3^+$, $X^1$ and $X^2$ are each H, which resolvin of the complex is referred to as RvE1 magnesium dilysinate, or "RvE1 MgLys".

11. The complex of claim 1, wherein the RvE1 is a sodium, potassium, calcium, zinc, or magnesium salt of RvE1.

12. A complex of RvE1 MgLys and gamma-cyclodextrin (gamma-CD), wherein the molar ratio of RvE1 to gamma-CD in the complex is 1:1.

13. A complex of a sodium salt of RvE1 and gamma-cyclodextrin (gamma-CD), wherein the molar ratio of RvE1 to gamma-CD in the complex is 1:1.

14. A pharmaceutical composition comprising the complex of claim 1, and one or more pharmaceutically acceptable carriers and/or excipients.

15. A method of treating an inflammatory disease or disorder of the gastrointestinal tract in a subject in need thereof, the method comprising administering to the subject the pharmaceutical composition of claim 14.

16. A method of treating cancer in a subject in need thereof, the method comprising administering to the subject the pharmaceutical composition of claim 14.

17. A pharmaceutical composition comprising the complex of claim 12, and one or more pharmaceutically acceptable carriers and/or excipients.

18. A pharmaceutical composition comprising the complex of claim 13, and one or more pharmaceutically acceptable carriers and/or excipients.

* * * * *